United States Patent
Mookerjee et al.

(10) Patent No.: US 10,975,395 B2
(45) Date of Patent: Apr. 13, 2021

(54) METHOD AND CELL LINE FOR PRODUCTION OF POLYKETIDES IN YEAST

(71) Applicant: Hyasynth Biologicals Inc., Montreal (CA)

(72) Inventors: Shoham Mookerjee, Montreal (CA); Alexander James Campbell, Montreal (CA); Zachary Douglas Wiltshire, Montreal (CA); Kevin John Chen, Montreal (CA)

(73) Assignee: Hyasynth Biologicals Inc., Montreal (CA)

( * ) Notice: Subject to any disclaimer, the term of this patent is extended or adjusted under 35 U.S.C. 154(b) by 0 days.

(21) Appl. No.: 16/828,696

(22) Filed: Mar. 24, 2020

(65) Prior Publication Data

US 2020/0239916 A1   Jul. 30, 2020

Related U.S. Application Data

(63) Continuation of application No. 16/486,618, filed as application No. PCT/CA2018/050190 on Feb. 19, 2018.

(60) Provisional application No. 62/460,526, filed on Feb. 17, 2017.

(51) Int. Cl.
| | |
|---|---|
| *C12N 9/00* | (2006.01) |
| *C12P 7/22* | (2006.01) |
| *C07K 14/395* | (2006.01) |
| *C12N 9/04* | (2006.01) |
| *C12N 9/10* | (2006.01) |
| *C12N 9/12* | (2006.01) |
| *C12N 15/52* | (2006.01) |

(52) U.S. Cl.
CPC .............. *C12P 7/22* (2013.01); *C07K 14/395* (2013.01); *C12N 9/0006* (2013.01); *C12N 9/1029* (2013.01); *C12N 9/1085* (2013.01); *C12N 9/1288* (2013.01); *C12N 9/93* (2013.01); *C12N 15/52* (2013.01); *C12Y 205/01041* (2013.01); *C12Y 101/01001* (2013.01); *C12Y 203/01* (2013.01); *C12Y 207/08007* (2013.01); *C12Y 602/01001* (2013.01)

(58) Field of Classification Search
None
See application file for complete search history.

(56) References Cited

U.S. PATENT DOCUMENTS

| | | |
|---|---|---|
| 7,361,482 B2 | 4/2008 | Chang et al. |
| 7,361,483 B2 | 4/2008 | Kuzuyama et al. |
| 8,124,390 B2 | 2/2012 | Kuzuyama et al. |
| 8,884,100 B2 | 11/2014 | Page et al. |
| 9,359,625 B2 | 6/2016 | Winnicki et al. |
| 9,394,510 B2 | 7/2016 | Peet et al. |
| 9,670,494 B2 | 6/2017 | Nielsen et al. |
| 9,765,308 B2 | 9/2017 | Page et al. |
| 2008/0020438 A1 | 1/2008 | Matsuda et al. |
| 2012/0122180 A1 | 5/2012 | Austin et al. |
| 2013/0197248 A1 | 8/2013 | Nielsen et al. |
| 2014/0141476 A1 | 5/2014 | Page et al. |
| 2014/0330032 A1 | 11/2014 | Lynch et al. |
| 2016/0010126 A1 | 1/2016 | Poulos et al. |
| 2016/0138056 A1 | 5/2016 | Jensen et al. |

FOREIGN PATENT DOCUMENTS

| | | |
|---|---|---|
| EP | 1338608 A2 | 8/2003 |
| WO | 03072602 A2 | 9/2003 |
| WO | 2006060839 A2 | 6/2006 |
| WO | 2006081537 A2 | 8/2006 |
| WO | 2011127589 A1 | 10/2011 |
| WO | 2012017083 A1 | 2/2012 |
| WO | 2013006853 A1 | 1/2013 |
| WO | 2014018982 A1 | 1/2014 |
| WO | 2014207113 A1 | 12/2014 |
| WO | 2015032911 A1 | 3/2015 |
| WO | 2016010827 A1 | 1/2016 |
| WO | 2016159869 A1 | 10/2016 |
| WO | 2017139496 A1 | 8/2017 |
| WO | 2017161041 A1 | 9/2017 |
| WO | 2018200888 A1 | 11/2018 |

OTHER PUBLICATIONS

AB164375 Nucleic Acid Sequence, NCBI [online database], Sequence Deposited Mar. 28, 2008 (Mar. 28, 2008), Retrieved from the internet: [URL: https://www.ncbi.nlm.nih.gov/nuccore/AB164375].
Austin et al., "Biosynthesis of Dictyostelium Discoideum Differentiation-Inducing Factor by a Hybrid Type I Fatty Acid—Type III Polyketide Synthase," Nature Chemical Biology, Sep. 2006, vol. 2 (9), pp. 494-502.

(Continued)

*Primary Examiner* — Rebecca E Prouty

(74) *Attorney, Agent, or Firm* — Fish & Richardson P.C.

(57) ABSTRACT

A method and cell line for producing polyketides in yeast. The method applies, and the cell line includes, a yeast cell transformed with a polyketide synthase coding sequence. The polyketide synthase enzyme catalyzes synthesis of olivetol or methyl-olivetol, and may include *Dictyostelium discoideum* polyketide synthase ("DiPKS"). Wild type DiPKS produces methyl-olivetol only. DiPKS may be modified to produce olivetol only or a mixture of both olivetol and methyl-olivetol. The yeast cell may be modified to include a phosphopantethienyl transferase for increased activity of DiPKS. The yeast cell may be modified to mitigate mitochondrial acetaldehyde catabolism for increasing malonyl-CoA available for synthesizing olivetol or methyl-olivetol.

3 Claims, 7 Drawing Sheets

Specification includes a Sequence Listing.

(56) References Cited

OTHER PUBLICATIONS

Baba et al., "Yeast Coq5 C-Methyltransferase Is Required for Stability of Other Polypeptides Involved in Coenzyme Q Biosynthesis," The Journal of Biological Chemistry, Mar. 2004, vol. 279 (11), pp. 10052-10059.

Bonitz et al., "Evolutionary Relationships of Microbial Aromatic Prenyltransferases," PLoS One, Nov. 2011, vol. 6 (11), pp. e27336.

Carvalho et al., "Designing Microorganisms for Heterologous Biosynthesis of Cannabinoids," FEMS Yeast Research, Jun. 2017, vol. 17 (4), pp. 1-11, ISSN 1567-1356.

Chambon et al., "Isolation and Properties of Yeast Mutants Affected in Farnesyl Diphosphate Synthetase," Current Genetics, Jul. 1990, vol. 18 (1), pp. 41-46.

Cheon et al., "A Biosynthetic Pathway for Hexanoic Add Production in Kluyveromyces Marxianus," Journal of Biotechnology, Jul. 2014, vol. 182-183, pp. 30-36.

Degenhardt et al., "Chapter 2. The Biosynthesis of Cannabinoids," Dec. 2017, pp. 13-23.

Fellermeier et al., "Biosynthesis of Cannabinoids. Incorporation Experiments With (13)C-Labeled Glucoses," European Journal of Biochemistry, Mar. 2001, vol. 268 (6), pp. 1596-1604.

Fellermeier, "Prenylation of Olivetolate by a Hemp Transferase Yields Cannabigerolic Acid, the Precursor of Tetrahydrocannabinol," FEBS Letters, May 1998, vol. 427 (2), pp. 283-285.

Fischer et al., "Metabolic Engineering of Monoterpene Synthesis in Yeast," Biotechnology and Bioengineering, Aug. 2011, vol. 108 (8), pp. 1883-1892.

Flagfeldt et al., "Charactenzation of Chromosomal Integration Sites for Heterologous Gene Expression in Saccharomyces cerevisiae," Yeast, Oct. 2009, vol. 26 (10), pp. 545-551.

Flemming et al., "Chemistry and Biological Activity of Tetrahydrocannabinol and its Derivatives," Topics in Heterocyclic Chemistry, Bioactive Heterocycles IV, Aug. 2007, vol. 10, pp. 1-42.

Gagne et al., "Identification of Olivetolic Acid Cyclase From Cannabis Sativa Reveals a Unique Catalytic Route to Plant Polyketides," Proceedings of the National Academy of Sciences of the United States of America, Jul. 2012, vol. 109 (31), pp. 12811-12816.

Gagne., "The Polyketide Origins of Cannabinoids in Cannabis Sativa," A Thesis Submitted to the College of Graduate Studies and Research In Partial Fulfillment of the Requirements For the Degree of Doctor of Philosophy In the Department of Biology, University of Saskatchewan, 2013, 263 pages.

Ghosh et al., "Dissecting the Functional Role of Polyketide Synthases in Dictyostelium Discoideum: Biosynthesis of the Differentiation Regulating Factor 4-methyl-5-pentylbenzene-1,3-diol," The Journal of Biological Chemistry, Apr. 2008, vol. 283 (17), pp. 11348-11354, ISSN 0021-9258.

Gietz et al., "High-Efficiency Yeast Transformation Using the LiAc/SS Carrier DNA/PEG Method," Nature Protocols, 2007, vol. 2 (1), pp. 31-34.

Gietz et al., "Yeast Transformation by the LiAc/SS Carrier DNA/PEG Method," Methods in Molecular Biology, 2014, vol. 1205. https://doi.org/10.1007/978-1-4939-1363-3_1.

Huang et al., "Effect of Organic Acids on the Growth and Lipid Accumulation of Oleaginous Yeast Trichosporon Fermentans," Biotechnology for Biofuels, Jan. 2012, vol. 5 (1), pp. 4.

Hunkova et al., "Toxic Effects of Fatly Acids on Yeast Cells: Dependence of Inhibitory Effects on Fatty Acid Concentraton," Biotechnology and Bioengineering, Nov. 1977, vol. 19 (11), pp. 1623-1641.

International Patent Application No. PCT/CA2018/050190, International Search Report and Written Opinion dated May 31, 2018.

International Patent Application No. PCT/CA2018/50190, International Preliminary Report on Patentability dated Jul. 5, 2019.

Jensen et al., "EasyClone: Method for Iterative Chromosomal Integration of Multiple Genes in Saccharomyces cerevisiae," FEMS Yeast Research, Mar. 2014, vol. 14(2), pp. 238-248. https://doi.org/10.1111/1567-1364.12118.

Kaminska et al., "The Isoprenoid Biosynthetic Pathway in Saccharomyces cerevisiae is Affected in a maf1-1 Mutant With Altered tRNA Synthesis" FEMS Yeast Research, Mar. 2002, vol. 2 (1), pp. 31-37.

Kim et al., "Characterization of NpgA, a 4'-Phosphopantetheinyl Transferase of Aspergillus Nidulans, and Evidence of Its Involvement in Fungal Growth and Formation of Conidia and Cleistothecia for Development" Journal of Microbiology, Jan. 2015, vol. 53 (1), pp. 21-31.

Krivoruchko et al., "Microbial Acetyl-CoA Metabolism and Metabolic Engineering," Metabolic Engineering, Mar. 2015, vol. 28, pp. 28-42.

Kuzuyama et al., "Structural Basis for the Promiscuous Biosynthetic Prenylation of Aromatic Natural Products," Nature, Jun. 2005, vol. 435 (7044), pp. 983-987.

Liu at al., "Overproduction of Geraniol by Enhanced Precursor Supply in Saccharomyces cerevisiae," Journal of Biotechnology, Dec. 2013, vol. 168 (4), pp. 446-451.

NCBI GenBank online database under Accession No. NC 007087.3, Jan. 2010.

NCBI GenBank online database under accession No. NCBI AB187169, Oct. 2015.

Oswald et al., "Monoterpenoid Biosynthesis in Saccharomyces cerevisiae," FEMS Yeast Research, May 2007, vol. 7(3), pp. 413-421. https://doi.org/10.1111/j.1567-1364.2006.00172.x.

Pamplaniyil., "Identification, Isolation and Functional Characterization of Prenyltransferases in Cannabis sativa L.," Faculty of Biochemical and Chemical Engineering, The Technical Universal of Dortmund, Dissertation, 2016, 139 pages.

Razdan., "Structure-Activity Relationships in Cannabinoids," Pharmacological Reviews, Jun. 1986, vol. 38 (2), pp. 75-149.

Ro et al., "Production of the Antimalarial Drug Precursor Artemisinic Acid in Engineered Yeast," Nature Letters, Apr. 2006, vol. 440(7086), pp. 940-943.

Ryan et al., "CRISPR-Cas9 Genome Engineering in Saccharomyces cerevisiae Cells," Cold Spring Harbor Protocols, Jun. 2016, vol. 2016(6). https://doi.org/10.1101/pdb.prot086827.

Schreckenbach., "Enzymatische Oligomerisierung von Alkendiphosphaten," Martin Luther University Halle-Wittenberg, Dissertation, 2017, 159 pages.

Shi et al., "Improving Production of Malonyl Coenzyme A-Derived Metabolites by Abolishing Snf1-Dependent Regulation of Acc1" American Society for Microbiology, May 2014, vol. 5 (3), pp. e01130-14.

Shiba et al., "Engineering of the Pyruvate Dehydrogenase Bypass in Saccharomyces cerevisiae for High-Level Production of Isoprenoids," Metabolic Engineering, Mar. 2007, vol. 9 (2), pp. 160-168.

Skiba et al., "Domain Organization and Active Site Architecture of a Polyketide Synthase C-Methyltransferase," ACS Chemical Biology, Dec. 2016, vol. 11 (12), pp. 3319-3327.

Stout et al., "The Hexanoyl-CoA Precursor for Cannabinoid Biosynthesis is Formed by an Acyl-activating Enzyme in Cannabis Sativa Trichomes," The Plant Journal, Aug. 2012, vol. 71 (3), pp. 353-365.

Sugiyama et al., "Metabolic Engineering for the Production of Prenylated Polyphenols in Transgenic Legume Plants Using Bacterial and Plant Prenyltransferases," Metabolic Engineering, Nov. 2011, vol. 13 (6), pp. 629-637.

Taura et al., "Characterization of Olivetol Synthase, A Polyketide Synthase Putatively Involved in Cannabinoid Biosynthetic Pathway," FEBS Letters, Jun. 2009, vol. 563 (12), pp. 2061-2066, ISSN 0014-5793.

Taura et al., "First Direct Evidence for the Mechanism of .DELTA.1-tetrahydrocannabinolic Acid Biosynthesis," Journal of the American Chemical Society, Sep. 1995, vol. 117, pp. 9766-9767.

Tello et al., "The ABBA Family of Aromatic Prenyltransferases: Broadening Natural Product Diversity," Cellular and Molecular Life Sciences, May 2008, vol. 65 (10), pp. 1459-1463.

Viegas et al., "Inhibition of Yeast Growth by Octanoic and Decanoic Acids Produced during Ethanolic Fermentation," Applied and Environmental Microbiology, Jan. 1989, vol. 55 (1), pp. 21-28.

(56) References Cited

OTHER PUBLICATIONS

Zirpel et al., "Engineering Yeasts as Platform Organisms for Cannabinoid Biosynthesis," Journal of Biotechnology, Oct. 2017, vol. 259, pp. 204-212, ISSN 0168-1656.
Zirpel et al., "Production of DELTA 9-Tetrahydrocannabinolic Acid From Cannabigerolic Acid by Whole Cells of Pichia (*Komagataella*) Pastoris Expressing DELTA 9-Tetrahydrocannabinolic Acid Synthase From *Cannabis sativa* L," Biotechnology letters, Sep. 2015, vol. 37 (9), pp. 1869-1875.
Cannabis Sativa OLS mRNA for Olivetol Synthase—TAURA at. el., "Characterization of Olivetol Synthase, a Polyketide Synthase Putatively Involved in Cannabinoid Biosynthetic Pathway," FEBS Letters 583 (2009) 2061-2066, (available online May 19, 2009).
European Patent Application No. 18754640.3, Supplementary European Search Report dated Nov. 30, 2020.
Hanus et al., "Phytocannabinoids: A Unified Critical Inventory," Natural Product Reports, Nov. 23, 2016, vol. 33 (12), pp. 1357-1392.
Singapore Patent Application No. SG11201907469Y, Search Report and Written opinion dated Nov. 30, 2020.
Stehle et al., "Biotechnological Synthesis of Tetrahydrocannabinolic Acid Heterologe Biosynthese Der Tetrahydrocannabinolsäure," Pharmakon, Mar. 2017, vol. 5(2), pp. 142-147.
Zucko et al., "Polyketide Synthase Genes and the Natural Products Potential of Dictyostelium Discoideum," Bioinformatics, 2007, vol. 23(19). pp. 2543-2549.

METHOD AND CELL LINE FOR PRODUCTION OF POLYKETIDES IN YEAST

CROSS REFERENCE TO RELATED APPLICATIONS

This application is a continuation of U.S. patent application Ser. No. 16/486,618, filed Aug. 16, 2019, which is the National Stage of International Application No. PCT/CA2018/050190, filed Feb. 19, 2018, which claims the benefit of priority of U.S. Provisional Patent Application No. 62/460,526, entitled METHOD AND CELL LINE FOR PRODUCTION OF PHYTOCANNABINOIDS IN YEAST, filed Feb. 17, 2017, which are hereby incorporated by reference in their entirety.

FIELD

The present disclosure relates generally to production of polyketides in yeast.

BACKGROUND

Polyketides are precursors to many valuable secondary metabolites in plants.

For example, phytocannabinoids, which are naturally produced in Cannabis sativa, other plants, and some fungi, have significant commercial value. Over 105 phytocannabinoids are known to be biosynthesized in C. sativa, or result from thermal or other decomposition from phytocannabinoids biosynthesized in C. sativa. While the C. sativa plant is also a valuable source of grain, fiber, and other material, growing C. sativa for phytocannabinoid production, particularly indoors, is costly in terms of energy and labour. Subsequent extraction, purification, and fractionation of phytocannabinoids from the C. sativa plant is also labour and energy intensive.

Phytocannabinoids are pharmacologically active molecules that contribute to the medical and psychotropic effects of C. sativa. Biosynthesis of phytocannabinoids in the C. sativa plant scales similarly to other agricultural projects. As with other agricultural projects, large scale production of phytocannabinoids by growing C. sativa requires a variety of inputs (e.g. nutrients, light, pest control, $CO_2$, etc.). The inputs required for cultivating C. sativa must be provided. In addition, cultivation of C. sativa, where allowed, is currently subject to heavy regulation, taxes, and rigorous quality control where products prepared from the plant are for commercial use, further increasing costs. Phytocannabinoid analogues are pharmacologically active molecules that are structurally similar to phytocannabinoids. Phytocannabinoid analogues are often synthesized chemically, which can be labour intensive and costly. As a result, it may be economical to produce the phytocannabinoids and phytocannabinoid analogues in a robust and scalable, fermentable organism. Saccharomyces cerevisiae is an example of a fermentable organism that has been used to produce industrial scales of similar molecules.

The time, energy, and labour involved in growing C. sativa for production of naturally-occurring phytocannabinoids provides a motivation to produce transgenic cell lines for production of phytocannabinoids by other means. Polyketides, including olivetolic acid and its analogues are valuable precursors to phytocannabinoids.

SUMMARY

It is an object of the present disclosure to obviate or mitigate at least one disadvantage of previous approaches to producing phytocannabinoids outside of the C. sativa plant, and of previous approaches to producing phytocannabinoid analogues. Many of the 105 phytocannabinoids found in Cannabis sativa may be biosynthesized from olivetolic acid or olivetol. Phytocannabinoids and their analogues may also be chemically synthesized from olivetol and other reagents. Olivetol and olivetolic acid may also be used in pharmaceutical or nutritional product development as well. As a consequence it may be desirable to improve yeast-based production of olivetol, olivetolic acid or analogues of either olivetol or olivetolic acid. Similarly, an approach that allows for production of phytocannabinoid analogues without the need for labour-intensive synthesis may be desirable.

The methods and cells lines provided herein may apply and include Saccharomyces cerevisiae that has been transformed to include a gene for Dictyostelium discoideum polyketide synthase ("DiPKS"). DiPKS is a fusion protein consisting of both a type I fatty acid synthase ("FAS") and a polyketide synthase ("PKS") and is referred to as a hybrid "FAS-PKS" protein. DiPKS catalyzes synthesis of methylolivetol from malonyl-CoA. The reaction has a 6:1 stoichiometric ratio of malonyl-CoA to methyl-olivetol. Downstream prenyltransferase enzymes catalyzes synthesis of methyl cannabigerol ("meCBG") from methyl-olivetol and geranyl pyrophosphate ("GPP"), similarly to synthesis of cannabigerolic acid ("CBGa") from olivetolic acid and GPP. Hexanoic acid is toxic to S. cerevisiae. Hexanoyl-CoA is a precursor for synthesis of olivetol by Cannabis Sativa olivetolic acid synthase ("OAS"). As a result, when using DiPKS rather than OAS, hexanoic acid need not be added to the growth media, which may result in increased growth of the S. cerevisiae cultures and greater yield of meCBG compared with yields of CBG when using OAS. In addition, in C. sativa, the olivetol is carboxylated in the presence of olivetolic acid cyclase ("OAC") or another polyketide cyclase into olivetolic acid, which feeds into the CBGa synthesis metabolic pathway, beginning with prenylation of olivetolic acid catalyzed by in C. sativa by a membrane-bound prenyltransferase. The option to produce olivetol or methyl-olivetol rather than olivetolic acid may facilitate preparation of decarboxylated species of phytocannabinoids and methylated analogues of phytocannabinoids.

For some applications, meCBG and methylated downstream phytocannabinoid analogues that can be synthesized from meCBG (similarly to downstream phytocannabinoids being synthesized from CBGa in C. sativa) may be valuable. In other cases, phytocannabinoids structurally identical to the decarboxylated forms of naturally-occurring phytocannabinoids may be more desirable. For production of phytocannabinoids that are structurally identical to the decarboxylated forms of naturally-occurring phytocannabinoids, DiPKS may be modified relative to wild type DiPKS to reduce methylation of olivetol, resulting in synthesis of either both olivetol and methyl-olivetol Synthesis of olivetol and methyl-olivetol may be facilitated by increased levels of malonyl-CoA in the cytosol. The S. cerevisiae may have overexpression of native acetaldehyde dehydrogenase and expression of a mutant acetyl-CoA synthase or other gene, the mutations resulting in lowered mitochondrial acetaldehyde catabolism. Lowering mitochondrial acetaldehyde catabolism by diverting the acetaldehyde into acetyl-CoA production increases malonyl-CoA available for synthesizing olivetol. Acc1 is the native yeast malonyl CoA synthase. The S. cerevisiae may have overexpression of Acc1 or modification of Acc1 for increased activity and increase available malonyl-CoA. The S. cerevisiae may include modified expression of Maf1 or other regulators of tRNA biosynthesis. Overexpressing native Maf1 has been shown to reduce loss of isopentyl pyrophosphate ("IPP") to tRNA biosynthesis and thereby improve monoterpene yields in yeast. IPP is an intermediate in the mevalonate pathway. Upc2 is an activator for sterol biosynthesis in *S. cerevisiae*, and a Glu888Asp mutation of Upc2 may increase monoterpene production in yeast. The *S. cerevisiae* may include a co-factor loading enzyme to increase the activity of DiPKS. Other species of yeast, including *Yarrowia lipolytica*, *Kluyveromyces marxianus*, *Kluyveromyces lactis*, *Rhodosporidium toruloides*, *Cryptococcus curvatus*, *Trichosporon pullulan* and *Lipomyces lipoferetc*, may be applied.

In a first aspect, herein provided is a method and cell line for producing polyketides in yeast. The method applies, and the cell line includes, a yeast cell transformed with a polyketide synthase coding sequence. The polyketide synthase enzyme catalyzes synthesis of olivetol or methyl-olivetol, and may include *Dictyostelium discoideum* polyketide synthase ("DiPKS"). Wild type DiPKS produces methyl-olivetol only. DiPKS may be modified to produce olivetol only or a mixture of both olivetol and methyl-olivetol. The yeast cell may be modified to include a phosphopantetheinyl transferase for increased activity of DiPKS. The yeast cell may be modified to mitigate mitochondrial acetaldehyde catabolism for increasing malonyl-CoA available for synthesizing olivetol or methyl-olivetol.

In a further aspect, herein provided is a method of producing a polyketide, the method comprising: providing a yeast cell comprising a first polynucleotide coding for a polyketide synthase enzyme and propagating the yeast cell for providing a yeast cell culture. Tpolyketide synthase enzyme is for producing at least one species of polyketide from malonyl-CoA, the polyketide having structure I:

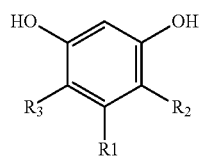

On structure I, R1 is a pentyl group. On structure I, R2 is H, carboxyl, or methyl. On structure I, R3 is H, carboxyl, or methyl.

In some embodiments, the polyketide synthase enzyme comprises a DiPKS polyketide synthase enzyme from *D. discoideum*. In some embodiments, the first polynucleotide comprises a coding sequence for the DiPKS polyketide synthase enzyme with a primary structure having between 80% and 100% amino acid residue sequence homology with a protein coded for by a reading frame defined by bases 535 to 9978 of SEQ ID NO: 13. In some embodiments, the first polynucleotide has between 80% and 100% base sequence homology with bases 535 to 9978 of SEQ ID NO: 13. In some embodiments, the at least one species of polyketide comprises a polyketide with a methyl group at R2. In some embodiments, he DiPKS polyketide synthase enzyme comprises a mutation affecting an active site of a C-Met domain for mitigating methylation of the at least one species of polyketide, resulting in the at least one species of polyketide comprising a first polyketide wherein R2 is methyl and R3 is H, and a second polyketide wherein R2 is H and R3 is H. In some embodiments, the DiPKS polyketide synthase comprises a DiPKS$^{G1516D; G1518A}$ polyketide synthase. In some embodiments, the first polynucleotide comprises a coding sequence for the DiPKS$^{G1516D; G1518A}$ polyketide synthase enzyme with a primary structure having between 80% and 100% amino acid residue sequence homology with a protein coded for by a reading frame defined by bases 523 to 9966 of SEQ ID NO: 9. In some embodiments, the first polynucleotide has between 80% and 100% base sequence homology with bases 523 to 9966 of SEQ ID NO: 9. In some embodiments, the DiPKS polyketide synthase comprises a DiPKS$^{G1516R}$ polyketide synthase. In some embodiments, the first polynucleotide comprises a coding sequence for the DiPKS$^{G1516R}$ polyketide synthase enzyme with a primary structure having between 80% and 100% amino acid residue sequence homology with a protein coded for by a reading frame defined by bases 523 to 9966 of SEQ ID NO: 10. In some embodiments, the first polynucleotide has between 80% and 100% base sequence homology with bases 523 to 9966 of SEQ ID NO: 10. In some embodiments, the DiPKS polyketide synthase enzyme comprises a mutation reducing activity at an active site of a C-Met domain of the DiPKS polyketide synthase enzyme, for preventing methylation of the at least one species of polyketide, resulting in the at least one species of polyketide having a hydrogen R2 group and a hydrogen R3 group. In some embodiments, the yeast cell comprises a second polynucleotide coding for a phosphopantetheinyl transferase enzyme for increasing the activity of DiPKS. In some embodiments, the phosphopantetheinyl transferase comprises NpgA phosphopantetheinyl transferase enzyme from *A. nidulans*. In some embodiments, wherein the second polynucleotide comprises a coding sequence for the NpgA phosphopantetheinyl transferase enzyme from *A. nidulans* with a primary structure having between 80% and 100% amino acid residue sequence homology with a protein coded for by a reading frame defined by bases 1170 to 2201 of SEQ ID NO: 8. In some embodiments, the second polynucleotide has between 80% and 100% base sequence homology with bases 1170 to 2201 of SEQ ID NO: 8.

In some embodiments, the polyketide synthase enzyme comprises an active site for synthesizing the at least one species of polyketide from malonyl-CoA without a longer chain ketyl-CoA. In some embodiments, the at least one species of polyketide comprises at least one of olivetol, olivetolic acid, methyl-olivetol, or methyl-olivetolic acid.

In some embodiments, R2 is H and R3 is H.
In some embodiments, R2 is carboxyl and R3 is H.
In some embodiments, R2 is methyl and R3 is H.
In some embodiments, R2 is carboxyl and R3 is methyl
In some embodiments, the yeast cell comprises a genetic modification to increase available malonyl-CoA. In some embodiments, the genetic modification comprises increased expression of Maf1. In some embodiments, the yeast cell comprises a second polynucleotide including a coding sequence for Maf1 with a primary structure having between 80% and 100% amino acid residue sequence homology with a protein coded for by a reading frame defined by bases 936 to 2123 of SEQ ID NO: 6. In some embodiments, the second polynucleotide further comprises a promoter sequence, a terminator sequence and integration sequences, and has between 80% and 100% base sequence homology with SEQ ID NO: 6. In some embodiments, the genetic modification comprises cytosolic expression of an aldehyde dehydrogenase and an acetyl-CoA synthase. In some embodiments, the yeast cell comprises a second polynucleotide including a coding sequence for Acs$^{L641P}$ from *S. enterica* with a primary structure having between 80% and 100% amino acid residue sequence homology with a protein coded for by a reading frame defined by bases 3938 to 5893 of SEQ ID NO: 2, and a coding sequence for Ald6 from *S. cerevisiae* with a primary structure having between 80% and 100% amino acid residue sequence homology with a protein coded for by a reading frame defined by bases 1494 to 2999 of SEQ ID NO 2. In some embodiments, the second polynucleotide further comprises a promoter sequence, a terminator sequence and integration sequences, and has between 80% and 100% base sequence homology with bases 51 to 7114 SEQ ID NO: 2. In some embodiments, the genetic modification comprises increased expression of malonyl-CoA synthase. In some embodiments, the yeast cell comprises a second polynucleotide including a coding sequence for a coding sequence for $Acc1^{S659A;\ S1167A}$ from *S. cerevisiae*. In some embodiments, the second polynucleotide includes a coding sequence for the $Acc1^{S659A;\ S1167A}$ enzyme, with a portion thereof having a primary structure with between 80% and 100% amino acid residue sequence homology with a protein portion coded for by a reading frame defined by bases 9 to 1716 of SEQ ID NO: 5. In some embodiments, the second polynucleotide further comprises a promoter sequence, a terminator sequence and integration sequences, and has between 80% and 100% base sequence homology with SEQ ID NO: 5. In some embodiments, the genetic modification comprises increased expression of an activator for sterol biosynthesis. In some embodiments, the yeast cell comprises a second polynucleotide including a coding sequence for $Upc2^{E888D}$ from *S. cerevisiae* with a primary structure having between 80% and 100% amino acid residue sequence homology with a protein coded for by a reading frame defined by bases 975 to 3701 of SEQ ID NO: 7. In some embodiments, the second polynucleotide further comprises a promoter sequence, a terminator sequence and integration sequences, and has between 80% and 100% base sequence homology with SEQ ID NO: 7

In some embodiments, the method includes extracting the at least one species of polyketide from the yeast cell culture.

In a further aspect, herein provided is a yeast cell for producing at least one species of polyketide. The yeast cell includes a first polynucleotide coding for a polyketide synthase enzyme.

In some embodiments, features of one or more of the yeast cell, the first polynucleotide, or the second polynucleotide described herein are included in the yeast cell.

In a further aspect, herein provided is a method of transforming a yeast cell for production of at least one species of polyketide, the method comprising introducing a first polynucleotide coding for a polyketide synthase enzyme into the yeast cell line.

In some embodiments, features of one or more of the yeast cell, the first polynucleotide, or the second polynucleotide described herein are introduced into the yeast cell.

In a further aspect, herein provided is a method of producing a polyketide, the method comprising: providing a yeast cell comprising a first polynucleotide coding for a polyketide synthase enzyme and propagating the yeast cell for providing a yeast cell culture. The polyketide synthase enzyme is for producing at least one species of polyketide from malonyl-CoA, the polyketide having structure II:

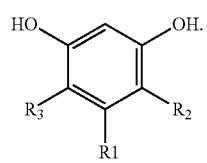

II

On structure II, R1 is an alkyl group having 1, 2, 3, 4 or 5 carbons. On structure II, R2 is H, carboxyl, or methyl. On structure II, R3 is H, carboxyl, or methyl.

In some embodiments, features of one or more of the yeast cell, the first polynucleotide, or the second polynucleotide described herein are applied to the method.

In a further aspect, herein provided is a polynucleotide comprising a coding sequence for a DiPKSG1516D; G1518A polyketide synthase. In some embodiments, the polynucleotide comprises a coding sequence for a DiPKSG1516D; G1518A polyketide synthase, wherein the DiPKSG1516D; G1518A polyketide synthase enzyme has a primary structure with between 80% and 100% amino acid residue sequence homology with a protein coded for by a reading frame defined by bases 523 to 9966 of SEQ ID NO: 9. In some embodiments, the polynucleotide has between 80% and 100% base sequence homology with bases 523 to 9966 of SEQ ID NO: 9.

In a further aspect, herein provided is a polynucleotide comprising a coding sequence for a $DiPKS^{G1516R}$ polyketide synthase. In some embodiments, the $DiPKS^{G1516R}$ polyketide synthase enzyme has a primary structure with between 80% and 100% amino acid residue sequence homology with a protein coded for by a reading frame defined by bases 523 to 9966 of SEQ ID NO: 10. In some embodiments, the polynucleotide has between 80% and 100% base sequence homology with bases 523 to 9966 of SEQ ID NO: 10.

In a further aspect, herein provided is a $DiPKS^{G1516D;\ G1518A}$ polyketide synthase with a primary structure having between 80% and 100% amino acid residue sequence homology with a protein coded for by a reading frame defined by bases 523 to 9966 of SEQ ID NO: 9.

In a further aspect, herein provided is a $DiPKS^{G1516R}$ polyketide synthase with a primary structure having between 80% and 100% amino acid residue sequence homology with a protein coded for by a reading frame defined by bases 523 to 9966 of SEQ ID NO: 10.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Generally, the present disclosure provides methods and yeast cell lines for producing olivetol similar to the olivetolic acid that is naturally biosynthesized in the *Cannabis sativa* plant, and for producing methyl-olivetol. The olivetol and methyl-olivetol may be produced in transgenic yeast. The methods and cell lines provided herein include application of genes for enzymes absent from the *C. sativa* plant. Compared with approaches that use *C. sativa* OAS and OAC, the methods and cell lines provided herein result in olivetol and methyl-olivetol being synthesized rather than olivetolic acid, which may provide one or more benefits including biosynthesis of decarboxylated phytocannabinoids, biosynthesis of methylated phytocannabinoid analogues, and biosynthesis production of phytocannabinoids without an input of hexanoic acid, which is toxic to *Saccharomyces cerevisiae* and other species of yeast.

The qualifier "decarboxylated" as used herein references a form of a phytocannabinoid or phytocannabinoid analogue lacking an acid group at, e.g. positions 2 or 4 of Δ9-tetrahydrocannabinol ("THC"), or an equivalent location in other phytocannabinoids or analogues corresponding to position 4 of olivetolic acid, which is the precursor to biosynthesis of CBGa in *C. sativa*. Acid forms of phytocannabinoids are biosynthesized from olivetolic acid in *C. sativa*. When the acid forms of phytocannabinoids are heated, the bond between the aromatic ring of the phytocannabinoid and the carboxyl group is broken. Decarboxylation results from heating carboxylated phytocannabinoids produced in *C. sativa*, which occurs rapidly during combustion or heating to temperatures generally above about 110° C. For simplicity, as used herein, "decarboxylated" refers to phytocannabinoids lacking the acid groups whether or not the phytocannabinoid included an acid group that was lost during true decarboxylation, or was biosynthesized without the carboxyl group.

Figure 1:
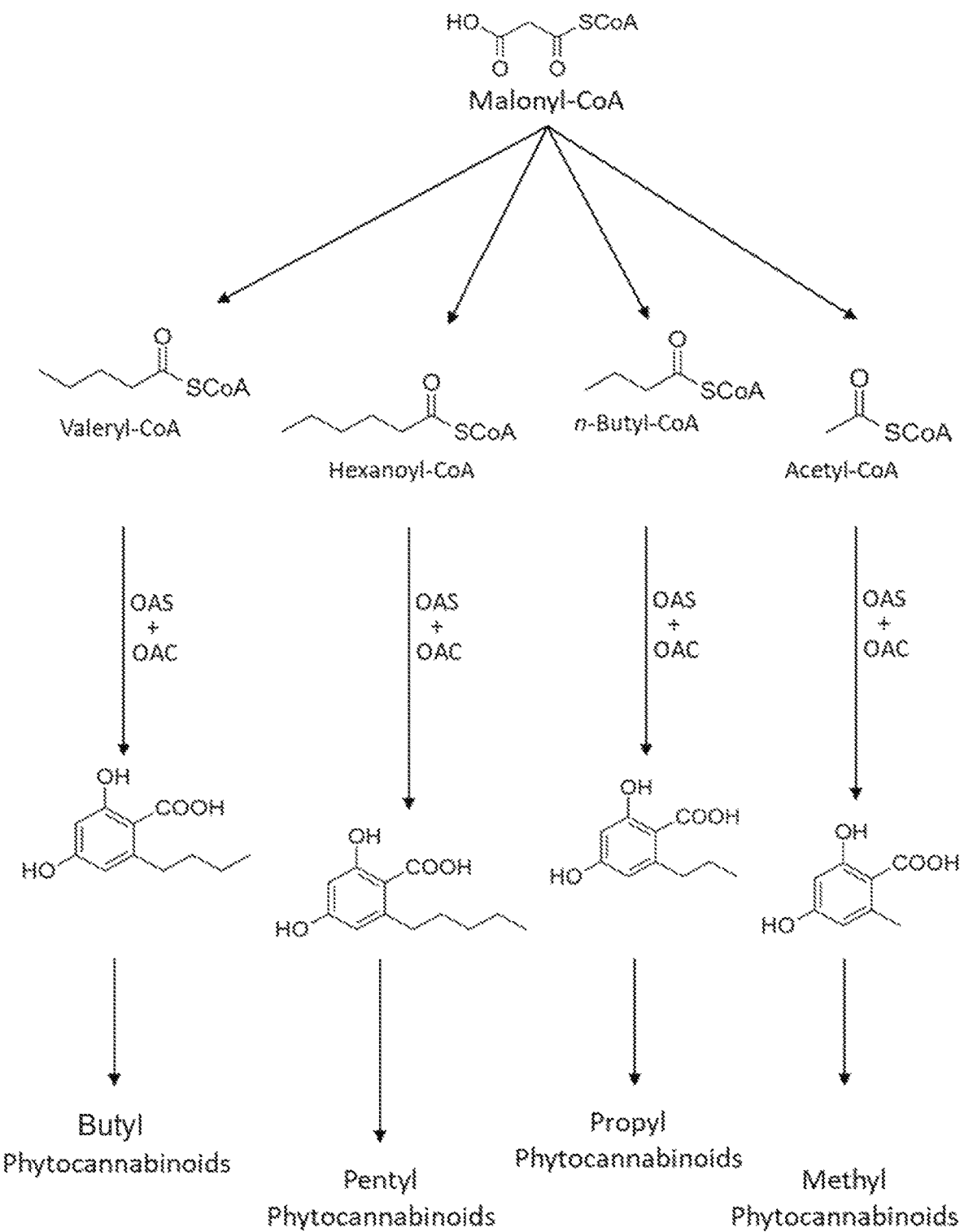
FIG. 1 is a schematic of biosynthesis of olivetolic acid and related compounds with different alkyl group chain lengths in *C. sativa*.

FIG. 1 shows biosynthesis of olivetolic acid from polyketide condensation products of malonyl-CoA and hexanoyl-CoA, as occurs in in *C. sativa*. Olivetolic acid is a metabolic precursor to CBGa. CBGa is a precursor to a large number of downstream phytocannabinoids as described in further detail below. In most varieties of *C. sativa*, the majority of phytocannabinoids are pentyl-cannabinoids, which are biosynthesized from olivetolic acid, which is in turn synthesized from malonyl-CoA and hexanoyl-CoA at a 2:1 stoichiometric ratio. Some propyl-cannabinoids are observed, and are often identified with a "v" suffix in the widely-used three letter abbreviations (e.g. tetrahydrocannabivarin is commonly referred to as "THCv", cannabidivarin is commonly referred to as "CBDv", etc.). FIG. 1 also shows biosynthesis of divarinolic acid from condensation of malonyl-CoA with n-butyl-CoA, which would provide downstream propyl-phytocannabinoids.

FIG. 1 also shows biosynthesis of orsellinic acid from condensation of malonyl-CoA with acetyl-CoA, which would provide downstream methyl-phytocannabinoids. The term "methyl-phytocannabinoids" in this context means their alkyl side chain is a methyl group, where most phytocannabinoids have a pentyl group on the alkyl side chain and varinnic phytocannabinoids have a propyl group on the alkyl side chain. The context in which meCBG and other methylated phytocannabinoid analogues are called "methylated" is different from and parallel to use of "methyl" as a prefix in "methyl-phytocannabinoids" and in FIG. 1. Similarly, since olivetol has a side chain of defined length (otherwise it would be one of the other three polyketides shown in FIG. 1 and not "olivetol"), methyl-olivetol is a reference to methylation on the ring and not to a shorter side chain.

FIG. 1 also shows biosynthesis of 2,4-diol-6-propylbenzenoic acid from condensation of malonyl-CoA with valeryl-CoA, which would provide downstream butyl-phytocannabinoids.

Figure 2:
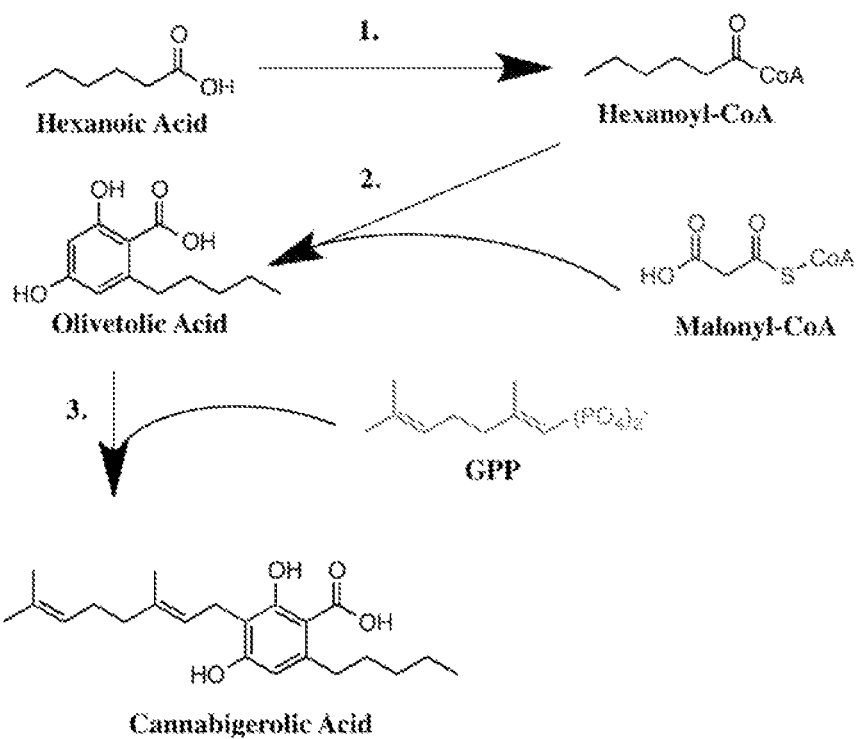
FIG. 2 is a schematic of biosynthesis of CBGa from hexanoic acid, malonyl-CoA, and geranyl pyrophosphate in *C. sativa*.

FIG. 2 shows biosynthesis of CBGa from hexanoic acid, malonyl-CoA, and geranyl pyrophosphate ("GPP") in *C. sativa*, including the olivetolic acid biosynthesis step shown in FIG. 1. Hexanoic acid is activated with coenzyme A by hexanoyl-CoA synthase ("Hex1; Reaction 1 in FIG. 2). Polyketide synthase (also called olivetolic acid synthase "OAS" despite synthesizing olivetol and not olivetolic acid) and OAC together catalyze production of olivetolic acid from hexanoyl CoA and malonyl-CoA (Reaction 2 in FIG. 2). Prenyltransferase combines olivetolic acid with GPP, providing CBGa Step 3 in FIG. 2).

Figure 3:
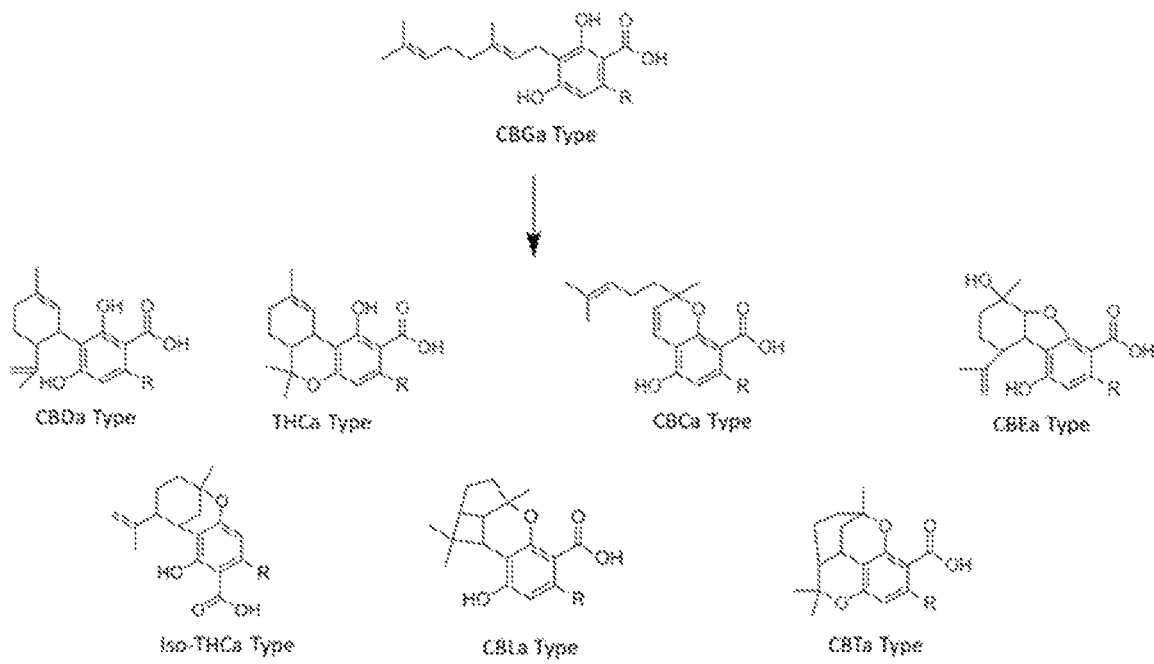
FIG. 3 is a schematic of biosynthesis of downstream phytocannabinoids in the acid form from CBGa in *C. sativa*.

FIG. 3 shows biosynthesis of downstream acid forms of phytocannabinoids in *C. sativa* from CBGa. CBGa is oxidatively cyclized into Δ9-tetrahydrocannabinolic acid ("THCa") by THCa synthase. CBGa is oxidatively cyclized into cannabidiolic acid ("CBDa") by CBDa synthase. Other phytocannabinoids are also synthesized in *C. sativa*, such as cannabichromenic acid ("CBCa"), cannabielsoinic acid ("CBEa"), iso-tetrahydrocannabinolic acid ("iso-THCa"), cannabicyclolic acid ("CBLa"), or cannabicitrannic acid ("CBTa") by other synthase enzymes, or by changing conditions in the plant cells in a way that affects the enzymatic activity in terms of the resulting phytocannabinoid structure. The acid forms of each of these general phytocannabinoid types are shown in FIG. 3 with a general "R" group to show the alkyl side chain, which would be a 5-carbon chain where olivetolic acid is synthesized from hexanoyl-CoA and malonyl-CoA. In some cases, the carboxyl group is alternatively found on a ring position opposite the R group from the position shown in FIG. 3 (e.g. positions 4 of THC rather than position 2 as shown in FIG. 3, etc.). The decarboxylated forms of the acid forms of the phytocannabinoids shown in FIG. 3 are, respectively, THC, cannabidiol ("CBD"), cannabichromene ("CBC"), cannabielsoin ("CBE"), iso-tetrahydrocannabinol ("iso-THC"), cannabicyclol ("CBL"), or cannabicitran ("CBT").

Figure 4:
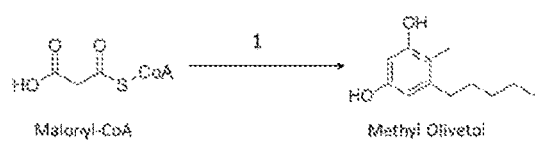
FIG. 4 is a schematic of biosynthesis of olivetolic acid in a transformed yeast cell by DiPKS.

FIG. 4 shows a biosynthetic pathway in transgenic yeast for production of methyl-olivetol from malonyl-CoA. A strain of yeast as provided herein for producing methyl-olivetol as shown in FIG. 4 may include the DiPKS enzyme, which supports production of polyketides from malonyl-CoA only, with no requirement for hexanoic acid from the media. As above, DiPKS includes functional domains similar to domains found in a fatty acid synthase, a methyltransferase domain, and a Pks III domain (see FIG. 7), and is accordingly referred to as a FAS-PKS enzyme. Examples of yeast strains including a codon optimized synthetic sequence coding for the wildtype DiPKS gene are provided as "HB80" and "HB98", each of which are described in Table 3.

Figure 5:
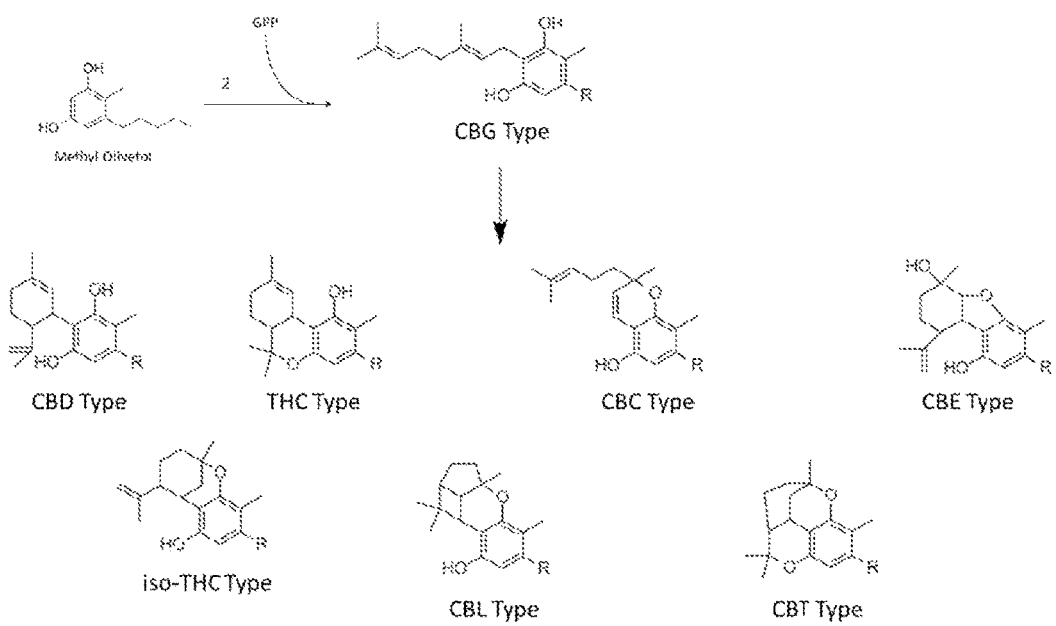
FIG. 5 is a schematic of biosynthesis of meCBG and downstream methylated phytocannabinoid analogues in a transformed yeast cell from methyl-olivetol.
Figure 6:
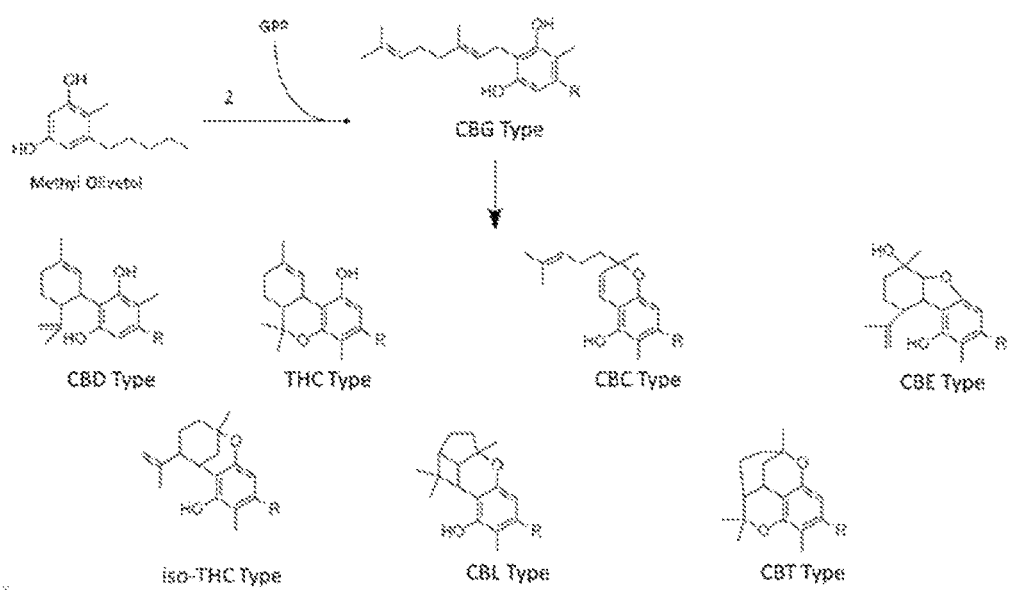
FIG. 6 is a schematic of biosynthesis of meCBG and downstream methylated phytocannabinoid analogues in a transformed yeast cell from methyl-olivetol.

FIGS. 5 and 6 show prenylation of the methyl-olivetol with GPP as a prenyl group donor, providing meCBG (Reaction 2 in FIGS. 5 and 6, following Reaction 1 from FIG. 4). Application of DiPKS rather than OAS facilitates production of phytocannabinoids and phytocannabinoid analogues without hexanoic acid supplementation. Since hexanoic acid is toxic to S. cerevisiae, eliminating a requirement for hexanoic acid in the biosynthetic pathway for CBG or meCBG may provide greater yields of CBG or meCBG than the yields of CBG in a yeast cell expressing OAS and Hex1.

FIGS. 5 and 6 show downstream methylated phytocannabinoid analogues corresponding to methyl-tetrahydrocannabinol ("meTHC"), methyl-cannabidiol ("meCBD"), methyl-cannabichromene ("meCBC"), methyl-cannabielsoin ("meCBE"), iso-methyl-tetrahydrocannabinol ("iso-meTHC"), methyl-cannabicyclol ("meCBL"), or methyl-cannabicitran ("meCBT"), which are methylated analogues of THC, CBD, CBC, CBE, iso-THC, CBL, and CBT, respectively, that may be prepared when methyl-olivetol is provided as a precursor chemical rather than olivetolic acid or olivetol. The decarboxylated forms of each of these methylated phytocannabinoid analogues are shown in FIGS. 5 and 6 with a general "R" group to show the alkyl side chain, which would be a 5-carbon chain where synthesis results from hexanoyl-CoA and malonyl-CoA, or malonyl-CoA only.

Other than meCBD, a portion of the structure each of the downstream phytocannabinoid anaologues shown in FIGS. 5 and 6 includes rotationally constrained groups bonded with the aromatic ring. As a result, each of the downstream phytocannabinoid analogues shown in FIGS. 5 and 6 other than meCBD may be synthesized from meCBG in one of two rotational isomers. Depending on the rotational isomer of meCBG during synthesis, the methyl group in the resulting cyclized methylated phytocannabinoid analogues may be at the positions shown for the isomers of meTHC, meCBC, meCBE, iso-meTHC, meCBL, or meCBT in FIG. 5, or at the at the positions shown for the isomers of meTHC, meCBC, meCBE, iso-meTHC, meCBL, or meCBT in FIG. 6. References to meTHC, meCBC, meCBE, iso-meTHC, meCBL, or meCBT herein include either or both of the isomers shown in FIGS. 5 and 6.

DiPKS includes a C-methyltransferase domain that methylates olivetol at position 4 on the aromatic ring. As a result, any downstream prenylation would be of methyl-olivetol, resulting in meCBG, a phytocannabinoid analogue, rather than CBGa, which is known to be synthesized in C. sativa. Any downstream reactions that may produce phytocannabinoids when using CBGa or CBG as an input would correspondingly produce the decarboxylated species of methylated phytocannabinoid analogues shown in FIGS. 5 and 6, whereas unmethylated acid form of phytocannabinoids would be produced in C. sativa (as in FIG. 3). If OAC or another polyketide cyclase were included, the methyl-olivetol may be converted by the OAC or the other polyketide cyclase into meCBGa, as the methylation and carboxylation carbons may be at differing positions. For example, meTHC synthesized from meCBG may be methylated at carbon 4, and could be carboxylated to methyl-tetrahydrocannabinolic acid ("meTHCa") with the carboxyl group of THCa may be at position 2. Alternatively, meTHC synthesized from meCBG may be methylated at carbon 2, in which case the carboxyl group of THCa may be at position 4. THCa is observed in C. sativa with the carboxyl group at the 2 position, or at the 4 position.

Figure 7:
FIG. 7 is a schematic of functional domains in DiPKS, with mutations to a C-methyl transferase that for lowering methylation of olivetol.

FIG. 7 is a schematic of the functional domains of DiPKS showing β-ketoacyl-synthase ("KS"), acyl transacetylase ("AT"), dehydratase ("DH"), C-methyl transferase ("C-Met"), enoyl reductase ("ER"), ketoreductase ("KR"), and acyl carrier protein ("ACP"). The "Type III" domain is a type 3 polyketide synthase. The KS, AT, DH, ER, KR, and ACP portions provide functions typically associated with a fatty acid synthase. The C-Met domain provides the catalytic activity for methylating olivetol at carbon 4. The C-Met domain is crossed out in FIG. 7, schematically illustrating modifications to DiPKS protein that inactivate the C-Met domain and mitigate or eliminate methylation functionality. The Type III domain catalyzes iterative polyketide extension and cyclization of a hexanoic acid thioester transferred to the Type III domain from the ACP.

Figure 8:
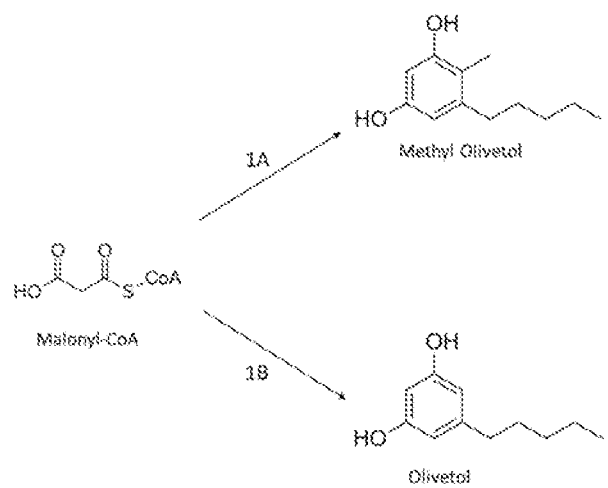
FIG. 8 is a schematic of biosynthesis of methyl-olivetol and olivetol in a transformed yeast cell by DiPKS$^{G1516D;\ G1518A}$.

FIG. 8 shows a biosynthetic pathway in transgenic yeast for production of both meCBG and CBG from malonyl-CoA and GPP. A strain of yeast as provided herein for producing both CBG and meCBG as shown in FIG. 8 may include the gene for a prenyltransferase and a gene for a mutant DiPKS with a lowered activity at the C-Met domain, as shown schematically in FIG. 7. The C-Met domain of the DiPKS protein includes amino acid residues 1510 to 1633 of DiPKS. The C-Met domain includes three motifs. The first motif includes residues 1510 to 1518. The second motif includes residues 1596 to 1603. The third motif includes residues 1623 to 1633. Disruption of one or more of these three motifs may result in lowered activity at the C-Met domain.

An example of a yeast strain expressing a modified DiPKS with lowered activity in the C-Met domain is provided as "HB80A" in Example III below. HB80A includes a modification in a yeast-codon optimized gene coding for the wildtype DiPKS protein. HB80A includes modifications in the DiPKS gene such that the DiPKS protein is modified in the first motif of the C-Met domain. As a result of these modifications to the DiPKS gene, the DiPKS protein has substitutions of Gly1516Asp and Gly1518Ala. HB80A includes DiPKS$^{G1516D;\ G1518A}$, and as a result catalyzes both step 1A and 1B of FIG. 8, and produces both methyl-olivetol and olivetol.

FIG. 8 shows production of both methyl-olivetol from malonyl-CoA (Reaction 1A in FIG. 8) and of olivetol from malonyl-CoA (Reaction 1B in FIG. 8). Reactions 1A and 1B are each catalyzed by DiPKS$^{G1516D;\ G1518A}$. The Gly1516Asp and Gly1518Ala substitutions are in the active site of the C-Met domain and diminish catalysis by DiPKS$^{G1516D;\ G1518A}$ of methylation on the 4 position of the olivetol ring, allowing a portion of the input malonyl-CoA to be catalyzed according to reaction 1B rather than reaction 1A. A promiscuous αββα prenyltransferase could then catalyze prenylation of both the methyl-olivetol with GPP and the olivetol with GPP, resulting in production of both meCBG (Reaction 2 in FIGS. 5 and 6) and CBG through prenylation of olivetol, similar to reaction 3 in FIG. 2 but without the acid group. Any downstream reactions to produce other phytocannabinoids would then correspondingly produce a mixture of methylated phytocannabinoid analogues and species with no functional group at the 4 position on the aromatic ring of CBG (or a corresponding position in downstream phytocannabinoids), whereas acid forms would be produced in *C. sativa*.

Figure 9:
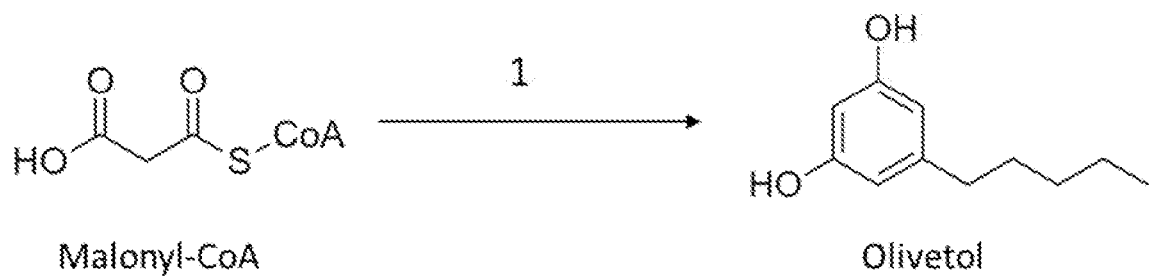
FIG. 9 is a schematic of biosynthesis of olivetol in a transformed yeast cell by DiPKS$^{G1516R}$.

FIG. 9 shows a biosynthetic pathway in transgenic yeast for production of olivetol only, and no methyl-olivetol, from malonyl-CoA. A strain of yeast as provided herein for producing olivetol only as shown in FIG. 9 may include the gene for a mutant DiPKS with a lowered activity at the C-Met domain, as shown schematically in FIG. 7.

Examples of yeast strains expressing a modified DiPKS with essentially no activity in the C-Met domain are provided as "HB135", "HB137", and "HB138" in Examples VI and VII below. Each of HB135, HB137 and HB138 includes a modification in a yeast-codon optimized gene coding for the wildtype DiPKS protein. HB135, HB137 and HB138 each include a modification of the DiPKS gene such that the DiPKS protein is modified in the first motif of the C-Met domain. As a result of this modification to the DiPKS gene, the DiPKS protein has substitutions of Gly1516Arg.

DiPKS$^{G1516R}$ catalyzes reaction 1 in FIG. 9. The Gly1516Arg substitution is in the active site of the C-Met domain and diminish catalysis by DiPKS$^{G1516R}$ of methylation on the 4 position of the olivetol ring. The input of malonyl-CoA is catalyzed according to reaction 1 of FIG. 9. Any downstream reactions to produce other phytocannabinoids would then correspondingly produce phytocannabinoid species with no functional group at the 4 position on the aromatic ring of CBG, or a corresponding position in downstream phytocannabinoids, whereas acid forms would be produced in *C. sativa*.

Increasing Availability of Biosynthetic Precursors

The biosynthetic pathways shown in FIGS. 4, 8 and 9 each require malonyl-CoA to produce methyl-olivetol only, both methyl-olivetol and olivetol, and olivetol only, respectively. Yeast cells may be mutated, genes from other species may be introduced, genes may be upregulated or downregulated, or the yeast cells may be otherwise genetically modified to increase the availability of malonyl-CoA or other input metabolites required to support the biosynthetic pathways of any of FIG. 4, 8 or 9.

The yeast strain may be modified for increasing available malonyl-CoA. Lowered mitochondrial acetaldehyde catabolism results in diversion of the acetaldehyde from ethanol catabolism into acetyl-CoA production, which in turn drives production of malonyl-CoA and downstream polyketides and terpenoids. *S. cerevisiae* may be modified to express an acetyl-CoA synthase from *Salmonella enterica* with a substitution modification of Leucine to Proline at residue 641 ("Acs$^{L641P}$") and with aldehyde dehydrogenase 6 from *S. cerevisiae* ("Ald6"). The Leu641Pro mutation removes downstream regulation of Acs, providing greater activity with the Acs$^{L641P}$ mutant than the wild type Acs. Together, cytosolic expression of these two enzymes increases the concentration of acetyl-CoA in the cytosol. Greater acetyl-CoA concentrations in the cytosol result in lowered mitochondrial catabolism, bypassing mitochondrial pyruvate dehydrogenase ("PDH"), providing a PDH bypass. As a result, more acetyl-CoA is available for malonyl-CoA production. SEQ ID NO: 2 is plasmid based on the pGREG plasmid and including a DNA sequence coding for the genes for Ald6 and SeAcs$^{L641P}$, promoters, terminators, and integration site homology sequences for integration into the *S. cerevisiae* genome at Flagfeldt-site 19 by recombination applying clustered regularly interspaced short palindromic repeats ("CRISPR"). As shown in Table 2 below (by the term "PDH bypass"), each of base strains "HB82", "HB100", "HB106", and "HB110". have a portion of SEQ ID NO: 2 from bases 1494 to 2999 that code for Ald6 under the TDH$_3$ promoter, and a portion of SEQ ID NO: 2 from bases 3948 to 5893 that code for SeAcs$^{L641P}$ under the Tef1$_P$ promoter. Similarly, each modified yeast strain based on any of HB82, HB100, HB106, or HB110 includes a polynucleotide coding for Ald6 and SeAcs$^{L641P}$.

Another approach to increasing cytosolic malonyl-CoA is to upregulate Acc1, which is the native yeast malonyl-CoA synthase. The promoter sequence of the Acc1 gene was replaced by a constitutive yeast promoter for the PGK1 gene. The promoter from the PGK1 gene allows multiple copies of Acc1 to be present in the cell. The native Acc1 promoter allows only a single copy of the protein to be present in the cell at a time. The native promoter region was marked is shown in SEQ ID NO: 3. The modified promoter region is shown in SEQ ID NO: 4.

In addition to upregulating expression of Acc1, *S. cerevisiae* may include one or more modifications of Acc1 to increase Acc1 activity and cytosolic acetyl-CoA concentrations. Two mutations in regulatory sequences were identified in literature that remove repression of Acc1, resulting in greater Acc1 expression and higher malonyl-CoA production. SEQ ID NO: 5 is a polynucleotide that may be used to modify the *S. cerevisiae* genome at the native Acc1 gene by homologous recombination. SEQ ID NO: 5 includes a portion of the coding sequence for the Acc1 gene with Ser659Ala and Ser1167Ala modifications. As a result, the *S. cerevisiae* transformed with this sequence will express Acc1$^{S659A;\ S1167A}$. A similar result may be achieved, for example, by integrating a sequence with the Tef1 promoter, the Acc1 with Ser659Ala and Ser1167Ala modifications, and the Prm9 terminator at any suitable site. The end result would be that Tef1, Acc1$^{S659A;\ S1167A}$, and Prm9 are flanked by genomic DNA sequences for promoting integration into the *S. cerevisiae* genome. This was attempted at Flagfeldt site 18 but due to the size of the construct, the approach with SEQ ID NO: 5 described above was followed instead.

*S. cerevisiae* may include modified expression of Maf1 or other regulators of tRNA biosynthesis. Overexpressing native Maf1 has been shown to reduce loss of IPP to tRNA biosynthesis and thereby improve monoterpene yields in yeast. IPP is an intermediate in the mevalonate pathway. SEQ ID NO: 6 is a polynucleotide that was integrated into the *S. cerevisiae* genome at Maf1-site 5 for genomic integration of Maf1 under the Tef1 promoter. SEQ ID NO: 6 includes the Tef1 promoter, the native Maf1 gene, and the Prm9 terminator. Together, Tef1, Maf1, and Prm9 are flanked by genomic DNA sequences for promoting integration into the *S. cerevisiae* genome. As shown in Table 2 below, base strains HB100, HB106, and HB110 express Maf1 under the Tef1 promoter. Similarly, each modified yeast strain based on any of HB100, HB106, or HB110 includes a polynucleotide including a coding sequence for Maf1 under the Tef1 promoter.

Upc2 is an activator for sterol biosynthesis in *S. cerevisiae*. A Glu888Asp mutation of Upc2 increases monoterpene production in yeast. SEQ ID NO: 7 is a polynucleotide that may be integrated into the genome to provide expression of Upc2$^{E888D}$ under the Tef1 promoter. SEQ ID NO: 7 includes the Tef1 promoter, the Upc2$^{E888D}$ gene, and the Prm9 terminator. Together, Tef1, Upc2$^{E888D}$, and Prm9 are flanked by genomic DNA sequences for promoting integration into the *S. cerevisiae* genome.

Any of the above genes, Acs$^{L641P}$, Ald6, Maf1, Acc1$^{S659A;\ S1167A}$ or Upc2$^{E888D}$, may be expressed from a plasmid or integrated into the genome of *S. cerevisiae*. Genome integration may be through homologous recombination, including CRISPR recombination, or any suitable approach. The promoter of Acc1 may be similarly modified through recombination. The coding and regulatory sequences in each of SEQ ID NO: 2, SEQ ID NO: 4, SEQ ID NO: 5, SEQ ID NO: 6, or SEQ ID NO: 7 may be included in a plasmid for expression (e.g. pYES, etc.) or a linear polynucleotide for integration into the *S. Cerevisiae* genome. Each of base strains HB82, HB100, HB106, or HB110 includes one or more integrated SEQ ID NO: 2, SEQ ID NO: 4, SEQ ID NO: 6, or SEQ ID NO: 8 (see Table 2 below). Integration of SEQ ID NO: 5, or SEQ ID NO: 7 may be applied by similar approaches.

Increased DiPKS Function

As shown in FIG. 7, DiPKS includes an ACP domain. The ACP domain of DiPKS requires a phosphopantetheine group as a co-factor. NpgA is a 4'-phosphopantethienyl transferase from *Aspergillus nidulans*. A codon-optimized copy of NpgA for *S. cerevisiae* may be introduced into *S. cerevisiae* and transformed into the *S. cerevisiae*, including by homologous recombination. An NpgA gene cassette was integrated into the genome of *Saccharomyces cerevisiae* at Flagfeldt site 14 to create strain HB100. The sequence of the integrated DNA is shown in SEQ ID NO: 8, and includes the Tef1 Promoter, the NpgA coding sequence and the Prm9 terminator. Together the Tef1p, NpgA, and Prm9t are flanked by genomic DNA sequences promoting integration into Flagfeldt site 14 in the *S. cerevisiae* genome. As shown in Table 2 below, base strains HB100, HB106, and HB110 include this integrated cassette. Alternatively, bases 636 to 2782 of SEQ ID NO: 8 may be included on an expression plasmid as in strain HB98.

Expression of NpgA provides the *A. nidulans* phosphopantetheinyl transferase for greater catalysis of loading the phosphopantetheine group onto the ACP domain of DiPKS. As a result, the reaction catalyzed by DiPKS (reaction 1 in FIG. 4) may occur at greater rate, providing a greater amount of methyl-olivetol.

Modification of DiPKS

DiPKS may be modified to reduce or eliminate the activity of C-Met.

SEQ ID NO: 9 is a modified form of a synthetic sequence for DIPKS that is codon optimized for yeast in which DiPKS includes a Gly1516Asp substitution and a Gly1518Ala substitution that together disrupt the activity of the C-met domain. Results of DiPKS$^{G1516D, G1518A}$ expression in *S. cerevisiae* cultures are provided below in relation to Example II, which includes strain HB80A. Other modifications may be introduced into DiPKS to disrupt or eliminate the entire active site of C-Met or all of C-Met. Each of these modified DiPKS enzymes may be introduced into *S. cerevisiae* as described for wild type DiPKS.

SEQ ID NO: 10 is a modified form of a synthetic sequence for DIPKS that is codon optimized for yeast in which DiPKS includes a Gly1516Arg substitution that disrupts the activity of the C-met domain. Results of DiPKSG$^{1516}$R expression in *S. cerevisiae* cultures are provided below in relation to Example VI, which includes strain HB135 and Example VII, which includes strains HB135, HB137 and HB138.

In addition to DiPKS$^{G1516D, G1518A}$ and DiPKS$^{G1516R}$ specifically, other modifications were introduced into DiPKS to disrupt or eliminate the entire active site of C-Met or all of C-Met: (a) substitution of motif 1 with GGGSGGGSG, (b) a Gly1516Arg substitution in motif 1 and substitution of motif 2 with GGGSGGGS, (c). a Glu1634Ala, which is just outside motif 3 and disrupts tertiary structure at an active site in the C-Met domain, and (d). disruption of an active site in the C-Met domain by a His1608Gln substitution. Codon optimized sequences for each of (a) to (d) were introduced into yeast on expression plasmids, similarly to expression of DiPKS$^{G1516D, G1518A}$ and DiPKSG$^{1516}$R, into base strain HB100. In each case, no production of olivetol was observed. Substitution of either motif 1 or motif 2 with GGGSGGGS eliminated production of methyl-olivetol as well. A culture of yeast expressing the DiPKSG$^{1634}$A mutant provided 2.67 mg methyl-olivetol per l of culture in one example batch. A culture of yeast expressing the DiPKS$^{H1608N}$ mutants provided 3.19 mg methyl-olivetol per l of culture in one example batch.

Transforming and Growing Yeast Cells

Details of specific examples of methods carried out and yeast cells produced in accordance with this description are provided below as Examples I to VII. Each of these seven specific examples applied similar approaches to plasmid construction, transformation of yeast, quantification of strain growth, and quantification of intracellular metabolites. These common features across the seven examples are described below, followed by results and other details relating to one or more of the seven examples.

Plasmid Construction

Plasmids assembled to apply and prepare examples of the methods and yeast cells provided herein are shown in Table 1. In Table 1, for the expression plasmids pYES, and pYES2, SEQ ID NOs 11 and 12 respectively provide the plasmids as a whole without an expression cassette. The expression cassettes of SEQ ID NOs: 8 to 10, 13 and 14 can be included in to prepare the plasmids indicated in Table 1. SEQ ID NO: 2 is the pGREG plasmid including a cassette for the PDH bypass genes.

TABLE 1

Plasmids and Cassettes Used to Prepare Yeast Strains

| Plasmid | Cassette | Description |
|---|---|---|
| pYES | (none) | LEU auxotroph; ampicillin resistance; SEQ ID NO: 11 |
| pYES2 | (none) | URA auxotroph; ampicillin resistance; SEQ ID NO: 12 |
| pPDH | Bases 1 to 7214 from SEQ ID NO: 2 | High copy amplification plasmid with PDH Bypass genes for acetaldehyde dehydrogenase (Ald6) and acetyl-CoA synthase (Acs$^{L641P}$) assembled in pGREG 505/G418 flanked by integration site homology sequences as follows: C1-506-BclV-Site 19 UP region-L0 L0-TDH3$_P$-L1-Ald6-L2-Adh1$_T$-LTP1 LTP1-Tef1$_P$-L3- Acs$^{L641P}$-L4-Prm9$_T$-LTP2 LTP2-Site 19 down region-C6-506 |
| pNPGa | SEQ ID NO: 8 | High copy NpgA expression plasmid in pYES2 with: LV3-Tef1$_P$-L1-NpgA-L2-Prm9$_T$-LV5 |

TABLE 1-continued

Plasmids and Cassettes Used to Prepare Yeast Strains

| Plasmid | Cassette | Description |
| --- | --- | --- |
| pDiPKSm1 | SEQ ID NO: 9 | High copy DiPKS$^{G1516D;\ G1518A}$ expression plasmid in pYES2 with: LV3-Gal1-L1-DiPKS$^{G1516D;\ G1518A}$-L2-Prm9$_T$-LV5 |
| pDiPKSm2 | SEQ ID NO: 10 | High copy DIPKS$^{G1516R}$ expression plasmid in pYES2 with: LV3-Gal1-L1-DiPKS$^{G1516R}$-L2-Prm9t$_T$-LV5 |
| pDiPKS | SEQ ID NO: 13 | High copy DiPKS expression plasmid in pYES2 with: LV3-Gal1-L1-DiPKS-L2-Prm9$_T$-LV5 |
| pCRISPR | SEQ ID NO: 14 | High copy Cas9 endonuclease and targeted gRNA expression plasmid in pYES2 with: LV3-Tef1$_P$-Cas9-Adh1$_T$-LTP1 LTP1-gRNA-LV5 |

Plasmids for introduction into *S. cerevisiae* were amplified by polymerase chain reaction ("PCR") with primers from Operon Eurofins and Phusion HF polymerase (ThermoFisher F-530S) according to the manufacturer's recommended protocols using an Eppendorf Mastercycler ep Gradient 5341.

All plasmids were assembled using overlapping DNA parts and transformation assisted recombination in *S. cerevisiae*. The plasmids were transformed into *S. cerevisiae* using the lithium acetate heat shock method as described by Gietz, R. D. and Schiestl, R. H., "High-efficiency yeast transformation using the LiAc/SS carrier DNA/PEG method." *Nat. Protoc.* 2, 31-34 (2007). The pNPGa, pDiPKSm1, pDiPKSm2, pCRISPR, pDiPKS, and pPDH plasmids were assembled yeast strain HB25, which is a uracil auxotroph. Transformed *S. cerevisiae* cells were selected by auxotrophic selection on agar petri dishes. Colonies recovered from the petri dishes were grown up in liquid selective media for 16 hrs at 30° C. while being shaken at 250 RPM.

After growth in liquid selective media, the transformed *S. cerevisiae* cells were collected and the plasmid DNA was extracted. The extracted plasmid DNA was transformed into *Escherichia coli*. Transformed *E. coli* were selected for by growing on agar petri dishes including ampicillin. The *E. coli* were cultured to amplify the plasmid. The plasmid grown in the *E. coli* was extracted and sequenced with Sanger dideoxy sequencing to verify accurate construction. The sequence-verified plasmid was then used for genome modification or stable transformation of the *S. cerevisiae*.

Genome Modification of *S. cerevisiae*

The *S. cerevisiae* strains described herein may be prepared by stable transformation of plasmids or genome modification. Genome modification may be accomplished through homologous recombination, including by methods leveraging CRISPR.

Methods applying CRISPR were applied to delete DNA from the *S. cerevisiae* genome and introduce heterologous DNA into the *S. cerevisiae* genome. Guide RNA ("gRNA") sequences for targeting the Cas9 endonuclease to the desired locations on the *S. cerevisiae* genome were designed with Benchling online DNA editing software. DNA splicing by overlap extension ("SOEing") and PCR were applied to assemble the gRNA sequences and amplify a DNA sequence including a functional gRNA cassette.

The functional gRNA cassette, a Cas9-expressing gene cassette, and the pYes2 (URA) plasmid were assembled into the pCRISPR plasmid and transformed into *S. cerevisiae* for facilitating targeted DNA double-stranded cleavage. The resulting DNA cleavage was repaired by the addition of a linear fragment of target DNA.

Genome modification of *S. cerevisiae* was based on strain HB42, which is a Uracil auxotroph based in turn on strain HB25, and which includes an integration of the CDS for an Erg20$^{K197}$ E protein. This integration was for other purposes not directly relevant to production of methyl-olivetol or olivetol, but which may be useful when also synthesizing CBG or meCBG, which requires GPP. The Erg20$^{K197E}$ mutant protein increases GPP levels in the cell.

Bases 51 to 7114 of SEQ ID NO: 2 were integrated into the HB42 strain by CRISPR to provide the HB82 base strain with the PDH bypass genes in *S. cerevisiae*. The pPDH plasmid was sequence verified after assembly in *S. cerevisiae*. The sequence-verified pPDH plasmid was grown in *E. coli*, purified, and digested with BciV1 restriction enzymes. As in Table 1, digestion by BciV1 provided a polynucleotide including the genes for Ald6 and SeAcs$^{L641P}$, promoters, terminators, and integration site homology sequences for integration into the *S. cerevisiae* genome at PDH-site 19 by Cas9. The resulting linear PDH bypass donor polynucleotide, shown in bases 51 to 7114 of SEQ ID NO: 2, was purified by gel separation.

With both PDH bypass genes (Ald6 and Acs$^{L641P}$) on the single PDH bypass polynucleotide, the PDH bypass donor polynucleotide was co-tranformed into *S. cerevisiae* with pCRISPR. Transformation was by the lithium acetate heat shock method as described by Gietz. The pCRISPR plasmid expresses Cas9, which is targeted to a selected location of *S. cerevisiae* the genome by a gRNA molecule. At the location, the Cas9 protein creates a double stranded break in the DNA. The PDH bypass donor polynucleotide was used as a donor polynucleotide in the CRISPR reaction. The PDH bypass donor polynucleotide including Ald6, Acs$^{L641P}$, promoters, and terminators was integrated into the genome at the site of the break, Site 19, by homologous recombination, resulting in strain HB82.

The NpgA donor polynucleotide shown in SEQ ID NO: 8 was prepared and amplified. DNA SOEing was used to create a single donor DNA fragment from three polynucleotides for NpgA integration. The first polynucleotide was the 5' region of genomic homology that allows the donor to recombine into the genome at a specific locus. The second polynucleotide coded for the NpgA gene cassette. The NpgA gene cassette includes the Tef1 promoter, the NpgA coding sequence and the Prm9 terminator. The third polynucleotide included the 3' region for genomic homology to facilitate targeted integration into the S. cerevisiae genome.

The NpgA donor polynucleotide was co-transformed with the pCRISPR plasmid into strain HB82. The pCRISPR plasmid was expressed and endonuclease Cas9 was targeted to a location on the S. cerevisiae genome by a gRNA molecule. At the location, the Cas9 protein created a double stranded break in the DNA and the NpgA donor polynucleotide was integrated into the genome at the break by homologous recombination to provide the HB100 base strain.

The Maf1 donor polynucleotide shown in SEQ ID NO: 6 was prepared and amplified. DNA SOEing was used to create a single donor DNA fragment from three polynucleotides for Maf1 integration. The first polynucleotide was the 5' region of genomic homology that allows the donor to recombine into the genome at a specific locus. The second polynucleotide coded for the Maf1 gene cassette. The Maf1 gene cassette includes the Tef1 promoter, the Maf1 coding sequence and the Prm9 terminator. The third polynucleotide included the 3' region for genomic homology to facilitate targeted integration into the S. cerevisiae genome.

The Maf1 donor polynucleotide was co-transformed with the pCRISPR plasmid into the HB100 strain. The pCRISPR plasmid may be expressed and endonuclease Cas9 was targeted to a location on the S. cerevisiae genome by a gRNA molecule. At the location, the Cas9 protein may create a double stranded break in the DNA and the Maf1 donor polynucleotide may be integrated into the genome at the break by homologous recombination. Stable transformation of the Maf1 donor polynucleotide into the HB100 strain provides the HB106 base strain.

The Acc1-PGK1p donor polynucleotide shown in SEQ ID NO: 6 was prepared and amplified. DNA SOEing was used to create a single donor DNA fragment from three polynucleotides for Acc1-PGK1 integration. The first polynucleotide was the 5' region of genomic homology that allows the donor to recombine into the genome at a specific locus. The second polynucleotide coded for the PGK1 promoter region. The third polynucleotide included the 3' region for genomic homology to facilitate targeted integration into the S. cerevisiae genome.

The Acc1-PGK1 donor polynucleotide was co-transformed with the pCRISPR plasmid. The pCRISPR plasmid was expressed and endonuclease Cas9 was targeted to a location on the S. cerevisiae genome by a gRNA molecule. At the location, the Cas9 protein created a double stranded break in the DNA and the Acc1-PGK1 donor polynucleotide was integrated into the genome at the break by homologous recombination. Stable transformation of donor polynucleotide into the HB100 strain provides the HB110 base strain with Acc1 under regulation of the PGK1 promoter.

Table 2 provides a summary of the base strains that were prepared by genome modification of S. cerevisiae. Each base strain shown in Table 2 is a leucine and uracil auxotroph, and none of them include a plasmid.

TABLE 2

Base Transformed Strains Prepared for Polyketide Production

| Strain | Modification | Integration |
| --- | --- | --- |
| HB82 | PDH bypass | SEQ ID NO: 2 |
| HB100 | PDH bypass, NPGa (site 14) | SEQ ID NOs: 2, 8 |
| HB106 | PDH bypass, NPGa (site 14), Maf1 (site 5) | SEQ ID NOs: 2, 8, 6 |
| HB110 | PDH bypass, NPGa (site 14), Maf1 (site 5), Acc1 promoter replaced with PGK1$^P$ | SEQ ID NOs: 2, 8, 6, 4 |

Stable Transformation for Strain Construction

Plasmids were transformed into S. cerevisiae using the lithium acetate heat shock method as described by Gietz.

Transgenic S. cerevisiae HB80, HB98, HB102, HB135, HB137 and HB138 were prepared from the HB42, HB100, HB106 and HB110 bases strain by transformation of HB42 with expression plasmids, and HB80A was prepared by transformation of HB80, as shown below in Table 3. HB80, HB98 and HB102 each include and express DiPKS. HB80A includes and expresses DiPKS$^{G1516D;\ G1518A}$. HB135, HB137 and HB138 each include and express DiPKS$^{G1516R}$. HB98 includes and expresses DiPKS and NPGa from a plasmid.

TABLE 3

Strains including plasmids expressing polyketide synthase

| Strain | Base Strain | Plasmid |
| --- | --- | --- |
| HB80 | HB42 | pDiPKS |
| HB80A | HB80 | pDIPKSm1 |
| HB98 | HB42 | pDiPKS |
|  |  | pNPGa |
| HB102 | HB100 | pDIPKS |
| HB135 | HB100 | pDIPKSm2 |
| HB137 | HB106 | pDIPKSm2 |
| HB138 | HB110 | pDIPKSm2 |

Yeast Growth and Feeding Conditions

Yeast cultures were grown in overnight cultures with selective media to provide starter cultures. The resulting starter cultures were then used to inoculate triplicate 50 ml cultures to an optical density at having an absorption at 600 nm ("$A_{600}$") of 0.1.

Yeast was cultured in media including YNB+2% raffinose+2% galactose+1.6 g/L 4DO*. "4DO*" refers to yeast synthetic dropout media supplement lacking leucine and uracil. "YNB" is a nutrient broth including the chemicals listed in the first two columns side of Table 4. The chemicals listed in the third and fourth columns of Table 4 are included in the 4DO* supplement.

TABLE 4

YNB Nutrient Broth and 4DO* Supplement

| YNB | | 4DO* | |
|---|---|---|---|
| Chemical | Concentration | Chemical | Concentration |
| Ammonium Sulphate | 5 g/L | Adenine | 18 mg/L |
| Biotin | 2 µg/L | p-Aminobenzoic acid | 8 mg/L |
| Calcium pantothenate | 400 µg/L | Alanine | 76 mg/ml |
| Folic acid | 2 µg/L | Arginine | 76 mg/ml |
| Inositol | 2 mg/L | Asparagine | 76 mg/ml |
| Nicotinic acid | 400 µg/L | Aspartic Acid | 76 mg/ml |
| p-Aminobenzoic acid | 200 µg/L | Cysteine | 76 mg/ml |
| Pyridoxine HCl | 400 µg/L | Glutamic Acid | 76 mg/ml |
| Riboflavin | 200 µg/L | Glutamine | 76 mg/ml |
| Thiamine HCL | 400 µg/L | Glycine | 76 mg/ml |
| Citric acid | 0.1 g/L | Histidine | 76 mg/ml |
| Boric acid | 500 µg/L | myo-Inositol | 76 mg/ml |
| Copper sulfate | 40 µg/L | Isoleucine | 76 mg/ml |
| Potassium iodide | 100 µg/L | Lysine | 76 mg/ml |
| Ferric chloride | 200 µg/L | Methionine | 76 mg/ml |
| Magnesium sulfate | 400 µg/L | Phenylalanine | 76 mg/ml |
| Sodium molybdate | 200 µg/L | Proline | 76 mg/ml |
| Zinc sulfate | 400 µg/L | Serine | 76 mg/ml |
| Potassium phosphate monobasic | 1.0 g/L | Threonine | 76 mg/ml |
| Magnesium sulfate | 0.5 g/L | Tryptophan | 76 mg/ml |
| Sodium chloride | 0.1 g/L | Tyrosine | 76 mg/ml |
| Calcium chloride | 0.1 g/L | Valine | 76 mg/ml |

Quantification of Metabolites

Intracellular metabolites were extracted from the *S. cerevisiae* cells using methanol extraction. One mL of liquid culture was spun down at 12,000×g for 3 minutes. 250 µL of the resulting supernatant was used for extracellular metabolite quantification. The resulting cell pellet was suspended in 200 µl of −40° C. 80% methanol. The mixture was vortexed and chilled on ice for 10 minutes. After chilling on ice for 10 minutes, the mixture was spun down at 15,000×g at 4° C. for 14 minutes. The resulting supernatant was collected. An additional 200 µl of −40° C. 80% methanol was added to the cell debris pellet and the mixture was vortexed and chilled for 10 minutes on ice. After chilling on ice for 10 minutes, the mixture was spun down at 15,000×g at 4° C. for 14 minutes. The resulting 200 µl of supernatant was added to the previously collected 200 µl of supernatant, providing a total of 400 µl of 80% methanol with intracellular metabolites.

Intracellular metabolites were quantified using high performance liquid chromatography ("HPLC") and mass spectrometry ("MS") methods. An Agilent 1260 autosampler and HPLC system connected to a ThermoFinnigan LTQ mass spectrometer was used. The HPLC system included a Zorbax Eclipse C18 2.1 µm×5.6 mm×100 mm column.

The metabolites were injected in 10 µl samples using the autosampler and separated on the HPLC using at a flow rate of 1 ml/min. The HPLC separation protocol was 20 mins total with (a) 0-2 mins of 98% Solvent A and 2% Solvent B; (b) 2-15 mins to get to 98% solvent B; (c) 15-16.5 minutes at 98% solvent B; (d) 16.5-17.5 minutes to get to 98% A; and (e) a final 2.5 minutes of equilibration at 98% Solvent A. Solvent A was acetonitrile+0.1% formic acid in MS water and solvent B was 0.1% formic acid in MS water.

After HPLC separation, samples were injected into the mass spectrometer by electrospray ionization and analyzed in positive mode. The capillary temperature was held at 380° C. The tube lens voltage was 30 V, the capillary voltage was 0 V, and the spray voltage was 5 kV. Similarly, after HPLC-MS/MS, olivetol was analyzed as a parent ion at 181.2 and a daughter ion at 111, while methyl-olivetol analyzed as a parent ion at 193.2 and a daughter ion at 125.

Different concentrations of known standards were injected to create a linear standard curve. Standards for olivetol and methyl-olivetol standards were purchased from Sigma Aldrich.

Example I

The yeast strain HB80 as described above in Table 3 was cultured in the YNB+2% raffinose+2% galactose+1.6 g/L 4DO* media. Production of methyl-olivetol from raffinose and galactose was observed, demonstrating direct production in yeast of methyl-olivetol. The methyl-olivetol was produced at concentrations of 3.259 mg/L.

Example II

The yeast strain HB80A as described above in Table 3 was cultured in the YNB+2% raffinose+2% galactose+1.6 g/L 4DO* media. Production of both olivetol and methyl-olivetol from raffinose and galactose, catalyzed by DiPKS$^{G1516D;\ G1518A}$ was observed. This data demonstrates direct production in yeast of both olivetol and methyl-olivetol without inclusion of hexanoic acid.

Figure 10:
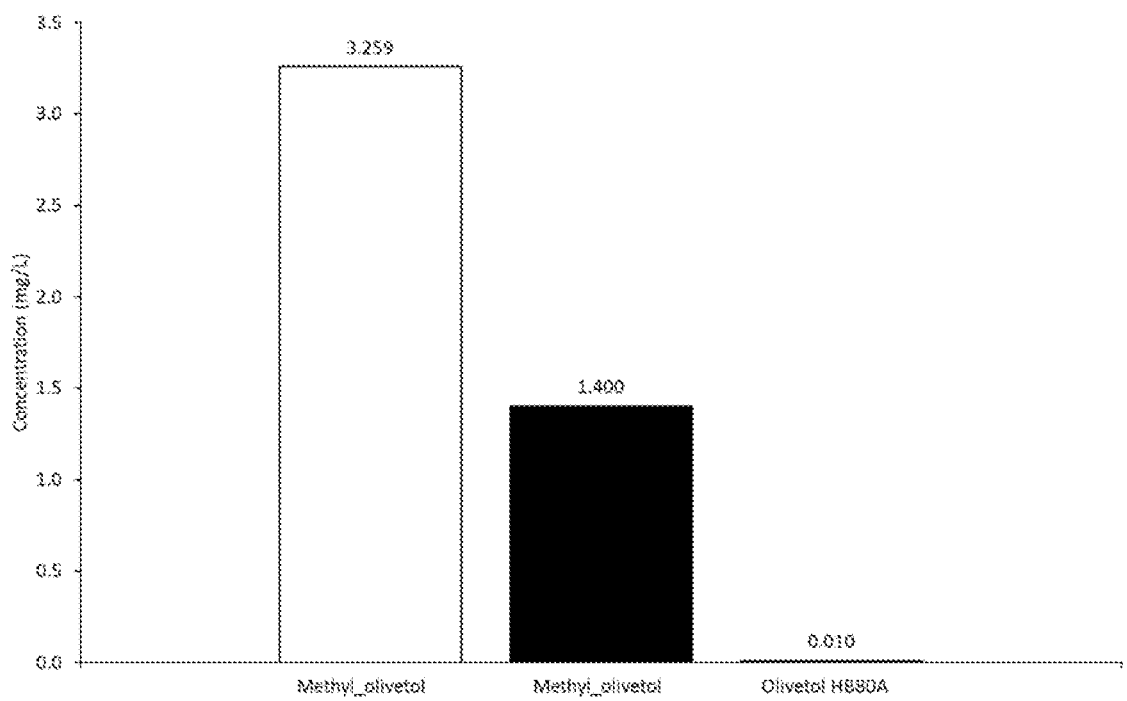
FIG. 10 shows production of methyl-olivetol by DiPKS, and of both methyl-olivetol and olivetol by DiPKS$^{G1516D;\ G1518A}$.

FIG. 10 shows concentrations of methyl-olivetol produced by HB80 ("Methyl_Olivetol HB80") from Example I, and of both olivetol and methyl-olivetol produced by HB80A ("Methyl_Olivetol HB80A" and "Olivetol HB80A", respectively). Samples of culture were taken at 72 hours. HB80A produces a majority of methyl-olivetol (1.4 mg methyl-olivetol per L of culture compared with 0.010 mg per L of culture olivetol), and produced less methyl-olivetol and olivetol combined than methyl-olivetol that is produced by HB80 (3.26 mg/L).

Example III

The yeast strain HB98 as described above in Table 3 was cultured in the YNB+2% raffinose+2% galactose+1.6 g/L 4DO* media. Production of methyl-olivetol from raffinose and galactose, catalyzed by DiPKS, was observed. This data demonstrates increased methyl-olivetol production compared with HB80 as described in Example I, and also without inclusion of hexanoic acid.

Figure 11:
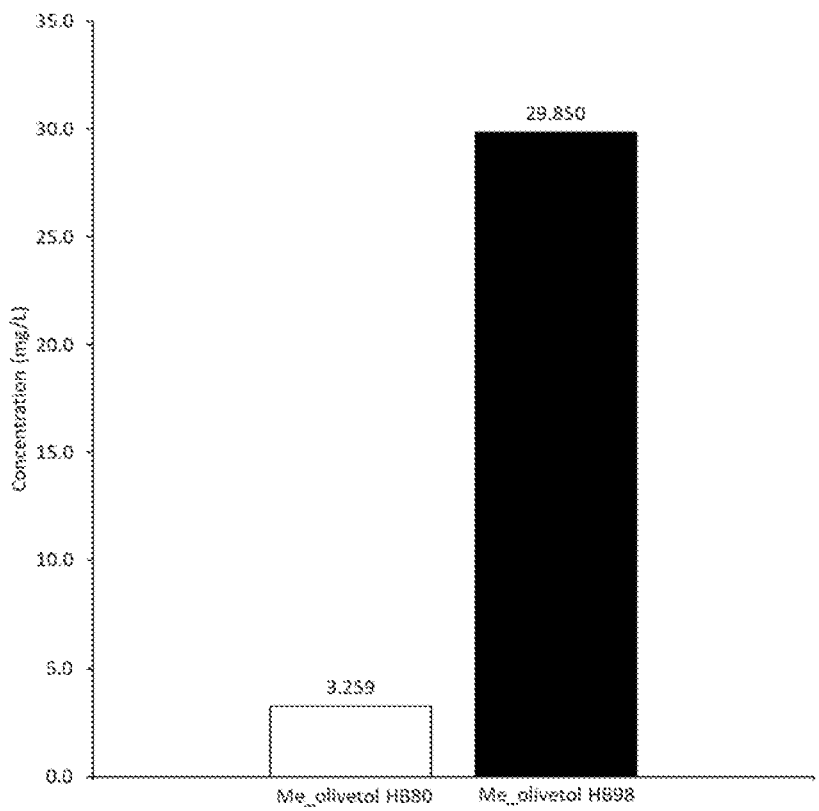
FIG. 11 shows production of methyl-olivetol by DiPKS in two separate strains of *S. cerevisiae*.

FIG. 11 shows concentrations of methyl-olivetol produced by HB80 ("Methyl_Olivetol HB80") from Example I, and of methyl-olivetol produced by HB98 ("Methyl_Olivetol HB98") from Example III. Samples of culture were taken at 72 hours. HB98 produced 29.85 mg/L methyl-olivetol while HB80 produced only 3.26 mg methyl-olivetol per L of culture. HB98 produced nearly 10× as much methyl-olivetol as HB80.

Example IV

The yeast strain HB102 as described above in Table 3 was cultured in the YNB+2% raffinose+2% galactose+1.6 g/L 4DO* media. Production of methyl-olivetol from raffinose and galactose was observed, demonstrating an increased production in yeast of methyl-olivetol at 42.44 mg/L as compared to strain HB98, which produced only 29.85 mg/L methyl-olivetol. This demonstrated that the genomically integrated version of NpgA is functional.

Figure 12:
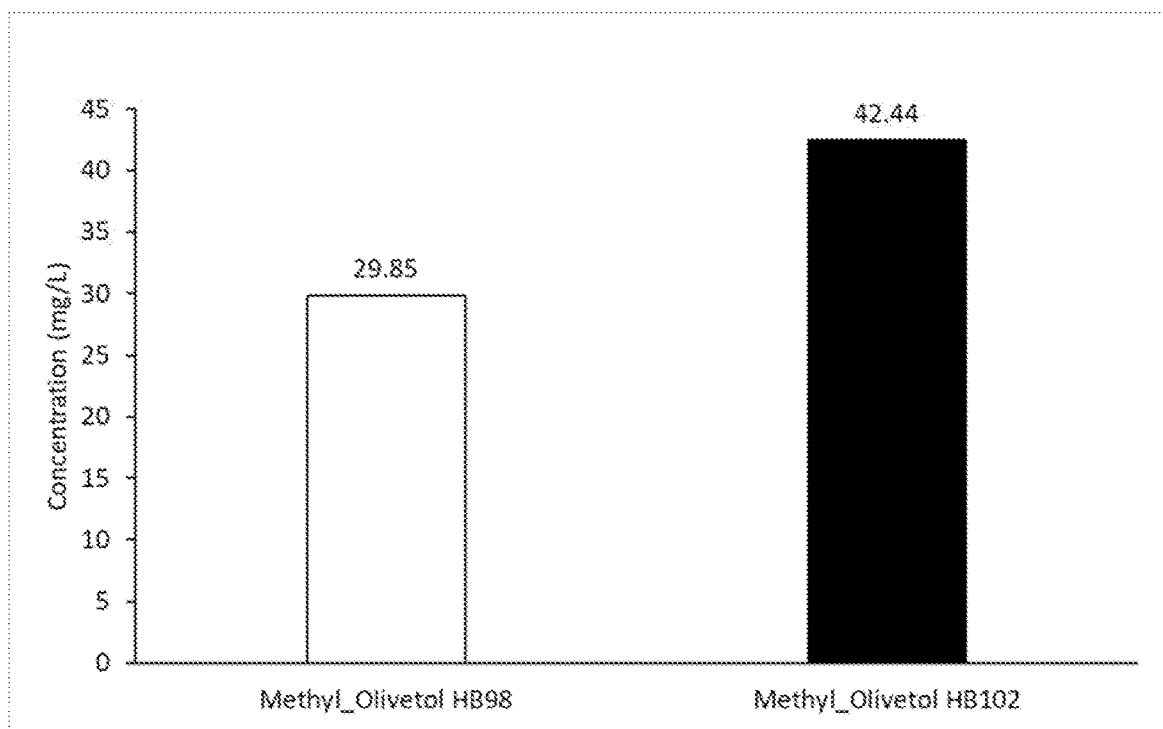
FIG. 12 shows production of methyl-olivetol by DiPKS in two separate strains of *S. cerevisiae*.

FIG. 12 shows concentrations of methyl-olivetol produced by HB102 ("Methyl_olivetol HB102") from Example IV as compared to the production of methyl-olivetol from strain HB98 in Example III ("Methyl_olivetol HB98").

Example V

The yeast strain HB135 as described above in Table 3 was cultured in the YNB+2% raffinose+2% galactose+1.6 g/L 4DO* media. Production of olivetol from raffinose and galactose was observed, demonstrating an production in yeast of olivetol without any hexanoic acid and at high titres of 49.24 mg/L and no production of methyl-olivetol. This is comparable to the production of methyl-olivetol by strain HB102 demonstrating that the mutation of DIPKS was effective in production of Olivetol as opposed to methyl-Olivetol.

Figure 13:
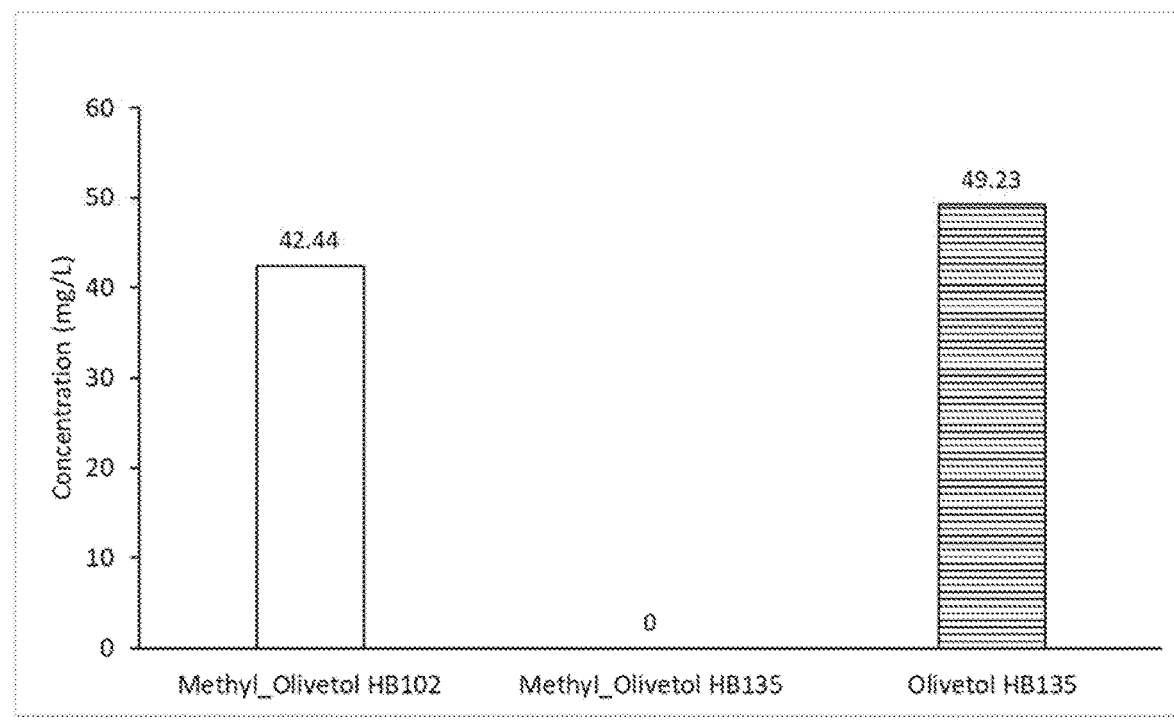
FIG. 13 shows production of methyl-olivetol by DiPKS, and of both methyl-olivetol and olivetol by DiPKS$^{G1516R}$ in two separate strains of *S. cerevisiae*.

FIG. 13 shows concentrations of olivetol and methyl-olivetol produced by HB135 ("Methyl_olivetol HB135" and "Olivetol HB135 respectively) from Example VI as compared to the production of methyl-olivetol from strain HB102 in Example IV ("Methyl_olivetol HB102").

Example VII

The yeast strains HB137 and HB138 as described above in Table 3 were cultured in the YNB+2% raffinose+2% galactose+1.6 g/L 4DO* media. Production of olivetol from raffinose and galactose was observed in both strains. Strain HB137 produced 61.26 mg/L of olivetol and strain HB138 produced 74.26 mg/L of olivetol demonstrating the positive effect of Maf1 integration and Acc1-promoter swap on olivetol titres.

Figure 14:
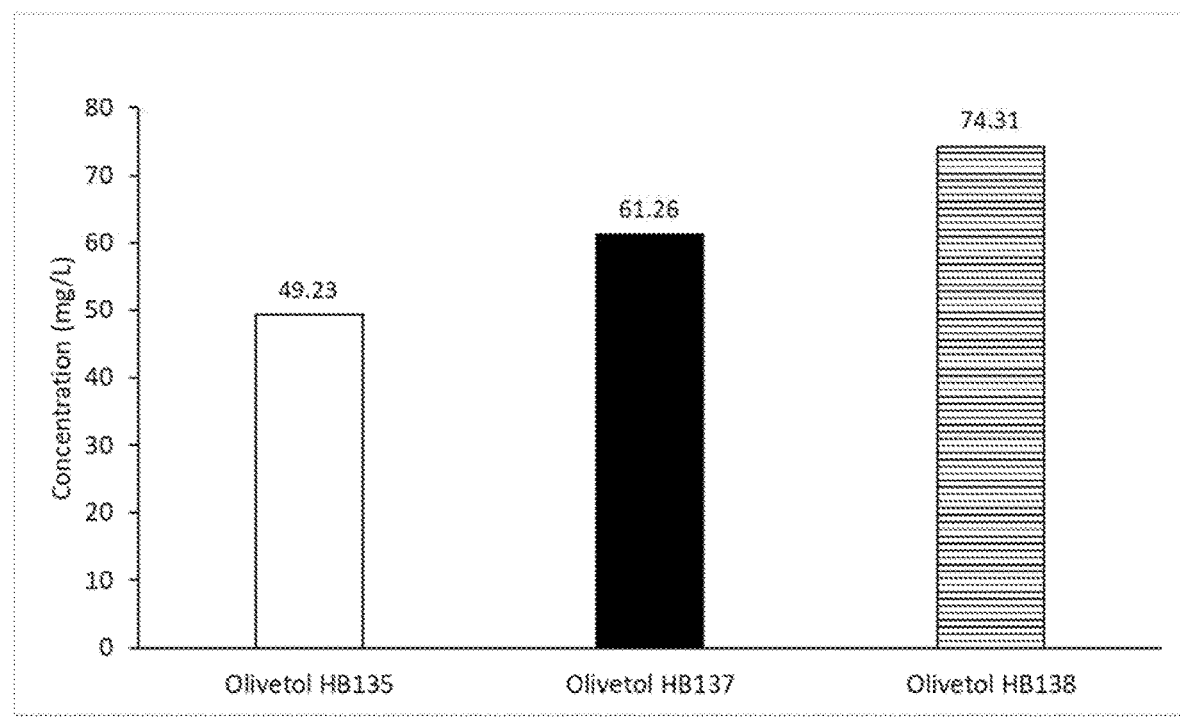
FIG. 14 shows production of olivetol by DiPKS$^{G1516R}$, in three separate strains of *S. cerevisiae*.

FIG. 14 shows the concentrations of olivetol produced by HB137 ("Olivetol HB137") and HB138 ("Olivetol HB138") from Example VII as compared to olivetol produced by HB135 ("Olivetol HB135") in Example VI.

REFERENCES

M. B. Austin, T. Saito, M. E. Bowman, S. Haydock, A. Kato, B. S. Moore, R. R. Kay and Noel, J. P. (2006) "Biosynthesis of *Dictyostelium discoideum* differentiation-inducing factor by a hybrid type I fatty acid-type III polyketide synthase" *Nature chemical biology*, 2(9), 494.

S. W. Baba, G. I. Belogrudov, J. C. Lee, P. T. Lee, J. Strahan and J. N. Shepherd, C. F. Clarke (2003) "Yeast Coq5 C-Methyltransferase Is Required for Stability of Other Polypeptides Involved in Coenzyme Q Biosynthesis" *The Journal of Biological Chemistry*, 279(11): 10052-10059.

C. Chambon, V. Ladeveze, A. Oulmouden, M. Servouse, and E Karst (1990) "Isolation and properties of yeast mutants affected in farnesyl diphosphate synthetase" *Curr Genet*, 18: 41-46.

M. J. C. Fischer, S. Meyer, P. Claudel, M. Bergdoll and F. Karst (2011) "Metabolic Engineering of Monoterpene Synthesis in Yeast" *Biotechnology and Bioengineering*, 108(8): 1883-1892.

Bai Flagfeldt, D., Siewers, V., Huang, L. and Nielsen, J. (2009) "Characterization of chromosomal integration sites for heterologous gene expression in *Saccharomyces cerevisiae*" *Yeast*, 26, 545-551.

S. Gagne. "The Polyketide Origins of Cannabinoids in *Cannabis Sativa*." Diss. U of Saskatchewan, 2013.

R. Ghosh, A. Chhabra, P. A. Phatale, S. K. Samrat, J. Sharma, A. Gosain, D. Mohanty, S. Saran and R. S. Gokhale (2008) "Dissecting the Functional Role of Polyketide Synthases in *Dictyostelium discoideum* biosynthesis of the differentiation regulating factor 4-methyl-5-pentylbenzene-1,3-diol" *Journal of Biological Chemistry*, 283(17), 11348-11354.

C. Huang, H. Wu, Z. Liu, J. Cai, W. Lou and M. Zong (2012) "Effect of organic acids on the growth and lipid accumulation of oleaginous yeast *Trichosporon fermentans*" *Biotechnology for Biofuels*, 5:4.

Z. Hunkova and Z. Fencl (1977) "Toxic Effects of Fatty Acids on Yeast Cells: Dependence of Inhibitory Effects on Fatty Acid Concentration" *Biotechnology and Bioengineering*, XIX: 1623-1641.

J. Kaminska, K. Grabinska, M. Kwapisz, J. Sikora, W. J. Smagowicz, G. Palamarczyk, T. Zoladek, M. Boguta, "The isoprenoid biosynthetic pathway in *Saccharomyces cerevisiae* is affected in a maf1-1 mutant with altered tRNA synthesis" (2002) *FEMS Yeast Research* 2: 31-37.

D. Ro, E. M. Paradise, M. Ouellet, K. J. Fisher, K. L. Newman, J. M. Ndungu, K. A. Ho, R. A. Eachus, T. S. Ham, J. Kirby, M. C. Y. Chang, S. T. Withers, Y. Shiba, R. Sarpong and J. D. Keasling (2006) "Production of the antimalarial drug precursor artemisinic acid in engineered yeast" *Nature Letters* 440: 930-943.

S. Shi, Y. Chen, V. Siewers and J. Nielsen, "Improving Production of Malonyl Coenzyme A-Derived Metabolites by Abolishing Snf1-Dependent Regulation of Acc1" (2014) *American Society for Microbiology* 5(3): e01130-14. doi: 10.1128/mBio.01130-14.

Y. Shiba, E. M. Paradise, J. Kirby, D. Ro and J. D. Keasling "Engineering of the pyruvate dehydrogenase bypass in *Saccharomyces cerevisiae* for high-level production of isoprenoids" (2007) *Metabolic Engineering* 9: 160-168.

M. A. Skiba, A. P. Sikkema, W. D. Fiers, W. H. Gerwick, D. H. Sherman, C. C. Aldrich and J. L. Smith "Domain Organization and Active Site Architecture of a Polyketide Synthase C-methyltransferase" *ACS Chem. Biol.*; Just Accepted Manuscript•DOI: 10.1021/acschembio.6b00759•Publication Date (Web): 10 Oct. 2016. Downloaded from http://pubs.acs.org on Oct. 11, 2016.

M. Telloa, T. Kuzuyamab, L. Heidec, J. P. Noela and S. B. Richarda (2008) "The ABBA family of aromatic prenyltransferases: broadening natural product diversity" *Cell Mol Life Sci.;* 65(10): 1459-1463.

C. A. Viegas, M. F. Rosa, I. Sa-Correia and J. M. Novais "Inhibition of Yeast Growth by Octanoic and Decanoic Acids Produced during Ethanolic Fermentation" (1989) *Applied and Environmental Microbiology* 55(1): 21-28.

Sequences

The .txt file of the sequence listing is being electronically filed with this application.

Examples Only

In the preceding description, for purposes of explanation, numerous details are set forth in order to provide a thorough understanding of the embodiments. However, it will be apparent to one skilled in the art that these specific details are not required.

The above-described embodiments are intended to be examples only. Alterations, modifications and variations can be effected to the particular embodiments by those of skill in the art without departing from the scope, which is defined solely by the claims appended hereto.

What is claimed is:

1. A *D. discoideum* polyketide synthase (DiPKS) enzyme with a primary structure with between 99% and 100% amino acid residue sequence identity with a protein coded for by a reading frame defined by bases 523 to 9966 of SEQ ID NO:13, with a charged amino acid residue at amino acid residue position 1516 in place of a glycine residue at position 1516.

2. The DiPKS polyketide synthase of claim 1 wherein amino acid residue 1516 is arginine.

3. The DiPKS polyketide synthase of claim 1 wherein amino acid residue 1516 is aspartate and residue 1518 is alanine.

* * * * *

SEQUENCE LISTING

```
<160> NUMBER OF SEQ ID NOS: 14

<210> SEQ ID NO 1
<211> LENGTH: 9444
<212> TYPE: DNA
<213> ORGANISM: Artificial Sequence
<220> FEATURE:
<223> OTHER INFORMATION: Yeast optimized DiPKS from Dictyostelium
      discoideum
<220> FEATURE:
<221> NAME/KEY: Motif 1
<222> LOCATION: (4528)..(4554)
<220> FEATURE:
<221> NAME/KEY: C-methyltransferase domain
<222> LOCATION: (4528)..(4890)
<220> FEATURE:
<221> NAME/KEY: Motif 2
<222> LOCATION: (4787)..(4809)
<220> FEATURE:
<221> NAME/KEY: Motif 3
<222> LOCATION: (4867)..(4899)

<400> SEQUENCE: 1
atgaacaaga actccaaaat ccagtcccca aactcttctg atgttgctgt tattggtgtt      60
ggttttagat tcccaggtaa ctctaatgac ccagaatctt tgtggaacaa cttgttggat     120
ggtttcgatg ctattaccca agtcccaaaa gaaagatggg ctacttcttt tagagagatg     180
ggtttgatca agaacaagtt cggtggtttc ttgaaggatt ctgaatggaa gaatttcgac     240
cctttgttct ttggtatcgg tccaaaagaa gctccattca ttgatccaca acaaaggttg     300
ttgttgtcca tcgtttggga atctttggaa gatgcttaca tcagaccaga tgaattgaga     360
ggttctaaca ctggtgtttt catcggtgtt tctaacaacg attacaccaa gttgggtttc     420
caagacaact actctatttc tccatacact atgaccggct ctaactcttc attgaactcc     480
aacagaattt cctactgctt cgatttttaga ggtccatcca ttactgttga taccgcttgt     540
tcttcttcct tggtttctgt taatttgggt gtccaatcca tccaaatggg tgaatgtaag     600
attgctattt gcggtggtgt taacgctttg tttgatccat ctacatctgt tgccttttcc     660
aagttgggtg ttttgtctga aaatggcaga tgcaactctt ttagtgatca agcctctggt     720
tacgttagat ctgaaggtgc tggtgttgtt gttttgaagt ctttggaaca agctaagttg     780
gatggtgata gaatctacgg tgttatcaag ggtgtttcct ctaatgaaga tggtgcttct     840
aatggtgaca agaactcttt gactactcca tcttgtgaag cccaatccat taacatttct     900
aaggctatgg aaaaggcctc cttgtctcca tctgatatct attacattga agcccatggt     960
actggtactc cagttggtga tccaattgaa gttaaggcct tgtccaagat cttctccaac    1020
tctaacaaca accagttgaa caacttctct accgatggta atgataacga tgatgatgat    1080
gacgataaca cctctccaga accattattg attggctcat tcaagtccaa catcggtcat    1140
```

-continued

```
ttggaatctg ctgctggtat tgcttctttg attaagtgtt gcttgatgtt gaagaacagg    1200
atgttggttc catccattaa ctgctctaat ttgaacccat ccattccatt cgatcagtac    1260
aacatctccg ttatcagaga atcagacaa ttcccaaccg ataagttggt taacatcggt     1320
atcaattctt tcggtttcgg tggttctaac tgccatttga ttattcaaga gtacaacaac    1380
aacttcaaga caactctac catctgcaat aacaacaaca acaacaataa caacatcgac     1440
tacttgatcc caatctcctc taagactaag aagtccttgg ataagtactt gattttgatc    1500
aagaccaact ccaactacca caaggatatt tctttcgatg acttcgtcaa gttccaaatc    1560
aagtctaagc agtacaactt gtccaacaga atgactacca ttgctaacga ttggaactcc    1620
ttcattaagg gttctaacga attccacaac ttgatcgaat ctaaggatgg tgaaggtggt    1680
tcttcatctt ctaacagagg tattgattcc gccaatcaaa tcaacactac tactacctct    1740
accatcaacg atatcgaacc tttgttggtt ttcgttttct gtggtcaagg tccacaatgg    1800
aatggtatga ttaagacctt gtacaactcc gagaacgttt tcaagaacac cgttgatcat    1860
gttgacagca tcttgtacaa gtacttcggt tactccattt tgaacgtctt gtctaagatc    1920
gatgataacg acgattccat caaccatcca atagttgctc aaccatcttt gttcttgttg    1980
caaattggtt tggtcgagtt gtttaagtac tggggtatct acccatctat ctctgttggt    2040
cattctttcg gtgaagtctc ttcttattac ttgtccggta tcatctcttt ggaaaccgct    2100
tgtaaaatcg tctacgtcag atcctctaat cagaacaaaa ctatgggttc cggtaagatg    2160
ttggttgttt ctatgggttt taagcaatgg aacgatcaat tctctgctga atggtccgat    2220
attgaaattg cttgttacaa cgctccagat tccatagttg ttactggtaa cgaagaaaga    2280
ttgaaagaat tgtccatcaa gttgtccgac gaatccaatc aaattttcaa caccttcttg    2340
aggtccccat gttcttttca ttcttcccat caagaagtca tcaagggttc tatgttcgaa    2400
gagttgtcta acttgcaatc tactggtgaa accgaaatcc ctttgttctc tactgttact    2460
ggtagacaag ttttgtctgg tcatgttact gctcaacaca tctacgataa tgttagagaa    2520
ccagtcttgt tccaaaagac gattgaatcc attacctcct acatcaagtc tcactaccca    2580
tccaatcaaa aggttatcta cgttgaaatt gctccacacc caaccttgtt ttcattgatc    2640
aaaaagtcca tcccatcctc caacaagaat tcctcttctg ttttgtgtcc attgaacaga    2700
aaagaaaact ccaacaactc ctacaagaag ttcgtttctc agttgtactt caacggtgtt    2760
aacgttgact tcaacttcca gttgaactcc atttgcgata acgttaacaa cgatcaccat    2820
ttgaacaacg tcaagcaaaa ctccttcaaa gagactacca attccttgcc aagataccaa    2880
tgggaacaag atgaatattg gtccgaacca ttgatctcca gaaagaatag attggaaggt    2940
ccaactactt ccttgttggg tcatagaatt atctacagct tcccagtttt ccaatccgtt    3000
ttggacttgc aatctgacaa ctacaaatac ttgttggacc acttggttaa cggtaagcca    3060 gttttttccag gtgctggtta tttggatatc atcatcgaat tcttcgacta ccaaaagcag    3120
cagttgaatt cctctgattc ctctaactcc tacatcatca cgttgacaa gatccaattc     3180 ttgaacccaa ttcacttgac cgaaaacaag ttgcaaacct tgcaatcttc tttcgaacct    3240
atcgttacta agaagtctgc cttctctgtt aacttcttca tcaaggatac cgtcgaggat    3300
caatctaagg ttaagtctat gtctgacgaa acttggacta cacttgtaa ggctaccatt     3360 tccttggaac aacaacagcc atctccatct tctactttga ctttgtctaa gaagcaagac    3420
ttgcagatct tgagaaacag atgcgatatt agcaagctag acaagtttga gttgtacgac    3480
aagatctcta agaatttggg cttgcagtac aactccttgt ttcaagttgt tgataccatc    3540
```

```
gaaactggta aggattgctc ttttgctact ttgtctttgc cagaagatac tttgttcacc      3600 accatttga acccatgctt gttggataac tgtttccatg gtttgttgac cttgatcaac      3660
gaaaagggtt ctttcgttgt cgagtccatt tcttctgttt ctatctactt ggagaacatc      3720
ggttccttca atcaaacttc tgttggtaac gtccagttct acttgtacac cactatttct      3780
aaagccacct cctttagttc tgaaggtact tgtaagttgt tcaccaagga tggttccttg      3840
attttgtcta tcggtaagtt catcatcaag tccaccaatc caaagtctac taagaccaac      3900
gaaactatcg aatctccatt ggacgaaacc ttctctattg aatggcaatc taaggattct      3960
ccaattccaa ccccacaaca aatccaacaa caatctccat tgaactctaa cccatccttc      4020
attagatcta ccatcttgaa ggacatccag ttcgaacaat actgctcctc cattatccac      4080
aaagaattga tcaaccacga aaagtacaag aaccagcaat ccttcgatat caactccttg      4140
gaaaaccact tgaacgatga ccaattgatg gaatccttgt ccatctccaa agaatacttg      4200
agattcttca ccaggatcat ctccatcatt aagcaatacc caaagatctt gaacgaaaaa      4260
gagctaaaag aattgaaaga aatcatcgaa ttgaagtacc catccgaagt tcagttgttg      4320
gaattcgaag ttatcgagaa ggtgtccatg attatcccaa agttgttgtt cgaaaacgac      4380
aagcaatctt ccatgaccct tgttccaaga t aacttgttga ccaggttcta ctccaattct      4440
aactctacca gattctactt ggaaagggtt tccgaaatgg tcttggaatc tattagacca      4500
atcgtcagag aaaagagggt gttcagaatt ttggaaattg gtgctggtac aggctctttg      4560
tctaatgttg ttttgactaa gttgaacacc tacttgtcca ccttgaattc taatggtggt      4620
tctggttaca acatcatcat tgagtacacc ttcaccgata tttccgccaa cttcattatt      4680
ggtgaaatcc aagaaccat gtgcaacttg tacccaaacg ttactttcaa gttctccgtc      4740
ttggacttgg agaaagagat tattaactcc tccgatttct tgatgggtga ttacgatata      4800
gttttgatgg cctacgttat ccatgccgtt tctaacatta agttctccat cgaacagttg      4860
tacaagttgt tgtctccaag aggttggttg ttgtgtattg aacctaagtc caacgttgtg      4920
ttctccgatt tggttttcgg ttgttttaat cagtggtgga actactacga tgatattaga      4980
actacccact gctccttgtc tgaatctcaa tggaatcagt tgttgttgaa ccagtccttg      5040
aacaacgaat cctcttcttc ttctaactgt tacggtggtt tctccaacgt ttctttattt      5100
ggtggtgaaa aggatgtcga ctcccattct ttcatattgc actgccaaaa agaatccatc      5160
tcccaaatga agttagccac cactattaac aacggtttgt catctggttc catcgttatc      5220
gttttgaact ctcaacaatt gaccaacatg aagtcctacc caaaggttat tgagtatatt      5280
caagaggcta cctctttgtg caagaccatt gaaattatcg attccaagga cgtcttgaac      5340
tctaccaatt cagttttgga aaagatccaa aagtccttgt tggtgttctg tttgttgggt      5400
tatgacttgt tggagaacaa ctaccaagaa cagtctttcg aatacgttaa gttgttgaac      5460
ttgatctcta ctaccgcctc ttcatctaat gataagaaac caccaaaggt cttgttgatc      5520
accaagcaat ctgaaagaat ctccaggtct ttctactcca gatccttgat tggtatttcc      5580
agaacctcta tgaacgagta cccaaatttg tccattacct ctatcgattt ggataccaac      5640
gactactcat tgcagtcttt gttgaagcca atcttcagca actctaagtt ttccgacaac      5700
gagttcatct tcaaaaaggg cttgatgttc gtgtccagga tctttaagaa caagcagttg      5760
ctagaatcct ccaacgcttt tgaaactgac tcttctaact tgtactgtaa ggcctcttct      5820
gacttgtctt acaagtacgc tattaagcag tctatgttga ccgaaaatca gatcgaaatc      5880
```

```
aaggttgaat gcgtcggtat taacttcaag gacaacctat tctacaaggg cttgttgcca      5940
caagaaattt tcagaatggg tgacatctac aatccaccat atggtttgga atgtctggt       6000
gttattacca gaattggttc taacgtcacc gaatactcag ttggtcaaaa tgttttggt       6060
ttcgccagac attctttggg ttctcatgtt gttaccaaca aggatttggt tatcttgaag      6120
ccagatacca tctcattttc tgaagctgct tctatcccag ttgtttactg tactgcttgg     6180
tactccttgt tcaacattgg tcagttgtct aacgaagaat ccatcctaat tcattctgct     6240
actggtggtg taggtttggc ttctttgaat ttgttgaaaa tgaagaatca gcaacagcaa     6300
ccattgacca atgtttatgc tactgttggc tctaacgaga agaagaagtt cttgatcgat     6360
aacttcaaca acttgttcaa agaggacggc gaaaacattt tctctaccag agacaaagaa    6420
tactccaacc agttggaatc caagatcgat gttattttga caccttgtc cggtgaattc      6480
gtcgaatcta atttcaagtc cttgagatcc ttcggtagat tgattgattt gtctgctact    6540
cacgtttacg ccaatcaaca aattggtcta ggtaacttca gttcgacca cttgtattct     6600
gctgttgact tggaaagatt gatcgacgaa aaacctaagt tgttgcagtc catcttgcaa    6660
agaattacca actctatcgt caacggttcc ttggaaaaaa ttccaattac catcttccca    6720
tccaccgaaa ctaaggatgc tatcgaatta ttgtccaaga gatcccatat cggtaaagtt     6780
gttgtagatt gcaccgatat ctctaagtgt aatcctgttg gtgatgtgat caccaacttc    6840
tctatgagat tgccaaagcc aaactaccag ttgaatttga actccacctt gttgattact     6900
ggtcagtctg gtttgtctat cccttttgttg aattggttgt tgtctaagtc tggtggtaac   6960
gttaagaacg ttgtcatcat ttctaagtcc accatgaagt ggaagttgca gactatgatt    7020
tcccatttcg tttccggttt cggtatccat tttaactacg ttcaagtcga catctccaac   7080
tacgatgctt tgtctgaagc tattaagcaa ttgccatctg atttgccacc aatcacctct    7140
gtttttcatt tggctgctat ctacaacgat gttccaatgg atcaagttac catgtctacc    7200
gttgaatctg ttcataaccc taaagttttg ggtgccgtta acttgcatag aatctctgtt    7260
tcttttggtt ggaagttgaa ccacttcgtc ttgttctctt ctattactgc tattaccggt    7320
tacccagacc aatctatcta caattctgcc aactctattt tggacgcttt gtccaacttt    7380
agaaggttta tgggtttgcc atccttctcc attaacttgg gtccaatgaa ggatgaaggt    7440
aaggtttcta ccaacaagag catcaagaag ctattcaagt ctagaggttt gccaagccta    7500
tccttgaaca agttatttgg tttgttggag gtcgtcatca acaacccatc taatcatgtt    7560
atcccatccc aattgatttg ctccccaatc gatttcaaga cctacatcga atctttctca    7620
actatgaggc caaagttgtt acacttgcaa cctaccattt ccaagcagca atcttctatc    7680
attaacgatt ctaccaaggc ttcctccaac atttcattgc aagataagat cacctccaag    7740
gtgtctgatt tgttgtccat tccaatctcc aagatcaact tcgatcatcc attgaaacac    7800
tacggcttgg attctttgtt gaccgttcaa ttcaaatcct ggatcgacaa agaattcgaa   7860
aagaacttgt tcacccatat ccaattggcc accatctcta ttaactcatt cttggaaaag   7920
gtgaacggct tgtctacaaa caataacaac aacaacaatt ccaacgtcaa gtcctctcca    7980
tccattgtca agaagaaat cgttaccttg gacaaggatc aacaaccatt gctattgaaa    8040
gaacaccagc acattatcat ctccccagat attagaatca acaagccaaa gagggaatcc   8100
ttgattagaa ccccaatctt gaacaaattc aaccagatca ccgaatccat tatcactcca   8160
tctacaccat ctttgtccca atccgatgtt ttgaaaactc caccaatcaa gtctttgaac    8220
aacactaaga actccagctt gattaacacc ccaccaattc aatctgtcca acaacatcaa    8280
```

-continued

```
aagcaacaac aaaaggtcca agtcatccaa caacagcaac aaccattatc cagattgtcc      8340
tacaagagca acaacaactc tttcgttttg ggtatcggta tttctgttcc aggtgaacct      8400
atttcccaac aatccttgaa agactccatc tccaatgact tttctgataa ggctgaaact      8460
aacgagaagg tcaagagaat ctttgagcaa tctcaaatca agaccagaca cttggttaga      8520
gattacacta agccagagaa ctccatcaag ttcagacatt tggaaaccat taccgatgtg      8580
aacaaccagt tcaagaaagt tgttccagat ttggctcaac aagcctgttt gagagctttg      8640
aaagattggg gtggtgataa gggtgatatt acccatatag tttctgttac ctccaccggt      8700
attatcatcc cagatgttaa tttcaagttg atcgacttgt tgggcttgaa caaggatgtt      8760
gaaagagtgt ctttgaacct aatgggttgt ttggctggtt tgagttcttt gagaactgct      8820
gcttctttgg ctaaggcttc tccaagaaat agaattttgg ttgtctgtac cgaagtctgc      8880
tccttgcatt tttctaatac tgatggtggt gatcaaatgg tcgcctcttc tattttttgct     8940 gatggttctg ctgcttacat tattggttgt aacccaagaa ttgaagaaac cccattatac      9000
gaagtcatgt gctccattaa cagatctttc ccaaataccg aaaacgccat ggtttgggat      9060
ttggaaaaag aaggttggaa cttgggtttg gatgcttcta ttccaattgt cattggttct      9120
ggtattgaag ccttcgttga tactttgttg gataaggcta agttgcaaac ttccactgct      9180
atttctgcta aggattgcga attcttgatt catactggtg gcaagtccat cttgatgaac      9240
atcgaaaatt ccttgggtat cgacccaaag caaactaaga atacttggga tgtttaccat      9300
gcctacggca atatgtcatc tgcctctgtt attttcgtta tggatcatgc cagaaagtcc      9360
aagtctttgc caacttactc aatttctttg gcttttggtc caggtttggc ttttgaaggt      9420
tgtttcttga agaacgtcgt ctaa                                            9444
```

```
<210> SEQ ID NO 2
<211> LENGTH: 14025
<212> TYPE: DNA
<213> ORGANISM: Artificial Sequence
<220> FEATURE:
<223> OTHER INFORMATION: Plasmid
<220> FEATURE:
<221> NAME/KEY: C1:p506 primer homology
<222> LOCATION: (1)..(50)
<220> FEATURE:
<221> NAME/KEY: 19 UP
<222> LOCATION: (51)..(761)
<220> FEATURE:
<221> NAME/KEY: L0
<222> LOCATION: (762)..(800)
<220> FEATURE:
<221> NAME/KEY: THD3p
<222> LOCATION: (801)..(1453)
<220> FEATURE:
<221> NAME/KEY: L1
<222> LOCATION: (1454)..(1493)
<220> FEATURE:
<221> NAME/KEY: ALD6
<222> LOCATION: (1494)..(2999)
<220> FEATURE:
<221> NAME/KEY: L2
<222> LOCATION: (3000)..(3039)
<220> FEATURE:
<221> NAME/KEY: LTP1
<222> LOCATION: (3364)..(3403)
<220> FEATURE:
<221> NAME/KEY: Tef1p
<222> LOCATION: (3404)..(3897)
<220> FEATURE:
<221> NAME/KEY: L3
<222> LOCATION: (3898)..(3937)
<220> FEATURE:
```

```
<221> NAME/KEY: Acs L641P
<222> LOCATION: (3938)..(5893)
<220> FEATURE:
<221> NAME/KEY: L4
<222> LOCATION: (5894)..(5933)
<220> FEATURE:
<221> NAME/KEY: PRM9t
<222> LOCATION: (5934)..(6471)
<220> FEATURE:
<221> NAME/KEY: LTP2
<222> LOCATION: (6472)..(6511)

<400> SEQUENCE: 2
taaccctcac taaagggaac aaaagctgga gctcgtttaa acggcgcgcc caccggagct      60
tggatatgat aaacgaaata ttcttgaatc gtgagatcgc ctgttttcaa aaccgttgga     120
ggcagaaaca attttgtcac aagatgggca ttctaccccca tccttgctgt attattgtag    180
tctcgctttc ttttatgctg acaaatgag actactgcac attttatac gttcttggtt       240
ttttttaaag gtgtggtttc ggcattatcc tgccgcacgt ttcttggata attcatcctg     300
attctctatt ttaaacgctt cagcctatca ggatttggtt ttgatacata ctgcaagagt     360
gtatctcggg aacagtcatt tattccgcaa caaacttaat tgcggaacgc gttaggcgat     420
ttctagcata tatcaaatac cgttcgcgat ttcttctggg ttcgtctctt ttctttttaaa    480
tacttattaa cgtactcaaa caactacact tcgttgtatc tcagaatgag atccctcagt     540
atgacaatac atcattctaa acgttcgtaa acacatatg aaacaacttt ataacaaagc      600
gaacaaaatg ggcaacatga gatgaaactc cgcgtccctt agctgaacta cccaaacgta     660
cgaatgcctg aacaattagt ttagatccga gattccgcgc ttccatcatt tagtataatc     720
catatttat ataatatata ggataagtaa cagcccgcga aaaacaacaa ataatcataa       780
aaattttaga actagacata tcgagtttat cattatcaat actgccatt caaagaatac      840
gtaaataatt aatagtagtg attttcctaa ctttatttag tcaaaaaatt agcctttaa      900
ttctgctgta acccgtacat gcccaaaata ggggcgggt tacacagaat atataacatc      960
gtaggtgtct gggtgaacag tttattcctg gcatccacta aatataatgg agcccgcttt    1020
ttaagctggc atccagaaaa aaaagaatc ccagcaccaa aatattgttt tcttcaccaa      1080
ccatcagttc ataggtccat tctcttagcg caactacaga gaacagggc acaaacaggc     1140
aaaaaacggg cacaacctca atggagtgat gcaacctgcc tggagtaaat gatgacacaa    1200
ggcaattgac ccacgcatgt atctatctca tttcttaca ccttctatta ccttctgctc      1260
tctctgattt ggaaaaagct gaaaaaaaag gttgaaacca gttccctgaa attattcccc    1320
tacttgacta ataagtatat aaagacggta ggtattgatt gtaattctgt aaatctattt    1380
cttaaacttc ttaaattcta cttttatagt tagtctttt tttagtttta aaacaccaag      1440
aacttagttt cgactagaaa atttattata aaaggaagag aaataattaa acaatgacta    1500
agctacactt tgacactgct gaaccagtca agatcacact tccaaatggt ttgacatacg    1560
agcaaccaac cggtctattc attaacaaca agtttatgaa agctcaagac ggtaagacct    1620
atcccgtcga agatccttcc actgaaaaca ccgtttgtga ggtctcttct gccaccactg    1680
aagatgttga atatgctatc gaatgtgccg accgtgcttt ccacgacact gaatgggcta    1740
cccaagaccc aagagaaaga ggccgtctac taagtaagtt ggctgacgaa ttggaaagcc    1800
aaattgactt ggtttcttcc attgaagctt tggacaatgg taaaactttg gccttagccc    1860
gtgggatgt taccattgca atcaactgtc taagagatgc tgctgcctat gccgacaaag    1920
tcaacggtag aacaatcaac accggtgacg gctacatgaa cttcaccacc ttagagccaa    1980
```

```
tcggtgtctg tggtcaaatt attccatgga actttccaat aatgatgttg gcttggaaga    2040
tcgccccagc attggccatg ggtaacgtct gtatcttgaa acccgctgct gtcacacctt    2100
taaatgccct atactttgct tctttatgta agaaggttgg tattccagct ggtgtcgtca    2160
acatcgttcc aggtcctggt agaactgttg gtgctgcttt gaccaacgac caagaatca     2220 gaaagctggc ttttaccggt tctacagaag tcggtaagag tgttgctgtc gactcttctg    2280
aatctaactt gaagaaaatc actttggaac taggtggtaa gtccgcccat ttggtctttg    2340
acgatgctaa cattaagaag actttaccaa atctagtaaa cggtattttc aagaacgctg    2400
gtcaaatttg ttcctctggt tctagaattt acgttcaaga aggtatttac gacgaactat    2460
tggctgcttt caaggcttac ttggaaaccg aaatcaaagt tggtaatcca tttgacaagg    2520
ctaacttcca aggtgctatc actaaccgtc aacaattcga cacaattatg aactacatcg    2580
atatcggtaa gaaagaaggc gccaagatct taactggtgg cgaaaaagtt ggtgacaagg    2640
gttacttcat cagaccaacc gttttctacg atgttaatga agacatgaga attgttaagg    2700
aagaaatttt tggaccagtt gtcactgtcg caaagttcaa gactttagaa gaaggtgtcg    2760
aaatggctaa cagctctgaa ttcggtctag gttctatggg tatcgaaaca gaatctttga    2820
gcacaggttt gaaggtggcc aagatgttga aggccggtac cgtctggatc aacacataca    2880
acgattttga ctccagagtt ccattcggtg gtgttaagca atctggttac ggtagagaaa    2940
tgggtgaaga agtctaccat gcatacactg aagtaaaagc tgtcagaatt aagttgtaaa    3000
gacataaaac tgaaacaaca ccaattaata atagactttt ggacttcttc gccagaggtt    3060
tggtcaagtc tccaatcaag gttgtcggct tgtctaccct gccagaaatt tacgaaaaga    3120
tggaaaaggg tcaaatcgtt ggtagatacg ttgttgacac ttctaaataa gcgaatttct    3180
tatgatttat gattttattt attaaataag ttataaaaaa aataagtgta tacaaatttt    3240
aaagtgactc ttaggtttta aaacgaaaat tcttattctt gagtaactct ttcctgtagg    3300
tcaggttgct ttctcaggta tagcatgagg tcgctcttat tgaccacacc tctaccggca    3360
tggcttaaat aacatactca tcactaaaca ttcttaacaa tcaaagcaac aggcgcgttg    3420 gactttaat tttcgaggac cgcgaatcct tacatcacac ccaatccccc acaagtgatc      3480
ccccacacac catagcttca aaatgttttct actccttttt tactcttcca gattttctcg    3540
gactccgcgc atcgccgtac cacttcaaaa cacccaagca cagcatacta aatttcccct    3600
ctttcttcct ctagggtgtc gttaattacc cgtactaaag gtttggaaaa gaaaaaagag    3660
accgcctcgt ttcttttttct tcgtcgaaaa aggcaataaa aattttatc acgtttcttt    3720 ttcttgaaaa tttttttttt tgattttttt ctctttcgat gacctcccat tgatatttaa    3780
gttaataaac ggtcttcaat ttctcaagtt tcagtttcat ttttcttgtt ctattacaac    3840 ttttttttact tcttgctcat tagaaagaaa gcatagcaat ctaatctaag ttttaataca    3900
tctaccagtc aacagccaac aattaactaa ttaaacaatg tcccaaactc ataagcacgc    3960
tattccagct aatattgctg atagatgctt gatcaaccca gaacagtacg aaactaagta    4020
caagcaatcc atcaacgatc cagatacttt ttggggtgaa caaggtaaga ttttggattg    4080
gattacccca taccaaaagg tcaagaatac ttcttttgct ccaggcaacg tttccattaa    4140
gtggtatgaa gatggtactt tgaacttggc tgctaactgt ttggatagac acttgcaaga    4200
aaacggtgat agaaccgcta ttatttggga aggtgatgat acctcccaat ccaaacatat    4260
ctcttacaga gaattgcaca gagatgtctg tagattcgct aacactttgt tggatttggg    4320
```

```
catcaaaaag gggtgatgttg ttgctatcta tatgccaatg gttcctgaag ctgctgttgc   4380
tatgttggct tgtgctagaa ttggtgctgt tcattctgtt attttcggtg gttttttcacc  4440
agaagctgtt gccggtagaa ttatcgattc ttcatccaga ttggttatca ccgctgatga   4500
aggtgttaga gctggtagat ctattccatt gaaaaagaac gttgatgacg ccttgaagaa   4560
cccaaatgtt acttctgttg aacacgtcat cgttttgaag agaactggtt ctgatatcga   4620
ttggcaagag ggtagagatt tgtggtggag agatttgatt gaaaaggctt ctccagaaca   4680
tcaaccagaa gctatgaacg ctgaagatcc tttgtttatc ttgtacactt ctggttctac   4740
tggtaagcca aaaggtgttt tacacactac tggtggttat ttggtttacg ctgctactac   4800
tttcaagtac gttttcgatt atcacccagg tgatatctat tggtgtactg ctgatgttgg   4860
ttgggttact ggtcattctt atttgttgta tggtccattg gcttgtggtg ctactacatt   4920
gatgtttgaa ggtgttccaa attggccaac tccagctaga atgtgtcaag ttgttgacaa   4980
acaccaagtc aacatcttgt atactgctcc aactgctatt agagctttga tggctgaagg   5040
tgataaggct attgaaggta ctgatagatc ctccttgaga atcttgggtt ctgttggtga   5100
acctattaac cctgaagcct gggaatggta ttggaagaaa attggtaaag aaaagtgccc   5160
agttgttgat acttggtggc aaactgaaac tggtggtttt atgattactc cattgccagg   5220
tgctattgaa ttgaaagctg ttctgctac tagaccattt tttggtgttc aaccagcttt    5280
ggttgataac gaaggtcatc cacaagaagg tgctactgaa ggtaatttgg ttattactga   5340
ttcttggcca ggtcaagcta gaactttgtt tggtgatcac gaaagattcg aacagactta   5400
cttctctacc ttcaagaaca tgtacttctc tggtgatggt gctagaagag atgaagatgg   5460
ttactattgg attaccggta gagttgatga tgtcttgaat gtttctggtc acagattagg   5520
tactgccgaa attgaatctg ctttggttgc tcatccaaag attgctgaag ctgcagttgt   5580
tggtattcca catgctatta agggtcaagc tatctacgct tacgttactt tgaatcatgg   5640
tgaagaacca tctccagaat tatacgctga agttagaaac tgggtcagaa aagaaattgg   5700
tccattagct accccagatg ttttacattg gactgattct tgccaaagac cagatcagg    5760
taagatcatg agaagaatct tgagaaagat tgctgctggt gatacttcta acttgggtga   5820
tacttcaaca ttagctgatc caggtgttgt tgaaaagcct ttggaagaaa aacaagctat   5880
tgccatgcca tcctaataat taaatactat tttcaaaatt ctacttaaaa ataacagaag   5940
acgggagaca ctagcacaca actttaccag gcaaggtatt tgacgctagc atgtgtccaa   6000
ttcagtgtca tttatgattt tttgtagtag gatataaata tatacagcgc tccaaatagt   6060
gcggttgccc caaaacacc acggaacctc atctgttctc gtactttgtt gtgacaaagt    6120
agctcactgc cttattatca cattttcatt atgcaacgct tcggaaaata cgatgttgaa   6180
aatgcctcta gagatgaaaa acaatcgtaa aagggtcctg cgtaattgaa acatttgatc   6240
agtatgcagt ggcacagaaa caaccaggaa tactatagtc ataggcaata caaggtatat   6300
attggctatg cagacccctc cagaaagtac cgacgtcaag ttagatacac ttaacgaacc   6360
tagtgcacat ttaattgaga aaaatgtggc tcttcctaag gacatattcc gttcgtactt   6420
gagttattgg atctatgaaa tcgctcgcta tacaccagtc atgattttgt cattgcgaag   6480
actatactga tatatgaatt taaactagag cggaccaact atcatccgct aattactgac   6540
attaccaaat gagatctgtg aatgggcaag ataaaaaaca aaaattgaaa tgtttgacgt   6600
tatgtaaaac tattaattcc ttcgctttcg gcggtcacag aatttgcgtg tagctgactc   6660
ttgttcaatc aatatcattt gttactttat ttgaaagtct gtattactgc gcctattgtc   6720
```

-continued

```
atccgtacca aagaacgtca aaaagaaaca agataatttt tgtgcttaca ccatttatag    6780
atcactgagc ccagaatatc gctggagctc agtgtaagtg gcatgaacac aactctgact    6840
gatcgcacat attgccgtta tcataaatac tagttgtact tgtcaatgcg acgaatggca    6900
tcatgcctat tattacgttc ctcttttcc gtttcatgtt tccagaatgc tattgaatct    6960
aacacttcaa ttataaaaaa gaataaatcc gcaataattt taggctaatt gttgtactgt    7020
caagcgaacc taatggttaa aattcagagg aaccttcgac gtagtctgat cgctacttct    7080
atatcttatg ttcccagtca atcaaaagtt gatactataa tagctgccat ttatacctgt    7140
tagttatggc gatcgtttat cacggcggcc gcggtaccta ataacttcgt atagcataca    7200
ttatacgaag ttatattaag ggttctcgac gttttcgaca ctggatggcg gcgttagtat    7260
cgaatcgaca gcagtatagc gaccagcatt cacatacgat tgacgcatga tattactttc    7320
tgcgcactta acttcgcatc tgggcagatg atgtcgaggc gaaaaaaaat ataaatcacg    7380
ctaacatttg attaaaatag aacaactaca atataaaaaa actatacaaa tgacaagttc    7440
ttgaaaacaa gaatcttttt attgtcagta ctgattagaa aaactcatcg agcatcaaat    7500
gaaactgcaa tttattcata tcaggattat caataccata tttttgaaaa agccgtttct    7560
gtaatgaagg agaaaactca ccgaggcagt tccataggat ggcaagatcc tggtatcggt    7620
ctgcgattcc gactcgtcca acatcaatac aacctattaa tttcccctcg tcaaaaataa    7680
ggttatcaag tgagaaatca ccatgagtga cgactgaatc cggtgagaat ggcaaaagct    7740
tatgcatttc tttccagact tgttcaacag gccagccatt acgctcgtca tcaaaatcac    7800
tcgcatcaac caaaccgtta ttcattcgtg attgcgcctg agcgagacga atacgcgat    7860 cgctgttaaa aggacaatta caaacaggaa tcgaatgcaa ccggcgcagg aacactgcca    7920
gcgcatcaac aatattttca cctgaatcag gatattcttc taatacctgg aatgctgttt    7980
tgccggggat cgcagtggtg agtaaccatg catcatcagg agtacggata aaatgcttga    8040
tggtcggaag aggcataaat tccgtcagcc agtttagtct gaccatctca tctgtaacat    8100
cattggcaac gctacctttg ccatgtttca gaaacaactc tggcgcatcg gcttcccat    8160 acaatcgata gattgtcgca cctgattgcc cgacattatc gcgagcccat ttatacccat    8220
ataaatcagc atccatgttg gaatttaatc gcggcctcga acgtgagtc ttttccttac    8280 ccatggttgt ttatgttcgg atgtgatgtg agaactgtat cctagcaaga ttttaaaagg    8340
aagtatatga aagaagaacc tcagtggcaa atcctaacct tttatatttc tctacagggg    8400
cgcggcgtgg ggacaattca acgcgtctgt gaggggagcg tttccctgct cgcaggtctg    8460
cagcgaggag ccgtaatttt tgcttcgcgc cgtgcggcca tcaaaatgta tggatgcaaa    8520
tgattataca tggggatgta tgggctaaat gtacgggcga cagtcacatc atgcccctga    8580
gctgcgcacg tcaagactgt caaggagggt attctgggcc tccatgtcgc tggccgggtg    8640
acccggcggg gacgaggcaa gctaaacaga tctctagacc taataacttc gtatagcata    8700
cattatacga agttatatta agggttgtct taattaaggg tgcccaattc gccctatagt    8760
gagtcgtatt acgcgcgctc actggccgtc gttttacaac gtcgtgactg ggaaaaccct    8820
ggcgttaccc aacttaatcg ccttgcagca catcccccct tcgccagctg gcgtaatagc    8880
gaagaggccc gcaccgatcg cccttcccaa cagttgcgca gcctgaatgg cgaatggcgc    8940
gacgcgccct gtagcggcgc attaagcgcg gcgggtgtgg tggttacgcg cagcgtgacc    9000
gctacacttg ccagcgccct agcgcccgct cctttcgctt tcttcccttc ctttctcgcc    9060
```

-continued

```
acgttcgccg gctttccccg tcaagctcta aatcgggggc tcccttttagg gttccgattt    9120
agtgctttac ggcacctcga ccccaaaaaa cttgattagg gtgatggttc acgtagtggg    9180
ccatcgccct gatagacggt ttttcgccct ttgacgttgg agtccacgtt ctttaatagt    9240
ggactcttgt tccaaactgg aacaacactc aaccctatct cggtctattc ttttgattta    9300
taagggattt tgccgatttc ggcctattgg ttaaaaaatg agctgattta acaaaaattt    9360
aacgcgaatt ttaacaaaat attaacgttt acaatttcct gatgcggtat tttctcctta    9420
cgcatctgtg cggtatttca caccgcatag atccgtcgag ttcaagagaa aaaaaaagaa    9480
aaagcaaaaa gaaaaaagga aagcgcgcct cgttcagaat gacacgtata gaatgatgca    9540
ttaccttgtc atcttcagta tcatactgtt cgtatacata cttactgaca ttcataggta    9600
tacatatata cacatgtata tatatcgtat gctgcagctt taaataatcg gtgtcaatgt    9660
ctgcccctat gtctgcccct aagaagatcg tcgttttgcc aggtgaccac gttggtcaag    9720
aaatcacagc cgaagccatt aaggttctta aagctatttc tgatgttcgt tccaatgtca    9780
agttcgattt cgaaaatcat ttaattggtg gtgctgctat cgatgctaca ggtgtcccac    9840
ttccagatga ggcgctggaa gcctccaaga aggttgatgc cgttttgtta ggtgctgtgg    9900
gtggtcctaa atggggtgcc ggtagtgtta gacctgaaca aggtttacta aaaatccgta    9960
aagaacttca attgtacgcc aacttaagac catgtaactt tgcatccgac tctcttttag   10020
acttatctcc aatcaagcca caatttgcta aaggtactga cttcgttgtt gtcagagaat   10080
tagtgggagg tatttacttt ggtaagagaa aggaagacga tggtgatggt gtcgctttggg  10140
atagtgaaca atacaccgtt ccagaagtgc aaagaatcac aagaatggcc gctttcatgg   10200
ccctacaaca tgagccacca ttgcctattt ggtccttgga taaagctaat gttttggcct   10260
cttcaagatt atggagaaaa actgtggagg aaaccatcaa gaacgaattc cctacattga   10320
aggttcaaca tcaattgatt gattctgccg ccatgatcct agttaagaac ccaacccacc   10380
taaatggtat tataatcacc agcaacatgt ttggtgatat catctccgat gaagcctccg   10440
ttatcccagg ttccttgggt ttgttgccat ctgcgtcctt ggcctctttg ccagacaaga   10500
acaccgcatt tggtttgtac gaaccatgcc acggttctgc tccagatttg ccaagaata    10560
aggttgaccc tatcgccact atcttgtctg ctgcaatgat gttgaaattg tcattgaact   10620
tgcctgaaga aggtaaggcc attgaagatg cagttaaaaa ggttttggat gcaggtatca   10680
gaactggtga tttaggtggt tccaacagta ccaccgaagt cggtgatgct gtcgccgaag   10740
aagttaagaa aatccttgct taactttgcc ttcgtttatc ttgcctgctc atttttttagt   10800
atattcttcg aagaaatcac attactttat ataatgtata attcattatg tgataatgcc   10860
aatcgctaag aaaaaaaaag agtcatccgc taggggaaaa aaaaaatga aaatcattac   10920
cgaggcataa aaaatatag agtgtactag aggaggccaa gagtaataga aaagaaaat    10980
tgcgggaaag gactgtgtta tgacttccct gactaatgcc gtgttcaaac gatacctggc   11040
agtgactcct agcgctcacc aagctcttaa aacgggaatt tatggtgcac tctcagtaca   11100
atctgctctg atgccgcata gttaagccag ccccgacacc cgccaacacg cgctgacgcg   11160
ccctgacggg cttgtctgct cccggcatcc gcttacagac aagctgtgac cgtctccggg   11220
agctgcatgt gtcagaggtt ttcaccgtca tcaccgaaac gcgcgagacg aaagggcctc   11280
gtgatacgcc tatttttata ggttaatgtc atgataataa tggtttctta ggacggatcg   11340
cttgcctgta acttacacgc gcctcgtatc ttttaatgat ggaataattt gggaatttac   11400
tctgtgttta tttattttta tgttttgtat ttggatttta gaaagtaaat aaagaaggta   11460
```

```
gaagagttac ggaatgaaga aaaaaaaata aacaaaggtt taaaaaattt caacaaaaag  11520
cgtactttac atatatattt attagacaag aaaagcagat taaatagata tacattcgat  11580
taacgataag taaaatgtaa aatcacagga ttttcgtgtg tggtcttcta cacagacaag  11640
atgaaacaat tcggcattaa tacctgagag caggaagagc aagataaaag gtagtatttg  11700
ttggcgatcc ccctagagtc ttttacatct tcggaaaaca aaaactattt tttctttaat  11760
ttcttttttt actttctatt tttaatttat atatttatat taaaaaattt aaattataat  11820
tatttttata gcacgtgatg aaaaggaccc aggtggcact tttcggggaa atgtgcgcgg  11880 aaccctatt tgtttatttt tctaaataca ttcaaatatg tatccgctca tgagacaata  11940
accctgataa atgcttcaat aatattgaaa aggaagagt atgagtattc aacatttccg  12000
tgtcgccctt attccctttt ttgcggcatt ttgccttcct gttttgctc acccagaaac  12060 gctggtgaaa gtaaaagatg ctgaagatca gttgggtgca cgagtgggtt acatcgaact  12120
ggatctcaac agcggtaaga tccttgagag ttttcgcccc gaagaacgtt ttccaatgat  12180
gagcactttt aaagttctgc tatgtggcgc ggtattatcc cgtattgacg ccgggcaaga  12240
gcaactcggt cgccgcatac actattctca gaatgacttg gttgagtact caccagtcac  12300
agaaaagcat cttacggatg gcatgacagt aagagaatta tgcagtgctg ccataaccat  12360
gagtgataac actgcggcca acttacttct gacaacgatc ggaggaccga aggagctaac  12420
cgcttttttg cacaacatgg gggatcatgt aactcgcctt gatcgttggg aaccggagct  12480
gaatgaagcc ataccaaacg acgagcgtga ccaccacgatg cctgtagcaa tggcaacaac  12540
gttgcgcaaa ctattaactg gcgaactact tactctagct tcccggcaac aattaataga  12600
ctggatggag gcggataaag ttgcaggacc acttctgcgc tcggcccttc cggctggctg  12660
gtttattgct gataaatctg gagccggtga gcgtgggtct cgcggtatca ttgcagcact  12720
ggggccagat ggtaagccct cccgtatcgt agttatctac acgacgggga gtcaggcaac  12780 tatgatgaa cgaaatagac agatcgctga gataggtgcc tcactgatta gcattggta  12840 actgtcagac caagtttact catatatact ttagattgat ttaaaacttc attttttaatt  12900 taaaaggatc taggtgaaga tcctttttga atctcatg accaaaatcc cttaacgtga  12960
gttttcgttc cactgagcgt cagaccccgt agaaaagatc aaaggatctt cttgagatcc  13020 ttttttttctg cgcgtaatct gctgcttgca acaaaaaaa ccaccgctac cagcggtggt  13080
ttgtttgccg gatcaagagc taccaactct ttttccgaag gtaactggct tcagcagagc  13140
gcagatacca aatactgtcc ttctagtgta gccgtagtta ggccaccact tcaagaactc  13200
tgtagcaccg cctacatacc tcgctctgct aatcctgtta ccagtggctg ctgccagtgg  13260
cgataagtcg tgtcttaccg ggttggactc aagacgatag ttaccggata aggcgcagcg  13320
gtcgggctga acggggggtt cgtgcacaca gcccagcttg gagcgaacga cctacaccga  13380
actgagatac ctacagcgtg agctatgaga aagcgccacg cttcccgaag ggagaaaggc  13440
ggacaggtat ccggtaagcg gcagggtcgg aacaggagag cgcacgaggg agcttccagg  13500
gggaaacgcc tggtatcttt atagtcctgt cgggtttcgc cacctctgac ttgagcgtcg  13560
atttttgtga tgctcgtcag gggggcggag cctatgaaa aacgccagca acgcggcctt  13620
tttacggttc ctggcctttt gctggccttt tgctcacatg ttctttcctg cgttatcccc  13680
tgattctgtg gataaccgta ttaccgcctt tgagtgagct gataccgctc gccgcagccg  13740
aacgaccgag cgcagcgagt cagtgagcga ggaagcggaa gagcgcccaa tacgcaaacc  13800
```

```
gcctctcccc gcgcgttggc cgattcatta atgcagctgg cacgacaggt ttcccgactg    13860
gaaagcgggc agtgagcgca acgcaattaa tgtgagttac ctcactcatt aggcacccca    13920
ggctttacac tttatgcttc cggctcctat gttgtgtgga attgtgagcg ataacaatt     13980 tcacacagga aacagctatg accatgatta cgccaagcgc gcaat                    14025

<210> SEQ ID NO 3
<211> LENGTH: 684
<212> TYPE: DNA
<213> ORGANISM: Saccharomyces cerevisiae
<220> FEATURE:
<221> NAME/KEY: Acc1 promoter
<222> LOCATION: (1)..(463)
<220> FEATURE:
<221> NAME/KEY: gRNA_3
<222> LOCATION: (53)..(72)
<220> FEATURE:
<221> NAME/KEY: gRNA_2
<222> LOCATION: (265)..(284)
<220> FEATURE:
<221> NAME/KEY: gRNA_1
<222> LOCATION: (339)..(358)

<400> SEQUENCE: 3
ggtagaaact tgattttttc taattttctg cgctgtttcg ggaacggaaa aaaattaagc      60
tagaagacga atcggttatt atactattat atttgtatag tatagtagcg tgtcgtatcg    120
tatcgtgtcg tatcgtatcg tatcgttaaa agaaaataca cgaataaata ataatatgtg    180
gagaagaaaa agggaagttt cttgtctctt gctctgaatc tgaattccaa ttcaagttca    240
aattgttctc tagtttattg tccaaaaata aggatgaagc gggagggaag ggcagaggga    300
aaagttcgta tagtagaatg aataaacttt tataaacaca tgcaccgatc actcacagag    360
gataaaaaaa tggcacaaca aatatatata tatagatgca aatggcgatt gcaaattagg    420
gaattggctt tgttgttttt tatcttcagg taaactgtac gaaagggata aaaagagtag    480
aataaggaaa ggaaaattga agagagcaga acaattgtag aaccgataac aattgtgaca    540
gtgattgtgc taggctatac tgtgccagaa tacgactggg agtgctgttc ttcttatata    600
tcttggcgct gattgagcgt atagcctagt tcaccaagca gtagagagag tggcaatgag    660
cggttgaatt tcgactgcga cttg                                            684

<210> SEQ ID NO 4
<211> LENGTH: 971
<212> TYPE: DNA
<213> ORGANISM: Artificial Sequence
<220> FEATURE:
<223> OTHER INFORMATION: PGK1 promoter and integration sequences for
     Saccharomyces cerevisiae Acc1 promoter
<220> FEATURE:
<221> NAME/KEY: PGK1p
<222> LOCATION: (7)..(750)

<400> SEQUENCE: 4
tgttttatat ttgttgtaaa aagtagataa ttacttcctt gatgatctgt aaaaaagaga     60
aaaagaaagc atctaagaac ttgaaaaact acgaattaga aagaccaaa tatgtatttc     120 ttgcattgac caatttatgc aagtttatat atatgtaaat gtaagtttca cgaggttcta    180
ctaaactaaa ccaccccctt ggttagaaga aaagagtgtg tgagaacagg ctgttgttgt    240
cacacgattc ggacaattct gtttgaaaga gagagagtaa cagtacgatc gaacgaactt    300
tgctctggag atcacagtgg gcatcatagc atgtggtact aaacccttc ccgccattcc     360 agaaccttcg attgcttgtt acaaaacctg tgagccgtcg ctaggacctt gttgtgtgac    420
```

```
gaaattggaa gctgcaatca ataggaagac aggaagtcga gcgtgtctgg gttttttcag      480
ttttgttctt tttgcaaaca aatcacgagc gacggtaatt tctttctcga taagaggcca      540
cgtgctttat gagggtaaca tcaattcaag aaggagggaa acacttcctt tttctggccc      600
tgataatagt atgagggtga agccaaaata aaggattcgc gcccaaatcg gcatctttaa      660
atgcaggtat gcgatagttc ctcactcttt ccttactcac gagtaattct tgcaaatgcc      720
tattatgcag atgttataat atctgtgcgt agggataaaa agagtagaat aaggaaagga      780
aaattgaaga gagcagaaca attgtagaac cgataacaat tgtgacagtg attgtgctag      840
gctatactgt gccagaatac gactgggagt gctgttcttc ttatatatct tggcgctgat      900
tgagcgtata gcctagttca ccaagcagta gagagagtgg caatgagcgg ttgaatttcg      960
actgcgactt g                                                           971

<210> SEQ ID NO 5
<211> LENGTH: 1724
<212> TYPE: DNA
<213> ORGANISM: Artificial Sequence
<220> FEATURE:
<223> OTHER INFORMATION: Cassette with Saccharomyces cerevisiae Acc1
      (S659A; S1157A) coding sequence, regulatory sequences and
      integration sequences
<220> FEATURE:
<221> NAME/KEY: T-G Ser659Ala
<222> LOCATION: (108)..(108)
<220> FEATURE:
<221> NAME/KEY: T-G Ser1157Ala
<222> LOCATION: (1602)..(1602)

<400> SEQUENCE: 5
ggcgcgccga gggtaaaaga tacaagttca cggtcgctaa atccggtaat gaccgctaca       60
cattatttat caatggttct aaatgtgata tcatactgcg tcaactagct gatggtgggc      120
tgctgatcgc tatcggcgct aaatcgcata ccatctattg gaaagaagaa gttgctgcta      180
caagattatc cgttgactct atgactactt tgttggaagt tgaaaacgat ccaacccagt      240
tgcgtactcc atcccctggt aaaattggtt aaattcttggt ggaaaatggt gaacacatta      300
tcaagggcca accatatgca gaaattgaag ttatgaaaat gcaaatgcct ttggtttctc      360
aagaaaatgg tatcgtccag ttattaaagc aacctggttc taccattgtt gcaggtgata      420
tcatggctat tatgactctt gacgatccat ccaaggtcaa gcacgctcta ccatttgaag      480
gtatgctgcc agattttggt tctccagtta tcgaaggaac caaacctgcc tataaattca      540
agtcattagt gtctactttg gaaaacattt tgaaggtta tgcaaccaa gttattatga      600 acgcttcctt gcaacaattg atagaagttt tgagaaatcc aaaactgcct tactcagaat      660
ggaaactaca catctctgct ttacattcaa gattgcctgc taagctagat gaacaaatgg      720
aagagttagt tgcacgttct ttgagacgtg gtgctgtttt cccagctaga caattaagta      780
aattgattga tatggccgtg aagaatcctg aatacaaccc cgacaaattg ctgggcgcag      840
tcgtggaacc attggcggat attgctcata gtactctaa cgggttagaa gcccatgaac      900
attctatatt tgtccatttc ttggaagaat attacgaagt tgaaaagtta ttcaatggtc      960
caaatgttcg tgaggaaaat atcattctga aattgcgtga tgaaacccct aaagatctag     1020
ataaagttgc gctaactgtt ttgtctcatt cgaaagtttc agcgaagaat aacctgatcc     1080
tagctatctt gaaacattat caaccattgt gcaagttatc ttctaaagtt tctgccattt     1140
tctctactcc tctacaacat attgttgaac tagaatctaa ggctaccgct aaggtcgctc     1200
```

-continued

```
tacaagcaag agaaattttg attcaaggcg ctttaccttc ggtcaaggaa agaactgaac    1260
aaattgaaca tatcttaaaa tcctctgttg tgaaggttgc ctatggctca tccaatccaa    1320
agcgctctga accagatttg aatatcttga aggacttgat cgattctaat tacgttgtgt    1380
tcgatgtttt acttcaattc ctaacccatc aagacccagt tgtgactgct gcagctgctc    1440
aagtctatat tcgtcgtgct tatcgtgctt acaccatagg agatattaga gttcacgaag    1500
gtgtcacagt tccaattgtt gaatggaaat tccaactacc ttcagctgcg ttctccacct    1560
ttccgactgt gaagtctaag atgggtatga acagggctgt tgctgtttca gatttgtcat    1620
atgttgcaaa cagtcagtca tctccgttaa gagaaggtat tttgatggct gtggatcatt    1680
tagatgatgt tgatgaaatt ttgtcacaaa gtttggggcg cgcc                    1724
```

<210> SEQ ID NO 6
<211> LENGTH: 3256
<212> TYPE: DNA
<213> ORGANISM: Artificial Sequence
<220> FEATURE:
<223> OTHER INFORMATION: Cassette with Saccharomyces cerevisiae Maf1
      coding sequence, regulatory sequences and integration sequences
<220> FEATURE:
<221> NAME/KEY: L0
<222> LOCATION: (362)..(401)
<220> FEATURE:
<221> NAME/KEY: Tef1
<222> LOCATION: (402)..(895)
<220> FEATURE:
<221> NAME/KEY: L1
<222> LOCATION: (896)..(935)
<220> FEATURE:
<221> NAME/KEY: MAF1
<222> LOCATION: (936)..(2123)
<220> FEATURE:
<221> NAME/KEY: L2
<222> LOCATION: (2124)..(2163)
<220> FEATURE:
<221> NAME/KEY: PRM9t
<222> LOCATION: (2164)..(2701)
<220> FEATURE:
<221> NAME/KEY: LTP2
<222> LOCATION: (2702)..(2741)

<400> SEQUENCE: 6

```
aatgatttaa gcgtgcgtga agataacact acaatccatt ttaaagcaac atccacattg     60
agtgtataca ccacaaaggt tttttcaggg cgttttttctc gccactttat gttgaccaaa    120
attattaatg gaacttacaa cgtttccaaa agttagttaa atacatacgt ctatttacta    180
agcaagaaat atatcatgac aagcccaaat attatattgt tatgtttaca aaaaaaaat     240 ggctatatac atcaagtctg gaggcttttt ataacaagca agtggggtaa cttagacata    300
agattgactt ctttgaattc aacaaaaata catactttg atgatttcaa tggtagaagc     360
ataaacaaca aataatcata aaaattttag aactagacat aaagcaacag gcgcgttgga    420
cttttaattt tcgaggaccg cgaatcctta catcacaccc aatcccccac aagtgatccc    480
ccacacacca tagcttcaaa atgtttctac tcctttttta ctcttccaga ttttctcgga    540
ctccgcgcat cgccgtacca cttcaaaaca cccaagcaca gcatactaaa tttcccctct    600
ttcttcctct agggtgtcgt taattacccg tactaaaggt ttggaaaaga aaaaagagac    660
cgcctcgttt cttttttcttc gtcgaaaaag gcaataaaaa tttttatcac gtttcttttt    720
cttgaaaatt tttttttttg atttttttct cttcgatga cctcccattg atatttaagt    780
taataaacgg tcttcaattt ctcaagtttc agtttcattt ttcttgttct attacaactt    840
tttttacttc ttgctcatta gaaagaaagc atagcaatct aatctaagtt ttaatctaga    900
```

```
aaatttatta taaaaggaag agaaataatt aaacaatgaa atttattgat gagctagata    960
tagagagagt gaatcaaact ctcaatttcg agacaaatga ctgtaaaatc gtgggcagtt   1020
gcgatatttt cacaacaaag gcggttgcat cagatagaaa attatataaa actattgatc   1080
agcatttgga tactatttta caggaaaatg agaattacaa tgctacccct cagcaacagc   1140
tagctgctcc cgaaacaaac caatcaccct gctcgtcgcc attttattct aataggaggg   1200
atagcaactc ttttttggga gcaaaagagaa gaatatcttt tagtgaatac aatagcaata   1260
ataacactaa caacagtaat ggcaatagca gtaataacaa taactattct ggacctaatg   1320
gttcttctcc agcaactttt cccaaaagtg ccaagctaaa tgaccaaaat ttaaaagaat   1380
tagtctcgaa ttacgattct ggctctatga gctcatcgtc tcttgattct tcttctaaga   1440
atgatgagag gataagaaga aggagcagta gcagtattag cagtttcaaa agtggtaaat   1500
catcgaacaa taattacagt tctggtacag caaccaacaa tgttaacaaa agaagaaaat   1560
cttcgataaa cgaaaggcca agcaatttaa gtttgggtcc gtttggtccc ataaacgaac   1620
cgtcaagccg caaaatattt gcttatctga ttgctatcct caacgcttct tatcctgacc   1680 atgattttc atcggttgag ccaacggatt ttgtcaaaac atcattgaaa acttttattt   1740
ccaaatttga aaacacctta tattctcttg gtagacaacc agaggaatgg gtctgggagg   1800
taattaattc tcacatgact cttttctgatt gcgtcctttt tcaatattca ccttcaaact   1860
cttttttgga agatgagcct ggctatcttt ggaatcttat aggttttctt tacaacagga   1920
aaaggaaaag agtggcttac ctttacttga tttgctcgcg tctaaattcg agtacaggcg   1980
aagtggaaga tgccttggca aaaaaacctc agggaaagct tataatagat gatggctcaa   2040
atgaatacga aggagaatac gatttcactt atgatgagaa tgtaatagat gataaatcag   2100
atcaagaaga atccctacag tagagacata aaactgaaac aacaccaatt aataatagac   2160
tttacagaag acgggagaca ctagcacaca actttaccag gcaaggtatt tgacgctagc   2220
atgtgtccaa ttcagtgtca tttatgattt tttgtagtag gatataaata tatacagcgc   2280
tccaaatagt gcggttgccc caaaaacacc acgaacctc atctgttctc gtactttgtt   2340
gtgacaaagt agctcactgc cttattatca cattttcatt atgcaacgct tcggaaaata   2400
cgatgttgaa aatgcctcta gagatgaaaa acaatcgtaa aagggtcctg cgtaattgaa   2460
acatttgatc agtatgcagt ggcacagaaa caaccaggaa tactatagtc ataggcaata   2520
caaggtatat attggctatg cagacccctc cagaaagtac cgacgtcaag ttagatacac   2580
ttaacgaacc tagtgcacat ttaattgaga aaaatgtggc tcttcctaag gacatattcc   2640
gttcgtactt gagttattgg atctatgaaa tcgctcgcta tacaccagtc atgattttgt   2700
ccttaaataa catactcatc actaaacatt cttaacaatc agaaaacaac gcgtcatgaa   2760
aaagagttac tgaaccttca gatcctactt attgtaatgc ttcgcgacat ccaatccatt   2820
taataatcaa tttaaaacta gagttggtag agttccttgt tgaacgtgat aacccaaaag   2880
cataatacga gtaatgtttc agtattgcta ttatatgttt acacaaggaa aacatataat   2940
aacaaacctc taatccggta gtacttaaga aactatagtt tctatgtaca aaaaggtaac   3000
tatgtaattc ttacatttac ataacgtata gaagggtcca ataaacttac taaacttact   3060
accttgttgt atataggcta gatcgtaatc cactacgtca acataaaaaa aacttaagaa   3120
gtttgaattt tatgtacaaa cagattgtta aaatataata taagattatg gaaacgaact   3180
tgctctaaaa aaaatttaaa gttttataaa atcctcgaac tatcgctgtt atacatgatg   3240
```

-continued

```
tccccaaagc gtgtac                                                    3256
```

<210> SEQ ID NO 7
<211> LENGTH: 4662
<212> TYPE: DNA
<213> ORGANISM: Artificial Sequence
<220> FEATURE:
<223> OTHER INFORMATION: Cassette with Saccharomyces cerevisiae
      UPC2E888D coding sequence, regulatory sequences and integration
      sequences
<220> FEATURE:
<221> NAME/KEY: L0
<222> LOCATION: (401)..(440)
<220> FEATURE:
<221> NAME/KEY: Tef1
<222> LOCATION: (441)..(934)
<220> FEATURE:
<221> NAME/KEY: L1
<222> LOCATION: (935)..(974)
<220> FEATURE:
<221> NAME/KEY: UPC2-1
<222> LOCATION: (975)..(3701)
<220> FEATURE:
<221> NAME/KEY: g-a G888D
<222> LOCATION: (3637)..(3637)
<220> FEATURE:
<221> NAME/KEY: L2
<222> LOCATION: (3702)..(3741)
<220> FEATURE:
<221> NAME/KEY: PRM9t
<222> LOCATION: (3742)..(4279)
<220> FEATURE:
<221> NAME/KEY: LTP2
<222> LOCATION: (4280)..(4319)

<400> SEQUENCE: 7

```
cccagttgtt tgtagctggt tcatatttag cggcaattct ctgttgcgta aatgaaaata     60
ttaatgtaaa caaaaaaga ccaaaacatt ttagcagtgt aagaaggtgt actgatacaa    120
aatgtgttta gagtctactg atatgttact daccgttcgt tgggaaaaaa atactgtatc    180
atttattaat caaaagcgac ttttggtgga atattatgat atgtgttgtt aaaatatgac    240
gtaattttag aattgtctga ttcgtattca aatttggtga aggaataacg cagagttgac    300
aatttaatag aatggattaa tcgtaatttt cagaaacgta gaaaaagaaa acaattaaa    360
acattatatt aagattattg atttgccttt taagggtcca taaacaacaa ataatcataa    420
aaattttaga actagacata aagcaacagg cgcgttggac ttttaatttt cgaggaccgc    480
gaatccttac atcacaccca atcccccaca agtgatcccc cacacaccat agcttcaaaa    540
tgtttctact ccttttttac tcttccagat tttctcggac tccgcgcatc gccgtaccac    600
ttcaaaacac ccaagcacag catactaaat ttccctctt tcttcctcta gggtgtcgtt     660
aattacccgt actaaaggtt tggaaaagaa aaaagagacc gcctcgtttc ttttcttcg     720
tcgaaaaagg caataaaaat tttatcacg tttcttttc ttgaaaattt tttttttga     780
ttttttctc tttcgatgac ctcccattga tatttaagtt aataaacggt cttcaatttc    840
tcaagtttca gtttcatttt tcttgttcta ttacaacttt ttttacttct tgctcattag    900
aaagaaagca tagcaatcta atctaagttt taatctagaa aatttattat aaaaggaaga    960
gaaataatta acaatgagc gaagtcggta tacagaatca caagaaagcg gtgacaaaac   1020
ccagaagaag agaaaaagtc atcgagctaa ttgaagtgga cggcaaaaag gtgagtacga   1080
cttcaaccgg taaacgtaaa ttccataaca aatcaaagaa tgggtgcgat aactgtaaaa   1140
gaagaagagt taagtgtgat gaagggaagc cagcctgtag gaagtgcaca aatatgaagt   1200
tggaatgtca gtatacacca atccatttaa ggaaaggtag aggagcaaca gtagtgaagt   1260
```

```
atgtcacgag aaaggcagac ggtagcgtgg agtctgattc atcggtagat ttacctccta    1320
cgatcaagaa ggagcagaca ccgttcaatg atatccaatc agcggtaaaa gcttcaggct    1380
catccaatga ttcctttcca tcaagcgcct ctacaactaa gagtgagagc gaggaaaagt    1440
catcggcccc tatagaggac aaaaacaata tgactcctct aagtatgggc tccagggta     1500 ccatcaataa gaaagatatg atgaataact ttttctctca aaatggcact attggttttg    1560
gttctcctga aagattgaat tcaggtatcg atggcttact attaccgcca ttgccttctg    1620
gaaatatggg tgcgttccaa cttcagcaac agcagcaagt gcagcagcaa tctcaaccac    1680
agacccaagc gcagcaagca agtggaactc caaacgagag atatggttca ttcgatcttg    1740
cgggtagtcc tgcattgcaa tccacgggaa tgagcttatc aaatagtcta agcgggatgt    1800
tactatgtaa caggattcct tccggccaaa actacactca acaacaatta caatatcaat    1860
tacaccagca gctgcaattg caacagcatc agcaagttca gctgcagcag tatcaacaat    1920
tacgtcagga acaacaccaa caagttcagc aacaacaaca ggaacaactc cagcaatacc    1980
aacaacattt tttgcaacag cagcaacaag tactgcttca gcaagagcaa caacctaacg    2040
atgaggaagg tggcgttcag gaagaaaaca gcaaaaaggt aaaggaaggg cctttacaat    2100
cacaaacaag cgaaactact ttaaacagcg atgctgctac attcaagct gatgcattat     2160 ctcagttaag taagatgggg ctaagcctaa agtcgttaag tacctttcca acagctggta    2220
ttggtggtgt ttcctatgac tttcaggaac tgttaggtat taagtttcca ataaataacg    2280
gcaattcaag agctactaag gccagcaacg cagaggaagc tttggccaat atgcaagagc    2340
atcatgaacg tgcagctgct tctgtaaagg agaatgatgg tcagctctct gatacgaaga    2400
gtccagcgcc atcgaataac gcccaagggg gaagtgctag tattatggaa cctcaggcgg    2460
ctgatgcggt ttcgacaatg gcgcctatat caatgattga agaaacatg aacagaaaca     2520 gcaacatttc tccatcaacg ccctctgcag tgttgaatga taggcaagag atgcaagatt    2580
ctataagttc tctaggaaat ctgacaaaag cagccttgga gaacaacgaa ccaacgataa    2640
gtttacaaac atcacagaca gagaatgaag acgatgcatc gcggcaagac atgacctcaa    2700
aaattaataa cgaagctgac cgaagttctg tttctgctgg taccagtaac atcgctaagc    2760
ttttagatct ttctaccaaa ggcaatctga acctgataga catgaaactg tttcatcatt    2820
attgcacaaa ggtctggcct acgattacag cggccaaagt ttctgggcct gaaatatgga    2880
gggactacat accggagtta gcatttgact atccatttt aatgcacgct tgttggcat     2940 tcagtgccac ccatctttcg aggactgaaa ctggactgga gcaatacgtt tcatctcacc    3000
gcctagacgc tctgagatta ttaagagaag ctgttttaga aatatctgag aataacaccg    3060
atgcgctagt tgccagcgcc ctgatactaa tcatggactc gttagcaaat gctagtggta    3120
acggcactgt aggaaaccaa agtttgaata gcatgtcacc aagcgcttgg atctttcatg    3180 tcaaggtgc tgcaacaatt ttaaccgctg tgtggccttt gagtgaaaga tctaaatttc     3240
ataacattat atctgttgat cttagcgatt taggcgatgt cattaaccct gatgttggaa    3300
caattactga attggtatgt tttgatgaaa gtattgccga tttgtatcct gtcggcttag    3360
attcgccata tttgataaca ctagcttatt tagataaatt gcaccgtgaa aaaaaccagg    3420
gtgattttat tctgcgggta tttacatttc cagcattgct agacaagaca ttcctggcat    3480
tactgatgac aggtgattta ggtgcaatga gaattatgag atcatattat aaactacttc    3540
gaggatttgc cacagaggtc aaggataaag tctggtttct cgaaggagtc acgcaggtgc    3600
```

```
tgcctcaaga cgttgatgag tacaggggag gtggtgatat gcatatgatg ctaggattac    3660
catcgatgac aacaacaaat ttctctgatt tttcgttatg aagacataaa actgaaacaa    3720
caccaattaa taatagactt tacagaagac gggagacact agcacacaac tttaccaggc    3780
aaggtatttg acgctagcat gtgtccaatt cagtgtcatt tatgattttt tgtagtagga    3840
tataaatata tacagcgctc caaatagtgc ggttgcccca aaaacaccac ggaacctcat    3900
ctgttctcgt actttgttgt gacaaagtag ctcactgcct tattatcaca ttttcattat    3960
gcaacgcttc ggaaaatacg atgttgaaaa tgcctctaga gatgaaaaac aatcgtaaaa    4020
gggtcctgcg taattgaaac atttgatcag tatgcagtgg cacagaaaca accaggaata    4080
ctatagtcat aggcaataca aggtatatat tggctatgca gaccccctcca gaaagtaccg    4140 acgtcaagtt agatacactt aacgaaccta gtgcacattt aattgagaaa aatgtggctc    4200
ttcctaagga catattccgt tcgtacttga gttattggat ctatgaaatc gctcgctata    4260
caccagtcat gattttgtcc ttaaataaca tactcatcac taaacattct taacaatcac    4320
gatggatgat gattggttct tatcataatt tgatttcggc agaagcaata ttagaggtat    4380
tgttgtaacg aaattccaat gtcatctgct tagtattatt aatgttacct gcatattatc    4440
acatgccgct taaaaatgtg ttataagtat taaaatctag tgaaagttga aatgtaatct    4500
aataggataa tgaaacatat gaaacggaat gaggaataat cgttgtatta ctatgtagag    4560
atatcgattt cattttgagg attcctatat tcttggggag aacttctact atattctgta    4620
tacatgatat aatagccttt accaacaatg gaatgccaac aa                      4662
```

```
<210> SEQ ID NO 8
<211> LENGTH: 3564
<212> TYPE: DNA
<213> ORGANISM: Artificial Sequence
<220> FEATURE:
<223> OTHER INFORMATION: Cassette with Aspergillus nidulans NpgA coding
      sequence, regulatory sequences and integration sequences
<220> FEATURE:
<221> NAME/KEY: LTP1 (L0)
<222> LOCATION: (596)..(635)
<220> FEATURE:
<221> NAME/KEY: Tef1p
<222> LOCATION: (636)..(1129)
<220> FEATURE:
<221> NAME/KEY: L1
<222> LOCATION: (1130)..(1169)
<220> FEATURE:
<221> NAME/KEY: NpgA
<222> LOCATION: (1170)..(2201)
<220> FEATURE:
<221> NAME/KEY: L2
<222> LOCATION: (2205)..(2244)
<220> FEATURE:
<221> NAME/KEY: PRM9t
<222> LOCATION: (2245)..(2782)
<220> FEATURE:
<221> NAME/KEY: LTP2
<222> LOCATION: (2783)..(2822)

<400> SEQUENCE: 8
```

```
tcaatcaaag caacccacaa atcctaggct gaatcatgat atcgatggaa gcaatcaaca      60
attttatcaa gaccgcacca aagcacgact atctgacagg cggagttcat cattctggta     120
atgtagacgt gttacaatta agcggcaata aagaagatgg tagtttagta tggaaccata     180
cttttgttga tgtagacaac aatgtggtag ctaagtttga agacgctctc gaaaaacttg     240
aaagtttgca ccggcgctca tcctcatcca caggcaatga agaacacgct aacgtttaac     300
cgaggggagt cacttcataa tgatgtgaga aataagtgaa tattgtaata attgttggga     360
```

```
ctccattgtc aacaaaagct ataatgtagg tatacagtat atactagaag ttctcctcga    420
ggatcttgga atccacaaaa gggagtcgat aaatctatat aataaaaatt actttatctt    480
ctttcgtttt atacgttgtc gtttattatc ctattacgtt atcaatcttc gcatttcagc    540
tttcattaga tttgatgact gtttctcaaa ctttatgtca ttttcttaca ccgcataaac    600
aacaaataat cataaaaatt ttagaactag acataaagca acaggcgcgt tggactttta    660
attttcgagg accgcgaatc cttacatcac acccaatccc ccacaagtga tcccccacac    720
accatagctt caaaatgttt ctactccttt tttactcttc cagattttct cggactccgc    780
gcatcgccgt accacttcaa aacacccaag cacagcatac taaatttccc ctctttcttc    840
ctctagggtg tcgttaatta cccgtactaa aggtttggaa aagaaaaaag agaccgcctc    900
gtttcttttt cttcgtcgaa aaaggcaata aaaattttta tcacgtttct ttttcttgaa    960 aattttttt tttgattttt ttctctttcg atgacctccc attgatattt aagttaataa    1020
acggtcttca atttctcaag tttcagtttc atttttcttg ttctattaca acttttttta    1080
cttcttgctc attagaaaga aagcatagca atctaatcta agttttaatc tagaaaattt    1140
attataaaag gaagagaaat aattaaacaa tggttcaaga tacctcttct gcttctacct    1200
ctccaatttt gactagatgg tacattgata ccagaccatt gactgcttct actgctgctt    1260
tgccattatt ggaaacttta caaccagccg atcaaatctc cgttcaaaag tactatcact    1320
tgaaggacaa gcacatgtct ttggcttcta acttgttgaa gtacttgttc gttcacagaa    1380
actgcagaat ccatggtcc tctatcgtta tttctagaac tccagatcca catagaaggc    1440
catgttatat tccaccatct ggttctcaag aggattcttt taaagatggt tacaccggta    1500
tcaacgtcga gtttaatgtt tctcatcaag cctccatggt tgctattgct ggtactgctt    1560
ttactccaaa ttctggtggt gattctaagt tgaaaccaga agttggtatc gatattacct    1620
gcgtcaacga aagacaaggt agaaatggtg aagaaaggtc cttggaatct ttgagacagt    1680
acatcgatat cttctccgaa gttttctcta ctgctgaaat ggccaacatt gaagattgg    1740 atggtgtctc ttcttcctca ttgtctgctg atagattggt tgattatggc tacaggttgt    1800
tctatactta ctgggctttg aaagaagcct acattaagat gactggtgaa gccttgttgg    1860
ctccatggtt gagagaattg gaattctcta atgttgttgc tccagctgct gttgctgaat    1920
ctggtgattc tgctggtgat tttggtgaac catatactgg tgttagaacc accttgtaca    1980
agaacttggt tgaagatgtt agaattgaag ttgctgcttt gggtggtgat tacttgtttg    2040
ctactgctgc tagaggtggt ggtattggtg cttcttctag accaggtggt ggtccagatg    2100
gttctggtat tagatctcaa gatccttgga ggccattcaa gaagttggat attgaaaggg    2160
atattcaacc atgtgctact ggtgtatgta actgcttgtc ttaaagacat aaaactgaaa    2220
caacaccaat taataataga ctttacagaa gacgggagac actagcacac aactttacca    2280
ggcaaggtat ttgacgctag catgtgtcca attcagtgtc atttatgatt ttttgtagta    2340
ggatataaat atatacagcg ctccaaatag tgcggttgcc ccaaaaacac cacggaacct    2400
catctgttct cgtactttgt tgtgacaaag tagctcactg ccttattatc acattttcat    2460
tatgcaacgc ttcggaaaat acgatgttga aaatgcctct agagatgaaa acaatcgta    2520 aagggtcct gcgtaattga aacatttgat cagtatgcag tggcacagaa acaaccagga    2580
atactatagt cataggcaat acaaggtata tattggctat gcagacccct ccagaaagta    2640
ccgacgtcaa gttagataca cttaacgaac ctagtgcaca tttaattgag aaaaatgtgg    2700
```

-continued

```
ctcttcctaa ggacatattc cgttcgtact tgagttattg gatctatgaa atcgctcgct     2760
atacaccagt catgattttg tccttaaata acatactcat cactaaacat tcttaacaat     2820
cagaaaatgc aaccgataaa acattataaa tcttcgcggt tatctggcat tgttattaac     2880
caaaaaaatg ccggcctatt acaagctact gttcaataaa tattgttgta atgaagacgg     2940
tccaactgta caaatacagc aaactgtcat atataaggtg tcttatgtga cagcacttgc     3000
gttattgtca gccggagtat gtctttgtcg cattctgggc ttttttacttt ctgctcagaa     3060 ggaagtacga acaagaaaaa aaaatcacca atgcttccct tttcagtatt agtttcatat     3120
ttgtttacgt tcaaactcgt cgtttgcgcg ataacctcta aaaaagtcag ttacgtaact     3180
atatcaatca gagaatgcaa aaagcactat cataaaaatg tctctagggg atgtgagaca     3240
tgtcaattat aagaagtgat ggtgtcatag tatatatatc ataaatgatt atcaaagttt     3300
caatcctttg tattttctag tttagcgcca acttttgaca aaacctaaac tttagataat     3360
catcattctt acaatttta tctggatggc aataatctcc tatataaagc ccagataaac     3420
tgtaaaaaga atccatcact atttgaaaaa aagtcatctg gcacgtttaa ttatcagagc     3480
agaaatgatg aagggtgtta gcgccgtcca ttgatgcgcc tggtagtcat gatttacgta     3540 taactaaacac atcatgagga cggc                                           3564
```

```
<210> SEQ ID NO 9
<211> LENGTH: 10584
<212> TYPE: DNA
<213> ORGANISM: Artificial Sequence
<220> FEATURE:
<223> OTHER INFORMATION: Cassette with Dictyostelium discoideum DiPKS
      (G1516D; G1518A) coding sequence, regulatory sequences and
      integration sequences
<220> FEATURE:
<221> NAME/KEY: LV3
<222> LOCATION: (1)..(40)
<220> FEATURE:
<221> NAME/KEY: S. cerevisiae GAL1 promoter
<222> LOCATION: (41)..(482)
<220> FEATURE:
<221> NAME/KEY: L1
<222> LOCATION: (483)..(522)
<220> FEATURE:
<221> NAME/KEY: DiPKS
<222> LOCATION: (523)..(9966)
<220> FEATURE:
<221> NAME/KEY: C-methyltransferase domain
<222> LOCATION: (5050)..(5412)
<220> FEATURE:
<221> NAME/KEY: Motif 1
<222> LOCATION: (5050)..(5076)
<220> FEATURE:
<221> NAME/KEY: G1516D
<222> LOCATION: (5068)..(5070)
<220> FEATURE:
<221> NAME/KEY: G1518A
<222> LOCATION: (5074)..(5076)
<220> FEATURE:
<221> NAME/KEY: Motif 2
<222> LOCATION: (5309)..(5331)
<220> FEATURE:
<221> NAME/KEY: Motif 3
<222> LOCATION: (5389)..(5421)
<220> FEATURE:
<221> NAME/KEY: L2
<222> LOCATION: (9967)..(10006)
<220> FEATURE:
<221> NAME/KEY: PRM9t
<222> LOCATION: (10007)..(10544)
<220> FEATURE:
<221> NAME/KEY: LV5
<222> LOCATION: (10545)..(10584)
```

<400> SEQUENCE: 9

```
aggaatactc tgaataaaac aacttatata ataaaaatgc cggattagaa gccgccgagc      60
gggtgacagc cctccgaagg aagactctcc tccgtgcgtc ctcgtcttca ccggtcgcgt     120
tcctgaaacg cagatgtgcc tcgcgccgca ctgctccgaa caataaagat tctacaatac     180
tagcttttat ggttatgaag aggaaaaatt ggcagtaacc tggccccaca aaccttcaaa     240
tgaacgaatc aaattaacaa ccataggatg ataatgcgat tagttttta gccttatttc      300
tggggtaatt aatcagcgaa gcgatgattt tgatctatt aacagatata taaatgcaaa      360
aactgcataa ccactttaac taatactttc aacattttcg gtttgtatta cttcttattc     420
aaatgtaata aaagtatcaa caaaaaattg ttaatatacc tctatacttt aacgtcaagg     480
agctagaaaa tttattataa aaggaagaga ataattaaaa caatgaacaa gaactccaaa     540
atccagtccc caaactcttc tgatgttgct gttattggtg ttggttttag attcccaggt     600
aactctaatg acccagaatc tttgtggaac aacttgttgg atggtttcga tgctattacc     660
caagtcccaa agaaagatg gctacttct tttagagaga tgggtttgat caagaacaag       720
ttcggtggtt tcttgaagga ttctgaatgg aagaatttcg acccttgtt ctttggtatc      780
ggtccaaaag aagctccatt cattgatcca caacaaggt tgttgttgtc catcgtttgg      840
gaatctttgg aagatgctta catcagacca gatgaattga gaggttctaa cactggtgtt     900
ttcatcggtg tttctaacaa cgattacacc aagttgggtt ccaagacaa ctactctatt      960
tctccataca ctatgaccgg ctctaactct tcattgaact ccaacagaat ttcctactgc    1020
ttcgattta gaggtccatc cattactgtt gataccgctt gttcttcttc cttggtttct     1080
gttaatttgg gtgtccaatc catccaaatg ggtgaatgta agattgctat ttgcggtggt    1140
gttaacgctt tgtttgatcc atctacatct gttgccttt ccaagttggg tgttttgtct     1200
gaaaatggca gatgcaactc ttttagtgat caagcctctg gttacgttag atctgaaggt    1260
gctggtgttg ttgttttgaa gtctttggaa caagctaagt tggatggtga tagaatctac    1320
ggtgttatca agggtgtttc ctctaatgaa gatggtgctt ctaatggtga caagaactct    1380
ttgactactc catcttgtga agcccaatcc attaacattt ctaaggctat ggaaaaggcc    1440
tccttgtctc catctgatat ctattacatt gaagcccatg gtactggtac tccagttggt    1500
gatccaattg aagttaaggc cttgtccaag atcttctcca actctaacaa caaccagttg    1560
aacaacttct ctaccgatgg taatgataac gatgatgatg atgacgataa cacctctcca    1620
gaaccattat tgattggctc attcaagtcc aacatcggtc atttggaatc tgctgctggt    1680
attgcttctt tgattaagtg ttgcttgatg ttgaagaaca ggatgttggt tccatccatt    1740
aactgctcta atttgaaccc atccattcca ttcgatcagt acaacatctc cgttatcaga    1800
gaaatcagac aattcccaac cgataagttg gttaacatcg gtatcaattc tttcggtttc    1860
ggtggttcta actgccattt gattattcaa gagtacaaca caacttcaa gaacaactct    1920
accatctgca ataacaacaa caacaacaat aacaacatcg actacttgat cccaatctcc    1980
tctaagacta agaagtcctt ggataagtac ttgattttga tcaagaccaa ctccaactac    2040
cacaaggata tttctttcga tgacttcgtc aagttccaaa tcaagtctaa gcagtacaac    2100
ttgtccaaca gaatgactac cattgctaac gattggaact ccttcattaa gggttctaac    2160
gaattccaca acttgatcga atctaaggat ggtgaaggtg ttcttcatc ttctaacaga     2220
ggtattgatt ccgccaatca aatcaacact actactacct ctaccatcaa cgatatcgaa    2280
cctttgttgg ttttcgtttt ctgtggtcaa ggtccacaat ggaatggtat gattaagacc    2340
```

```
ttgtacaact ccgagaacgt tttcaagaac accgttgatc atgttgacag catcttgtac    2400
aagtacttcg gttactccat tttgaacgtc ttgtctaaga tcgatgataa cgacgattcc    2460
atcaaccatc caatagttgc tcaaccatct ttgttcttgt tgcaaattgg tttggtcgag    2520
ttgtttaagt actggggtat ctacccatct atctctgttg gtcattcttt cggtgaagtc    2580
tcttcttatt acttgtccgg tatcatctct ttggaaaccg cttgtaaaat cgtctacgtc    2640
agatcctcta atcagaacaa aactatgggt tccggtaaga tgttggttgt ttctatgggt    2700
tttaagcaat ggaacgatca attctctgct gaatggtccg atattgaaat tgcttgttac    2760
aacgctccag attccatagt tgttactggt aacgaagaaa gattgaaaga attgtccatc    2820
aagttgtccg acgaatccaa tcaaattttc aacaccttct tgaggtcccc atgttctttt    2880
cattcttccc atcaagaagt catcaagggt tctatgttcg aagagttgtc taacttgcaa    2940
tctactggtg aaaccgaaat cccttttgttc tctactgtta ctggtagaca agttttgtct    3000
ggtcatgtta ctgctcaaca catctacgat aatgttagag aaccagtctt gttccaaaag    3060
acgattgaat ccattaccct ctacatcaag tctcactacc catccaatca aaaggttatc    3120
tacgttgaaa ttgctccaca cccaaccttg ttttcattga tcaaaaagtc catcccatcc    3180
tccaacaaga attcctcttc tgttttgtgt ccattgaaca gaaaagaaaa ctccaacaac    3240
tcctacaaga gttcgtttc tcagttgtac ttcaacggtg ttaacgttga cttcaacttc    3300
cagttgaact ccatttgcga taacgttaac aacgatcacc atttgaacaa cgtcaagcaa    3360
aactccttca aagagactac caattccttg ccaagatacc aatgggaaca agatgaatat    3420
tggtccgaac cattgatctc cagaaagaat agattggaag gtccaactac ttccttgttg    3480
ggtcatagaa ttatctacag cttcccagtt ttccaatccg ttttggactt gcaatctgac    3540
aactacaaat acttgttgga ccacttggtt aacggtaagc cagttttttcc aggtgctggt    3600 tatttggata tcatcatcga attcttcgac taccaaaagc agcagttgaa ttcctctgat    3660
tcctctaact cctacatcat caacgttgac aagatccaat tcttgaaccc aattcacttg    3720
accgaaaaca gttgcaaac cttgcaatct tctttcgaac ctatcgttac taagaagtct    3780
gccttctctg ttaacttctt catcaaggat accgtcgagg atcaatctaa ggttaagtct    3840
atgtctgacg aaacttggac taacacttgt aaggctacca tttccttgga caacaacag    3900 ccatctccat cttctacttt gactttgtct aagaagcaag acttgcagat cttgagaaac    3960
agatgcgata ttagcaagct agacaagttt gagttgtacg acaagatctc taagaatttg    4020
ggcttgcagt acaactcctt gtttcaagtt gttgatacca tcgaaactgg taaggattgc    4080
tcttttgcta ctttgtcttt gccagaagat actttgttca ccaccatttt gaacccatgc    4140
ttgttggata actgtttcca tggtttgttg accttgatca cgaaaagggg ttctttcgtt    4200
gtcgagtcca tttcttctgt ttctatctac ttggagaaca tcggttcctt caatcaaact    4260
tctgttggta acgtccagtt ctacttgtac accactattt ctaaagccac ctcctttagt    4320
tctgaaggta cttgtaagtt gttcaccaag gatggttcct tgatttttgtc tatcggtaag    4380 ttcatcatca gtccaccaa tccaaagtct actaagacca acgaaactat cgaatctcca    4440
ttggacgaaa ccttctctat tgaatggcaa tctaaggatt ctccaattcc aaccccacaa    4500
caaatccaac aacaatctcc attgaactct aacccatcct tcattagatc taccatcttg    4560
aaggacatcc agttcgaaca atactgctcc tccattatcc acaaagaatt gatcaaccac    4620
gaaaagtaca agaaccagca atccttcgat atcaactcct tggaaaacca cttgaacgat    4680
```

```
gaccaattga tggaatcctt gtccatctcc aaagaatact tgagattctt caccaggatc    4740
atctccatca ttaagcaata cccaaagatc ttgaacgaaa aagagctaaa agaattgaaa    4800
gaaatcatcg aattgaagta cccatccgaa gttcagttgt tggaattcga agttatcgag    4860
aaggtgtcca tgattatccc aaagttgttg ttcgaaaacg acaagcaatc ttccatgacc    4920
ttgttccaag ataacttgtt gaccaggttc tactccaatt ctaactctac cagattctac    4980
ttggaaaggg tttccgaaat ggtcttggaa tctattagac caatcgtcag agaaaagagg    5040
gtgttcagaa ttttggaaat tggtgctgat acagcctctt tgtctaatgt tgttttgact    5100
aagttgaaca cctacttgtc caccttgaat tctaatggtg gttctggtta caacatcatc    5160
attgagtaca ccttcaccga tatttccgcc aacttcatta ttggtgaaat ccaagaaacc    5220
atgtgcaact tgtacccaaa cgttactttc aagttctccg tcttggactt ggagaaagag    5280
attattaact cctccgattt cttgatgggt gattacgata tagttttgat ggcctacgtt    5340
atccatgccg tttctaacat taagttctcc atcgaacagt tgtacaagtt gttgtctcca    5400
agaggttggt tgttgtgtat tgaacctaag tccaacgttg tgttctccga tttggttttc    5460
ggttgtttta atcagtggtg gaactactac gatgatatta gaactaccca ctgctccttg    5520
tctgaatctc aatggaatca gttgttgttg aaccagtcct tgaacaacga atcctcttct    5580
tcttctaact gttacggtgg tttctccaac gtttctttta ttggtggtga aaaggatgtc    5640
gactcccatt ctttcatatt gcactgccaa aaagaatcca tctcccaaat gaagttagcc    5700
accactatta caacggtttt gtcatctggt tccatcgtta tcgttttgaa ctctcaacaa    5760
ttgaccaaca tgaagtccta cccaaaggtt attgagtata ttcaagaggc tacctctttg    5820
tgcaagacca ttgaaattat cgattccaag gacgtcttga actctaccaa ttcagttttg    5880
gaaaagatcc aaaagtcctt gttggtgttc tgtttgttgg gttatgactt gttggagaac    5940
aactaccaag aacagtcttt cgaatacgtt aagttgttga acttgatctc tactaccgcc    6000
tcttcatcta tgataagaa accaccaaag gtcttgttga tcaccaagca atctgaaaga    6060
atctccaggt ctttctactc cagatccttg attggtattt ccagaacctc tatgaacgag    6120
tacccaaatt tgtccattac ctctatcgat ttggatacca acgactactc attgcagtct    6180
ttgttgaagc caatcttcag caactctaag ttttccgaca acgagttcat cttcaaaaag    6240
ggcttgatgt tcgtgtccag gatctttaag aacaagcagt tgctagaatc ctccaacgct    6300
tttgaaactg actcttctaa cttgtactgt aaggcctctt ctgacttgtc ttacaagtac    6360
gctattaagc agtctatgtt gaccgaaaat cagatcgaaa tcaaggttga atgcgtcggt    6420
attaacttca aggacaacct attctacaag ggcttgttgc cacaagaaat tttcagaatg    6480
ggtgacatct acaatccacc atatggtttg aatgctctg tgttattac cagaattggt    6540 tctaacgtca ccgaatactc agttggtcaa aatgttttg gtttcgccag acattctttg    6600
ggttctcatg ttgttaccaa caaggatttg gttatcttga agccagatac catctcattt    6660
tctgaagctg cttctatccc agttgtttac tgtactgctt ggtactcctt gttcaacatt    6720
ggtcagttgt ctaacgaaga atccatccta attcattctg ctactggtgg tgtaggtttg    6780
gcttctttga atttgttgaa aatgaagaat cagcaacagc aaccattgac caatgtttat    6840
gctactgttg gctctaacga aagaagaag ttcttgatcg ataacttcaa caacttgttc    6900
aaagaggacg gcgaaaacat tttctctacc agagacaaag aatactccaa ccagttggaa    6960
tccaagatcg atgttatttt gaacaccttg tccggtgaat tcgtcgaatc taatttcaag    7020
tccttgagat ccttcggtag attgattgat ttgtctgcta ctcacgttta cgccaatcaa    7080
```

```
caaattggtc taggtaactt caagttcgac cacttgtatt ctgctgttga cttggaaaga   7140
ttgatcgacg aaaaacctaa gttgttgcag tccatcttgc aaagaattac caactctatc   7200
gtcaacggtt ccttggaaaa aattccaatt accatcttcc catccaccga aactaaggat   7260
gctatcgaat tattgtccaa gagatcccat atcggtaaag ttgttgtaga ttgcaccgat   7320
atctctaagt gtaatcctgt tggtgatgtg atcaccaact tctctatgag attgccaaag   7380
ccaaactacc agttgaattt gaactccacc ttgttgatta ctggtcagtc tggtttgtct   7440
atccctttgt tgaattggtt gttgtctaag tctggtggta acgttaagaa cgttgtcatc   7500
atttctaagt ccaccatgaa gtggaagttg cagactatga tttcccattt cgtttccggt   7560
ttcggtatcc attttaacta cgttcaagtc gacatctcca actacgatgc tttgtctgaa   7620
gctattaagc aattgccatc tgatttgcca ccaatcacct ctgtttttca tttggctgct   7680
atctacaacg atgttccaat ggatcaagtt accatgtcta ccgttgaatc tgttcataac   7740
cctaaagttt ggggtgccgt taacttgcat agaatctctg tttctttttgg ttggaagttg   7800 aaccacttcg tcttgttctc ttctattact gctattaccg gttacccaga ccaatctatc   7860
tacaattctg ccaactctat tttggacgct tgtccaact ttagaaggtt tatgggtttg   7920
ccatccttct ccattaactt gggtccaatg aaggatgaag gtaaggtttc taccaacaag   7980
agcatcaaga agctattcaa gtctagaggt ttgccaagcc tatccttgaa caagttattt   8040
ggtttgttgg aggtcgtcat caacaaccca tctaatcatg ttatcccatc ccaattgatt   8100
tgctccccaa tcgatttcaa gacctacatc gaatctttct caactatgag gccaaagttg   8160
ttacacttgc aacctaccat ttccaagcag caatcttcta tcattaacga ttctaccaag   8220
gcttcctcca catttcatt gcaagataag atcacctcca aggtgtctga tttgttgtcc   8280
attccaatct ccaagatcaa cttcgatcat ccattgaaac actacggctt ggattctttg   8340
ttgaccgttc aattcaaatc ctggatcgac aaagaattcg aaaagaactt gttcacccat   8400
atccaattgg ccaccatctc tattaactca ttcttggaaa aggtgaacgg cttgtctaca   8460
aacaataaca caacaacaa ttccaacgtc aagtcctctc catccattgt caaagaagaa   8520
atcgttacct tggacaagga tcaacaacca ttgctattga agaacaccca gcacattatc   8580
atctccccag atattagaat caacaagcca agagggaat ccttgattag aaccccaatc   8640
ttgaacaaat tcaaccagat caccgaatcc attatcactc catctacacc atctttgtcc   8700
caatccgatg ttttgaaaac tccaccaatc aagtctttga caacactaa gaactccagc   8760 ttgattaaca ccccaccaat tcaatctgtc caacaacatc aaaagcaaca acaaaaggtc   8820
caagtcatcc aacaacagca acaaccatta tccagattgt cctacaagag caacaacaac   8880
tctttcgttt tgggtatcgg tatttctgtt ccaggtgaac ctatttccca acaatccttg   8940
aaagactcca tctccaatga cttttctgat aaggctgaaa ctaacgagaa ggtcaagaga   9000
atctttgagc aatctcaaat caagaccaga cacttggtta gagattacac taagccagag   9060
aactccatca gttcagaca tttggaaacc attaccgatg tgaacaacca gttcaagaaa   9120
gttgttccag atttggctca acaagcctgt tgagagctt tgaaagattg gggtggtgat   9180
aagggtgata ttacccatat agtttctgtt acctccaccg gtattatcat cccagatgtt   9240
aatttcaagt tgatcgactt gttgggcttg aacaaggatg ttgaaagagt gtctttgaac   9300
ctaatgggtt gtttggctgg tttgagttct ttgagaactg ctgcttcttt ggctaaggct   9360
tctccaagaa atagaatttt ggttgtctgt accgaagtct gctccttgca ttttttctaat   9420
```

```
actgatggtg gtgatcaaat ggtcgcctct tctattttg ctgatggttc tgctgcttac    9480
attattggtt gtaacccaag aattgaagaa accccattat acgaagtcat gtgctccatt    9540
aacagatctt tcccaaatac cgaaaacgcc atggtttggg atttggaaaa agaaggttgg    9600 aacttggggtt tggatgcttc tattccaatt gtcattggtt ctggtattga agccttcgtt    9660
gatactttgt tggataaggc taagttgcaa acttccactg ctatttctgc taaggattgc    9720
gaattcttga ttcatactgg tggcaagtcc atcttgatga acatcgaaaa ttccttgggt    9780
atcgacccaa agcaaactaa gaatacttgg gatgtttacc atgcctacgg caatatgtca    9840
tctgcctctg ttattttcgt tatggatcat gccagaaagt ccaagtcttt gccaacttac    9900
tcaatttctt tggcttttgg tccaggtttg gcttttgaag ttgtttctt gaagaacgtc    9960 gtctaaagac ataaaactga acaacacca attaataata gactttacag aagacgggag    10020
acactagcac acaactttac caggcaaggt atttgacgct agcatgtgtc caattcagtg    10080
tcatttatga tttttgtag taggatataa atatatacag cgctccaaat agtgcggttg    10140 cccccaaaaac accacggaac ctcatctgtt ctcgtacttt gttgtgacaa agtagctcac    10200
tgccttatta tcacattttc attatgcaac gcttcggaaa atacgatgtt gaaaatgcct    10260
ctagagatga aaaacaatcg taaaagggtc ctgcgtaatt gaaacatttg atcagtatgc    10320
agtggcacag aaacaaccag gaatactata gtcataggca atacaaggta tatattggct    10380
atgcagaccc ctccagaaag taccgacgtc aagttagata cacttaacga acctagtgca    10440
catttaattg agaaaaatgt ggctcttcct aaggacatat tccgttcgta cttgagttat    10500
tggatctatg aaatcgctcg ctatacacca gtcatgattt tgtccctctt tatattacat    10560
caaaataaga aataattat aaca                                             10584
```

<210> SEQ ID NO 10
<211> LENGTH: 10584
<212> TYPE: DNA
<213> ORGANISM: Artificial Sequence
<220> FEATURE:
<223> OTHER INFORMATION: Cassette with Dictyostelium discoideum DiPKS
      (G1516R) coding sequence, regulatory sequences and integration
      sequences
<220> FEATURE:
<221> NAME/KEY: LV3
<222> LOCATION: (1)..(40)
<220> FEATURE:
<221> NAME/KEY: S. cerevisiae GAL1 promoter
<222> LOCATION: (41)..(482)
<220> FEATURE:
<221> NAME/KEY: L1
<222> LOCATION: (483)..(522)
<220> FEATURE:
<221> NAME/KEY: DiPKS
<222> LOCATION: (523)..(9966)
<220> FEATURE:
<221> NAME/KEY: C-methyltransferase domain
<222> LOCATION: (5050)..(5412)
<220> FEATURE:
<221> NAME/KEY: G1516R
<222> LOCATION: (5069)..(5070)
<220> FEATURE:
<221> NAME/KEY: Motif 2
<222> LOCATION: (5309)..(5331)
<220> FEATURE:
<221> NAME/KEY: Motif 3
<222> LOCATION: (5389)..(5421)
<220> FEATURE:
<221> NAME/KEY: Type III PKS domain
<222> LOCATION: (8881)..(9966)
<220> FEATURE:
<221> NAME/KEY: L2
<222> LOCATION: (9967)..(10006)

```
<220> FEATURE:
<221> NAME/KEY: PRM9t
<222> LOCATION: (10007)..(10544)
<220> FEATURE:
<221> NAME/KEY: LV5
<222> LOCATION: (10545)..(10584)

<400> SEQUENCE: 10
aggaatactc tgaataaaac aacttatata ataaaaatgc cggattagaa gccgccgagc      60
gggtgacagc cctccgaagg aagactctcc tccgtgcgtc ctcgtcttca ccggtcgcgt     120
tcctgaaacg cagatgtgcc tcgcgccgca ctgctccgaa caataaagat tctacaatac     180
tagctttat ggttatgaag aggaaaaatt ggcagtaacc tggccccaca aaccttcaaa     240
tgaacgaatc aaattaacaa ccataggatg ataatgcgat tagttttta gccttatttc     300
tggggtaatt aatcagcgaa gcgatgattt ttgatctatt aacagatata taaatgcaaa     360
aactgcataa ccactttaac taatactttc aacattttcg gtttgtatta cttcttattc     420
aaatgtaata aaagtatcaa caaaaaattg ttaatatacc tctatacttt aacgtcaagg     480
agctagaaaa tttattataa aaggaagaga ataattaaaa caatgaacaa gaactccaaa     540
atccagtccc caaactcttc tgatgttgct gttattggtg ttggttttag attcccaggt     600
aactctaatg acccagaatc tttgtggaac aacttgttgg atggtttcga tgctattacc     660
caagtcccaa agaaagatg ggctacttct tttagagaga tgggtttgat caagaacaag     720
ttcggtggtt tcttgaagga ttctgaatgg aagaatttcg accctttgtt ctttggtatc     780
ggtccaaaag aagctccatt cattgatcca caacaaggt tgttgttgtc catcgtttgg     840
gaatctttgg aagatgctta catcagacca gatgaattga gaggttctaa cactggtgtt     900
ttcatcggtg tttctaacaa cgattacacc aagttgggtt ccaagacaa ctactctatt     960
tctccataca ctatgaccgg ctctaactct tcattgaact ccaacagaat tcctactgc    1020
ttcgattta gaggtccatc cattactgtt gataccgctt gttcttcttc cttggtttct    1080
gttaatttgg gtgtccaatc catccaaatg ggtgaatgta agattgctat ttgcggtggt    1140
gttaacgctt tgtttgatcc atctacatct gttgcctttt ccaagttggg tgttttgtct    1200
gaaaatggca gatgcaactc ttttagtgat caagcctctg gttacgttag atctgaaggt    1260
gctggtgttg ttgttttgaa gtctttggaa caagctaagt tggatggtga tagaatctac    1320
ggtgttatca agggtgtttc ctctaatgaa atggtgctt ctaatggtga caagaactct    1380
ttgactactc catcttgtga agcccaatcc attaacattt ctaaggctat ggaaaaggcc    1440
tccttgtctc catctgatat ctattacatt gaagcccatg gtactggtac tccagttggt    1500
gatccaattg aagttaaggc cttgtccaag atcttctcca actctaacaa caaccagttg    1560
aacaacttct ctaccgatgg taatgataac gatgatgatg atgacgataa cacctctcca    1620
gaaccattat tgattggctc attcaagtcc aacatcggtc atttggaatc tgctgctggt    1680
attgcttctt tgattaagtg ttgcttgatg ttgaagaaca ggatgttggt tccatccatt    1740
aactgctcta atttgaaccc atccattcca ttcgatcagt acaacatctc cgttatcaga    1800
gaaatcagac aattcccaac cgataagttg gttaacatcg gtatcaattc tttcggtttc    1860
ggtggttcta actgccattt gattattcaa gagtacaaca caaacttcaa gaacaactct    1920
accatctgca ataacaacaa caacaacaat aacaacatcg actacttgat cccaatctcc    1980
tctaagacta gaagtccctt ggataagtac ttgattttga tcaagaccaa ctccaactac    2040
cacaaggata tttctttcga tgacttcgtc aagttccaaa tcagtctaa gcagtacaac    2100
```

```
ttgtccaaca gaatgactac cattgctaac gattggaact ccttcattaa gggttctaac    2160
gaattccaca acttgatcga atctaaggat ggtgaaggtg gttcttcatc ttctaacaga    2220
ggtattgatt ccgccaatca aatcaacact actactacct ctaccatcaa cgatatcgaa    2280
cctttgttgg ttttcgtttt ctgtggtcaa ggtccacaat ggaatggtat gattaagacc    2340
ttgtacaact ccgagaacgt tttcaagaac accgttgatc atgttgacag catcttgtac    2400
aagtacttcg gttactccat tttgaacgtc ttgtctaaga tcgatgataa cgacgattcc    2460
atcaaccatc caatagttgc tcaaccatct ttgttcttgt tgcaaattgg tttggtcgag    2520
ttgtttaagt actggggtat ctacccatct atctctgttg gtcattcttt cggtgaagtc    2580
tcttcttatt acttgtccgg tatcatctct ttggaaaccg cttgtaaaat cgtctacgtc    2640
agatcctcta atcagaacaa aactatgggt tccggtaaga tgttggttgt ttctatgggt    2700
tttaagcaat ggaacgatca attctctgct gaatggtccg atattgaaat tgcttgttac    2760
aacgctccag attccatagt tgttactggt aacgaagaaa gattgaaaga attgtccatc    2820
aagttgtccg acgaatccaa tcaaattttc aacaccttct tgaggtcccc atgttctttt    2880
cattcttccc atcaagaagt catcaagggt tctatgttcg aagagttgtc taacttgcaa    2940
tctactggtg aaaccgaaat ccctttgttc tctactgtta ctggtagaca gttttgtct    3000
ggtcatgtta ctgctcaaca catctacgat aatgttagag aaccagtctt gttccaaaag    3060
acgattgaat ccattacctc ctacatcaag tctcactacc catccaatca aaaggttatc    3120
tacgttgaaa ttgctccaca cccaaccttg ttttcattga tcaaaaagtc catcccatcc    3180
tccaacaaga attcctcttc tgttttgtgt ccattgaaca gaaagaaaa ctccaacaac    3240
tcctacaaga agttcgtttc tcagttgtac ttcacggtg ttaacgttga cttcaacttc    3300
cagttgaact ccatttgcga taacgttaac aacgatcacc atttgaacaa cgtcaagcaa    3360
aactccttca aagagactac caattccttg ccaagatacc aatgggaaca agatgaatat    3420
tggtccgaac cattgatctc cagaaagaat agattggaag gtccaactac ttccttgttg    3480
ggtcatagaa ttatctacag cttcccagtt ttccaatccg ttttggactt gcaatctgac    3540
aactacaaat acttgttgga ccacttggtt aacggtaagc cagttttttcc aggtgctggt    3600
tatttggata tcatcatcga attcttcgac taccaaaagc agcagttgaa ttcctctgat    3660
tcctctaact cctacatcat caacgttgac aagatccaat tcttgaaccc aattcacttg    3720
accgaaaaca gttgcaaac cttgcaatct tctttcgaac ctatcgttac taagaagtct    3780
gccttctctg ttaacttctt catcaaggat accgtcgagg atcaatctaa ggttaagtct    3840
atgtctgacg aaacttggac taacacttgt aaggctacca tttccttgga caacaacag    3900
ccatctccat cttctacttt gactttgtct aagaagcaag acttgcagat cttgagaaac    3960
agatgcgata ttagcaagct agacaagttt gagttgtacg acaagatctc taagaatttg    4020
ggcttgcagt acaactcctt gtttcaagtt gttgatacca tcgaaactgg taaggattgc    4080
tcttttgcta ctttgtcttt gccagaagat actttgttca ccaccatttt gaacccatgc    4140
ttgttggata actgtttcca tggtttgttg accttgatca cgaaaaggg ttctttcgtt    4200
gtcgagtcca tttcttctgt ttctatctac ttggagaaca tcggttcctt caatcaaact    4260
tctgttggta acgtccagtt ctacttgtac accactattt ctaaagccac ctcctttagt    4320
tctgaaggta cttgtaagtt gttcaccaag gatggttcct tgattttgtc tatcggtaag    4380
ttcatcatca gtccaccaa tccaaagtct actaagacca cgaaactat cgaatctcca    4440
ttggacgaaa ccttctctat tgaatggcaa tctaaggatt ctccaattcc aaccccacaa    4500
```

```
caaatccaac aacaatctcc attgaactct aacccatcct tcattagatc taccatcttg   4560
aaggacatcc agttcgaaca atactgctcc tccattatcc acaaagaatt gatcaaccac   4620
gaaaagtaca agaaccagca atccttcgat atcaactcct tggaaaacca cttgaacgat   4680
gaccaattga tggaatcctt gtccatctcc aaagaatact tgagattctt caccaggatc   4740
atctccatca ttaagcaata cccaaagatc ttgaacgaaa agagctaaa agaattgaaa   4800 gaaatcatcg aattgaagta cccatccgaa gttcagttgt tggaattcga agttatcgag   4860
aaggtgtcca tgattatccc aaagttgttg ttcgaaaacg acaagcaatc ttccatgacc   4920
ttgttccaag ataacttgtt gaccaggttc tactccaatt ctaactctac cagattctac   4980
ttggaaaggg tttccgaaat ggtcttggaa tctattagac caatcgtcag agaaaagagg   5040
gtgttcagaa tttagagat cggtgctcgt acaggctctt tgtctaatgt tgttttgact   5100
aagttgaaca cctacttgtc caccttgaat tctaatggtg gttctggtta caacatcatc   5160
attgagtaca ccttcaccga tatttccgcc aacttcatta ttggtgaaat ccaagaaacc   5220
atgtgcaact tgtacccaaa cgttactttc aagttctccg tcttggactt ggagaaagag   5280
attattaact cctccgattt cttgatgggt gattacgata tagttttgat ggcctacgtt   5340
atccatgccg tttctaacat taagttctcc atcgaacagt tgtacaagtt gttgtctcca   5400
agaggttggt tgttgtgtat tgaacctaag tccaacgttg tgttctccga tttggttttc   5460
ggttgtttta atcagtggtg gaactactac gatgatatta gaactaccca ctgctccttg   5520
tctgaatctc aatggaatca gttgttgttg aaccagtcct tgaacaacga atcctcttct   5580
tcttctaact gttacggtgg tttctccaac gtttcttta ttggtggtga aaaggatgtc   5640
gactcccatt ctttcatatt gcactgccaa aaagaatcca tctcccaaat gaagttagcc   5700
accactatta acaacggttt gtcatctggt tccatcgtta tcgttttgaa ctctcaacaa   5760
ttgaccaaca tgaagtccta cccaaaggtt attgagtata ttcaagaggc tacctctttg   5820
tgcaagacca ttgaaattat cgattccaag gacgtcttga actctaccaa ttcagttttg   5880
gaaaagatcc aaaagtcctt gttggtgttc tgtttgttgg ttatgactt gttggagaac   5940 aactaccaag aacagtcttt cgaatacgtt aagttgttga acttgatctc tactaccgcc   6000
tcttcatcta tgataagaa accaccaaag gtcttgttga tcaccaagca atctgaaaga   6060
atctccaggt ctttctactc cagatccttg attggtattt ccagaacctc tatgaacgag   6120
tacccaaatt tgtccattac ctctatcgat ttggatacca acgactactc attgcagtct   6180 tgttgaagc caatcttcag caactctaag ttttccgaca acgagttcat cttcaaaaag   6240
ggcttgatgt tcgtgtccag gatctttaag aacaagcagt tgctagaatc ctccaacgct   6300
tttgaaactg actcttctaa cttgtactgt aaggcctctt ctgacttgtc ttacaagtac   6360
gctattaagc agtctatgtt gaccgaaaat cagatcgaaa tcaaggttga atgcgtcggt   6420
attaacttca aggacaacct attctacaag ggcttgttgc cacaagaaat tttcagaatg   6480
ggtgacatct acaatccacc atatggtttg aatgctctg gtgttattac cagaattggt   6540
tctaacgtca ccgaatactc agttggtcaa aatgttttg gtttcgccag acattctttg   6600
ggttctcatg ttgttaccaa caaggatttg gttatcttga gccagatac catctcattt   6660 tctgaagctg cttctatccc agttgtttac tgtactgctt ggtactcctt gttcaacatt   6720
ggtcagttgt ctaacgaaga atccatccta attcattctg ctactggtgg tgtaggtttg   6780
gcttctttga atttgttgaa aatgaagaat cagcaacagc aaccattgac caatgttat   6840
```

```
gctactgttg gctctaacga gaagaagaag ttcttgatcg ataacttcaa caacttgttc    6900
aaagaggacg gcgaaaacat tttctctacc agagacaaag aatactccaa ccagttggaa    6960
tccaagatcg atgttatttt gaacaccttg tccggtgaat cgtcgaatc taatttcaag     7020
tccttgagat ccttcggtag attgattgat ttgtctgcta ctcacgttta cgccaatcaa    7080
caaattggtc taggtaactt caagttcgac cacttgtatt ctgctgttga cttggaaaga    7140
ttgatcgacg aaaaacctaa gttgttgcag tccatcttgc aaagaattac caactctatc    7200
gtcaacggtt ccttggaaaa aattccaatt accatcttcc catccaccga aactaaggat    7260
gctatcgaat tattgtccaa gagatcccat atcggtaaag ttgttgtaga ttgcaccgat    7320
atctctaagt gtaatcctgt tggtgatgtg atcaccaact tctctatgag attgccaaag    7380
ccaaactacc agttgaattt gaactccacc ttgttgatta ctggtcagtc tggtttgtct    7440
atcccttttgt tgaattggtt gttgtctaag tctggtggta acgttaagaa cgttgtcatc    7500
atttctaagt ccaccatgaa gtggaagttg cagactatga tttcccattt cgtttccggt    7560
ttcggtatcc attttaacta cgttcaagtc gacatctcca actacgatgc tttgtctgaa    7620
gctattaagc aattgccatc tgatttgcca ccaatcacct ctgttttttca tttggctgct    7680
atctacaacg atgttccaat ggatcaagtt accatgtcta ccgttgaatc tgttcataac    7740
cctaaagttt tgggtgccgt taacttgcat agaatctctg tttctttttgg ttggaagttg    7800
aaccacttcg tcttgttctc ttctattact gctattaccg gttacccaga ccaatctatc    7860
tacaattctg ccaactctat tttggacgct ttgtccaact ttagaaggtt tatgggtttg    7920
ccatccttct ccattaactt gggtccaatg aaggatgaag gtaaggtttc taccaacaag    7980
agcatcaaga agctattcaa gtctagaggt ttgccaagcc tatccttgaa caagttattt    8040
ggtttgttgg aggtcgtcat caacaaccca tctaatcatg ttatcccatc ccaattgatt    8100
tgctccccaa tcgatttcaa gacctacatc gaatctttct caactatgag gccaaagttg    8160
ttacacttgc aacctaccat ttccaagcag caatcttcta tcattaacga ttctaccaag    8220
gcttcctcca acatttcatt gcaagataag atcacctcca aggtgtctga tttgttgtcc    8280
attccaatct ccaagatcaa cttcgatcat ccattgaaac actacggctt ggattctttg    8340
ttgaccgttc aattcaaatc ctggatcgac aaagaattcg aaaagaactt gttcacccat    8400
atccaattgg ccaccatctc tattaactca ttcttggaaa aggtgaacgg cttgtctaca    8460
aacaataaca acaacaacaa ttccaacgtc aagtcctctc catccattgt caaagaagaa    8520
atcgttacct tggacaagga tcaacaacca ttgctattga agaacaccca gcacattatc    8580
atctccccag atattagaat caacaagcca agagggaat ccttgattag aaccccaatc     8640
ttgaacaaat tcaaccagat caccgaatcc attatcactc catctacacc atctttgtcc    8700
caatccgatg ttttgaaaac tccaccaatc aagtctttga caacactaa gaactccagc     8760
ttgattaaca ccccaccaat tcaatctgtc caacaacatc aaaagcaaca acaaaaggtc    8820
caagtcatcc aacaacagca acaaccatta tccagattgt cctacaagag caacaacaac    8880
tctttcgttt tgggtatcgg tatttctgtt ccaggtgaac ctatttccca acaatccttg    8940
aaagactcca tctccaatga ctttttctgat aaggctgaaa ctaacgagaa ggtcaagaga    9000
atctttgagc aatctcaaat caagaccaga cacttggtta gagattacac taagccagag    9060
aactccatca gttcagaca tttggaaacc attaccgatg tgaacaacca gttcaagaaa    9120
gttgttccag atttggctca acaagcctgt ttgagagctt tgaaagattg gggtggtgat    9180
aagggtgata ttacccatat agtttctgtt acctccaccg gtattatcat cccagatgtt    9240
```

```
aatttcaagt tgatcgactt gttgggcttg aacaaggatg ttgaaagagt gtctttgaac    9300
ctaatgggtt gtttggctgg tttgagttct ttgagaactg ctgcttcttt ggctaaggct    9360
tctccaagaa atagaatttt ggttgtctgt accgaagtct gctccttgca tttttctaat    9420
actgatggtg gtgatcaaat ggtcgcctct tctattttg ctgatggttc tgctgcttac    9480
attattggtt gtaacccaag aattgaagaa accccattat acgaagtcat gtgctccatt    9540
aacagatctt tcccaaatac cgaaaacgcc atggtttggg atttggaaaa agaaggttgg    9600
aacttgggtt tggatgcttc tattccaatt gtcattggtt ctggtattga agccttcgtt    9660
gatactttgt tggataaggc taagttgcaa acttccactg ctatttctgc taaggattgc    9720
gaattcttga ttcatactgg tggcaagtcc atcttgatga acatcgaaaa ttccttgggt    9780
atcgacccaa agcaaactaa gaatacttgg gatgtttacc atgcctacgg caatatgtca    9840
tctgcctctg ttattttcgt tatggatcat gccagaaagt ccaagtcttt gccaacttac    9900
tcaatttctt tggcttttgg tccaggtttg gcttttgaag gttgtttctt gaagaacgtc    9960
gtctaaagac ataaaactga acaacacca attaataata gactttacag aagacgggag    10020
acactagcac acaactttac caggcaaggt atttgacgct agcatgtgtc caattcagtg    10080
tcatttatga ttttttgtag taggatataa atatatacag cgctccaaat agtgcggttg    10140
ccccaaaaac accacggaac ctcatctgtt ctcgtacttt gttgtgacaa agtagctcac    10200
tgccttatta tcacattttc attatgcaac gcttcggaaa atacgatgtt gaaaatgcct    10260
ctagagatga aaaacaatcg taaaagggtc ctgcgtaatt gaaacatttg atcagtatgc    10320
agtggcacag aaacaaccag gaatactata gtcataggca atacaaggta tatattggct    10380
atgcagaccc ctccagaaag taccgacgtc aagttagata cacttaacga acctagtgca    10440
catttaattg agaaaaatgt ggctcttcct aaggacatat tccgttcgta cttgagttat    10500
tggatctatg aaatcgctcg ctatacacca gtcatgattt tgtccctctt tatattacat    10560
caaaataaga aaataattat aaca                                           10584
```

<210> SEQ ID NO 11
<211> LENGTH: 6034
<212> TYPE: DNA
<213> ORGANISM: Artificial Sequence
<220> FEATURE:
<223> OTHER INFORMATION: Plasmid
<220> FEATURE:
<221> NAME/KEY: LV5
<222> LOCATION: (1)..(40)
<220> FEATURE:
<221> NAME/KEY: pYES2-LEU2
<222> LOCATION: (1915)..(4123)
<220> FEATURE:
<221> NAME/KEY: LEU2 ORF
<222> LOCATION: (1996)..(3090)
<220> FEATURE:
<221> NAME/KEY: LEU2 promoter
<222> LOCATION: (3091)..(3999)
<220> FEATURE:
<221> NAME/KEY: misc_feature
<222> LOCATION: (3759)..(3760)
<223> OTHER INFORMATION: n is a, c, g, or t
<220> FEATURE:
<221> NAME/KEY: LV3
<222> LOCATION: (5995)..(6034)

<400> SEQUENCE: 11

```
cctctttata ttcatcaaa ataagaaaat aattataaca cctgcattaa tgaatcggcc     60
aacgcgcggg gagaggcggt ttgcgtattg ggcgctcttc cgcttcctcg ctcactgact    120
```

```
cgctgcgctc ggtcgttcgg ctgcggcgag cggtatcagc tcactcaaag gcggtaatac    180
ggttatccac agaatcaggg gataacgcag gaaagaacat gtgagcaaaa ggccagcaaa    240
agcccaggaa ccgtaaaaag gccgcgttgc tggcgttttt ccataggctc cgccccctg    300 acgagcatca caaaaatcga cgctcaagtc agaggtggcg aaacccgaca ggactataaa    360
gataccaggc gtttccccct ggaagctccc tcgtgcgctc tcctgttccg accctgccgc    420
ttaccggata cctgtccgcc tttctccctt cgggaagcgt ggcgctttct catagctcac    480
gctgtaggta tctcagttcg gtgtaggtcg ttcgctccaa gctgggctgt gtgcacgaac    540 ccccccgttca gcccgaccgc tgcgccttat ccggtaacta tcgtcttgag tccaacccgg    600
taagacacga cttatcgcca ctggcagcag ccactggtaa caggattagc agagcgaggt    660
atgtaggcgg tgctacagag ttcttgaagt ggtggcctaa ctacggctac actagaagga    720
cagtatttgg tatctgcgct ctgctgaagc cagttacctt cggaaaaaga gttggtagct    780
cttgatccgg caaacaaacc accgctggta gcggtggttt ttttgtttgc aagcagcaga    840
ttacgcgcag aaaaaaagga tctcaagaag atcctttgat cttttctacg ggtctgacg    900 ctcagtggaa cgaaaactca cgttaaggga ttttggtcat gagattatca aaaaggatct    960
tcacctagat ccttttaaat taaaaatgaa gttttaaatc aatctaaagt atatatgagt   1020
aaacttggtc tgacagttac caatgcttaa tcagtgaggc acctatctca gcgatctgtc   1080
tatttcgttc atccatagtt gcctgactcc ccgtcgtgta gataactacg atacgggagc   1140
gcttaccatc tggccccagt gctgcaatga taccgcgaga cccacgctca ccggctccag   1200
atttatcagc aataaaccag ccagccggaa gggccgagcg cagaagtggt cctgcaactt   1260
tatccgcctc cattcagtct attaattgtt gccgggaagc tagagtaagt agttcgccag   1320
ttaatagttt gcgcaacgtt gttggcattg ctacaggcat cgtggtgtca ctctcgtcgt   1380
ttggtatggc ttcattcagc tccggttccc aacgatcaag gcgagttaca tgatccccca   1440
tgttgtgcaa aaaagcggtt agctccttcg gtcctccgat cgttgtcaga agtaagttgg   1500
ccgcagtgtt atcactcatg gttatggcag cactgcataa ttctcttact gtcatgccat   1560
ccgtaagatg cttttctgtg actggtgagt actcaaccaa gtcattctga gaatagtgta   1620
tgcggcgacc gagttgctct tgcccggcgt caatacggga taatagtgta tcacatagca   1680
gaactttaaa agtgctcatc attggaaaac gttcttcggg gcgaaaactc tcaaggatct   1740
taccgctgtt gagatccagt tcgatgtaac ccactcgtgc acccaactga tcttcagcat   1800
cttttacttt caccagcgtt tctgggtgag caaaaacagg aaggcaaaat gccgcaaaaa   1860
agggaataag ggcgacacgg aaatgttgaa tactcatact cttccttttt caatgggtaa   1920
taactgatat aattaaattg aagctctaat ttgtgagttt agtatacatg catttactta   1980
taatacagtt ttttattaag caaggatttt cttaacttct tcggcgacag catcaccgac   2040
ttcggtggta ctgttggaac cacctaaatc accagtctg atacctgcat ccaaaacctt   2100
tttaactgca tcttcaatgg ccttaccttc ttcaggcaag ttcaatgaca atttcaacat   2160
cattgcagca gacaagatag tggcgatagg gttgacctta ttctttggca aatctggagc   2220
agaaccgtgg catggttcgt acaaaccaaa tgcggtgttc ttgtctggca agaggccaa   2280 ggacgcagat ggcaacaaac ccaaggaacc tgggataacg gaggcttcat cggagatgat   2340
atcaccaaac atgttgctgg tgattataat accatttagg tgggttgggt tcttaactag   2400
gatcatggcg gcagaatcaa tcaattgatg ttgaaccttc aatgtaggga attcgttctt   2460
```

```
gatggtttcc tccacagttt ttctccataa tcttgaagag gccaaaacat tagctttatc   2520
caaggaccaa ataggcaatg gtggctcatg ttgtagggcc atgaaagcgg ccattcttgt   2580
gattctttgc acttctggaa cggtgtattg ttcactatcc caagcgacac catcaccatc   2640
gtcttccttt ctcttaccaa agtaaatacc tcccactaat tctctgacaa caacgaagtc   2700
agtaccttta gcaaattgtg gcttgattgg agataagtct aaaagagagt cggatgcaaa   2760
gttacatggt cttaagttgg cgtacaattg aagttcttta cggattttta gtaaaccttg   2820
ttcaggtcta acactaccgg taccccattt aggaccaccc acagcaccta acaaaacggc   2880
atcagccttc ttggaggctt ccagcgcctc atctggaagt ggaacacctg tagcatcgat   2940
agcagcacca ccaattaaat gattttcgaa atcgaacttg acattggaac gaacatcaga   3000
aatagcttta agaaccttaa tggcttcggc tgtgatttct tgaccaacgt ggtcacctgg   3060
caaaacgacg atcttcttag gggcagacat tagaatggta tatccttgaa atatatatat   3120
atattgctga atgtaaaag gtaagaaaag ttagaaagta agacgattgc taaccaccta   3180
ttggaaaaaa caataggtcc ttaaataata ttgtcaactt caagtattgt gatgcaagca   3240
tttagtcatg aacgcttctc tattctatat gaaaagccgg ttccggcgct ctcacctttc   3300 cttttctcc caatttttca gttgaaaaag gtatatgcgt caggcgacct ctgaaattaa   3360 caaaaattt ccagtcatcg aatttgattc tgtgcgatag cgccctgtg tgttctcgtt   3420 atgttgagga aaaaaataat ggttgctaag agattcgaac tcttgcatct tacgatacct   3480
gagtattccc acagttaact gcggtcaaga tatttcttga atcaggcgcc ttagaccgct   3540
cggccaaaca accaattact tgttgagaaa tagagtataa ttatcctata aatataacgt   3600
ttttgaacac acatgaacaa ggaagtacag gacaattgat tttgaagaga atgtggattt   3660
tgatgtaatt gttgggattc catttttaat aaggcaataa tattaggtat gtagatatac   3720
tagaagttct cctcgaggat ttaggaatcc ataaaaggnn atctgcaatt ctacacaatt   3780
ctagaaatat tattatcatc attttatatg ttaatattca ttgatcctat tacattatca   3840
atccttgcgt ttcagcttcc actaatttag atgactattt ctcatcattt gcgtcatctt   3900
ctaacaccgt atatgataat atactagtaa cgtaaatact agttagtaga tgatagttga   3960
tttttattcc aacataccac ccataatgta atagatctag cttatcgatg ataagctgtc   4020
aaagatgaga attaattcca cggactatag actataccta gtatactccg tctactgtac   4080
gatacacttc cgctcaggtc cttgtccttt aacgaggcct taccactctt ttgttactct   4140
attgatccag ctcagcaaag gcagtgtgat ctaagattct atcttcgcga tgtagtaaaa   4200
ctagctagac cgagaaagag actagaaatg caaaaggcac ttctacaatg gctgccatca   4260
ttattatccg atgtgacgct gcagcttctc aatgatattc gaatacgctt tgaggagata   4320
cagcctaata tccgacaaac tgttttacag atttacgatc gtacttgtta cccatcattg   4380
aattttgaac atccgaacct gggagttttc cctgaaacag atagtatatt tgaacctgta   4440
taataatata tagtctagcg ctttacggaa gacaatgtat gtatttcggt tcctggagaa   4500
actattgcat ctattgcata ggtaatcttg cacgtcgcat ccccggttca ttttctgcgt   4560
ttccatcttg cacttcaata gcatatcttt gttaacgaag catctgtgct tcattttgta   4620
gaacaaaaat gcaacgcgag agcgctaatt tttcaaacaa agaatctgag ctgcattttt   4680
acagaacaga aatgcaacgc gaaagcgcta ttttaccaac gaagaatctg tgcttcattt   4740
ttgtaaaaca aaaatgcaac gcgacgagag cgctaatttt tcaaacaaag aatctgagct   4800
gcatttttac agaacagaaa tgcaacgcga gagcgctatt ttaccaacaa agaatctata   4860
```

```
cttcttttt  gttctacaaa  aatgcatccc  gagagcgcta  ttttctctaac  aaagcatctt    4920 agattacttt  ttttctcctt  tgtgcgctct  ataatgcagt  ctcttgataa  cttttttgcac   4980 tgtaggtccg  ttaaggttag  aagaaggcta  ctttggtgtc  tattttctct  tccataaaaa    5040
aagcctgact  ccacttcccg  cgtttactga  ttactagcga  agctgcgggt  gcattttttc    5100
aagataaagg  catccccgat  tatattctat  accgatgtgg  attgcgcata  ctttgtgaac    5160
agaaagtgat  agcgttgatg  attcttcatt  ggtcagaaaa  ttatgaacgg  tttcttctat    5220
tttgtctcta  tatactacgt  ataggaaatg  tttacatttt  cgtattgttt  tcgattcact    5280
ctatgaatag  ttcttactac  aattttttg   tctaaagagt  aatactagag  ataaacataa    5340
aaaatgtaga  ggtcgagttt  agatgcaagt  tcaaggagcg  aaaggtggat  gggtaggtta    5400
tatagggata  tagcacagag  atatatagca  aagagatact  tttgagcaat  gtttgtggaa    5460
gcggtattcg  caatgggaag  ctccaccccg  gttgataatc  agaaaagccc  caaaaacagg    5520
aagattgtat  aagcaaatat  ttaaattgta  aacgttaata  ttttgttaaa  attcgcgtta    5580
aatttttgtt  aaatcagctc  attttttaac  gaatagcccg  aaatcggcaa  aatcccttat    5640
aaatcaaaag  aatagaccga  gatagggttg  agtgttgttc  cagtttccaa  caagagtcca    5700
ctattaaaga  acgtggactc  caacgtcaaa  gggcgaaaaa  gggtctatca  gggcgatggc    5760
ccactacgtg  aaccatcacc  ctaatcaagt  ttttggggt   cgaggtgccg  taaagcagta    5820
aatcggaagg  gtaaacggat  gccccccattt agagcttgac  ggggaaagcc  ggcgaacgtg    5880
gcgagaaagg  aagggaagaa  agcgaaagga  gcggggcta   gggcggtggg  aagtgtaggg    5940
gtcacgctgg  gcgtaaccac  cacacccgcc  gcgcttaatg  gggcgctaca  gggcaggaat    6000
actctgaata  aaacaactta  tataataaaa  atgc                                  6034
```

```
<210> SEQ ID NO 12
<211> LENGTH: 5056
<212> TYPE: DNA
<213> ORGANISM: Artificial Sequence
<220> FEATURE:
<223> OTHER INFORMATION: Plasmid
<220> FEATURE:
<221> NAME/KEY: LV5
<222> LOCATION: (1)..(40)
<220> FEATURE:
<221> NAME/KEY: pYES backbone
<222> LOCATION: (41)..(5016)
<220> FEATURE:
<221> NAME/KEY: AmpR
<222> LOCATION: (1040)..(1699)
<220> FEATURE:
<221> NAME/KEY: URA3
<222> LOCATION: (1915)..(3022)
<220> FEATURE:
<221> NAME/KEY: LV3
<222> LOCATION: (5017)..(5056)

<400> SEQUENCE: 12
```

```
cctctttata  ttacatcaaa  ataagaaaat  aattataaca  cctgcattaa  tgaatcggcc    60
aacgcgcggg  gagaggcggt  ttgcgtattg  ggcgctcttc  cgcttcctcg  ctcactgact   120
cgctgcgctc  ggtcgttcgg  ctgcggcgag  cggtatcagc  tcactcaaag  gcggtaatac   180
ggttatccac  agaatcaggg  gataacgcag  gaaagaacat  gtgagcaaaa  ggccagcaaa   240
agcccaggaa  ccgtaaaaag  gccgcgttgc  tggcgttttt  ccataggctc  cgcccccctg   300
acgagcatca  caaaaatcga  cgctcaagtc  agaggtggcg  aaacccgaca  ggactataaa   360
gataccaggc  gtttccccct  ggaagctccc  tcgtgcgctc  tcctgttccg  accctgccgc   420
```

```
ttaccggata cctgtccgcc tttctcccct cgggaagcgt ggcgctttct catagctcac      480
gctgtaggta tctcagttcg gtgtaggtcg ttcgctccaa gctgggctgt gtgcacgaac      540
cccccgttca gcccgaccgc tgcgccttat ccggtaacta tcgtcttgag tccaacccgg      600
taagacacga cttatcgcca ctggcagcag ccactggtaa caggattagc agagcgaggt      660
atgtaggcgg tgctacagag ttcttgaagt ggtggcctaa ctacggctac actagaagga      720
cagtatttgg tatctgcgct ctgctgaagc cagttacctt cggaaaaaga gttggtagct      780
cttgatccgg caaacaaacc accgctggta gcggtggttt ttttgtttgc aagcagcaga      840
ttacgcgcag aaaaaaagga tctcaagaag atcctttgat cttttctacg ggtctgacg       900 ctcagtggaa cgaaaactca cgttaaggga ttttggtcat gagattatca aaaaggatct      960
tcacctagat ccttttaaat taaaatgaa gttttaaatc aatctaaagt atatatgagt      1020
aaacttggtc tgacagttac caatgcttaa tcagtgaggc acctatctca gcgatctgtc     1080
tatttcgttc atccatagtt gcctgactcc ccgtcgtgta gataactacg atacgggagc     1140
gcttaccatc tggccccagt gctgcaatga taccgcgaga cccacgctca ccggctccag     1200
atttatcagc aataaaccag ccagccggaa gggccgagcg cagaagtggt cctgcaactt     1260
tatccgcctc cattcagtct attaattgtt gccgggaagc tagagtaagt agttcgccag     1320
ttaatagttt gcgcaacgtt gttggcattg ctacaggcat cgtggtgtca ctctcgtcgt     1380
ttggtatggc ttcattcagc tccggttccc aacgatcaag gcgagttaca tgatccccca     1440
tgttgtgcaa aaaagcggtt agctccttcg gtcctccgat cgttgtcaga gtaagttgg      1500 ccgcagtgtt atcactcatg gttatggcag cactgcataa ttctcttact gtcatgccat     1560
ccgtaagatg cttttctgtg actggtgagt actcaaccaa gtcattctga aatagtgta     1620 tgcggcgacc gagttgctct tgcccggcgt caatacggga taatagtgta tcacatagca     1680
gaactttaaa agtgctcatc attggaaaac gttcttcggg gcgaaaactc tcaaggatct     1740
taccgctgtt gagatccagt tcgatgtaac ccactcgtgc acccaactga tcttcagcat     1800
cttttacttt caccagcgtt tctgggtgag caaaaacagg aaggcaaaat gccgcaaaaa     1860
agggaataag ggcgacacgg aaatgttgaa tactcatact cttcctttt caatgggtaa      1920 taactgatat aattaaattg aagctctaat ttgtgagttt agtatacatg catttactta     1980
taatacagtt ttttagtttt gctggccgca tcttctcaaa tatgcttccc agcctgcttt     2040
tctgtaacgt tcaccctcta ccttagcatc ccttcccttt gcaaatagtc ctcttccaac     2100
aataataatg tcagatcctg tagagaccac atcatccacg gttctatact gttgacccaa     2160
tgcgtctccc ttgtcatcta aacccacacc gggtgtcata atcaaccaat cgtaaccttc     2220
atctcttcca cccatgtctc tttgagcaat aaagccgata acaaaatctt tgtcgctctt     2280
cgcaatgtca acagtacccct tagtatattc tccagtagat agggagccct tgcatgacaa     2340
ttctgctaac atcaaaaggc ctctaggttc ctttgttact tcttctgccg cctgcttcaa     2400
accgctaaca ataccggc ccaccacacc gtgtgcattc gtaatgtctg cccattctgc       2460
tattctgtat acacccgcag agtactgcaa tttgactgta ttccaatgt cagcaaattt       2520 tctgtcttcg aagagtaaaa aattgtactt ggcggataat gcctttagcg gcttaactgt     2580
gccctccatg gaaaaatcag tcaagatatc cacatgtgtt tttagtaaac aaattttggg     2640
acctaatgct tcaactaact ccagtaaatt ccttggtggta cgaacatcca atgaagcaca    2700
caagtttgtt tgcttttcgt gcatgatatt aaatagcttg gcagcaacag gactaggatg    2760
```

```
agtagcagca cgttccttat atgtagcttt cgacatgatt tatcttcgtt tcctgcaggt    2820
ttttgttctg tgcagttggg ttaagaatac tgggcaattt catgtttctt caacactaca    2880
tatgcgtata tataccaatc taagtctgtg ctccttcctt cgttcttcct tctgttcgga    2940
gattaccgaa tcaaaaaaat ttcaagaaaa ccgaaatcaa aaaaagaat  aaaaaaaaaa    3000 tgatgaattg aattgaaaag ctagcttatc gatgataagc tgtcaaagat gagaattaat    3060
tccacggact atagactata ctagatactc cgtctactgt acgatacact tccgctcagg    3120
tccttgtcct ttaacgaggc cttaccactc ttttgttact ctattgatcc agctcagcaa    3180
aggcagtgtg atctaagatt ctatcttcgc gatgtagtaa aactagctag accgagaaag    3240
agactagaaa tgcaaaaggc acttctacaa tggctgccat cattattatc cgatgtgacg    3300
ctgcagcttc tcaatgatat tcgaatacgc tttgaggaga tacagcctaa tatccgacaa    3360
actgttttac agatttacga tcgtacttgt tacccatcat tgaattttga acatccgaac    3420
ctggagtttt tccctgaaac agatagtata tttgaacctg tataataata tatagtctag    3480
cgctttacgg aagacaatgt atgtatttcg gttcctggag aaactattgc atctattgca    3540
taggtaatct tgcacgtcgc atccccggtt catttctgc  gtttccatct tgcacttcaa    3600
tagcatatct ttgttaacga agcatctgtg cttcattttg tagaacaaaa atgcaacgcg    3660
agagcgctaa tttttcaaac aaagaatctg agctgcattt ttacagaaca gaaatgcaac    3720
gcgaaagcgc tattttacca cgaagaatc  tgtgcttcat ttttgtaaaa caaaaatgca    3780
acgcgacgag agcgctaatt tttcaaacaa agaatctgag ctgcattttt acagaacaga    3840
aatgcaacgc gagagcgcta ttttaccaac aaagaatcta tacttctttt ttgttctaca    3900
aaaatgcatc ccgagagcgc tattttccta acaaagcatc ttagattact ttttttctcc    3960
tttgtgcgct ctataatgca gtctcttgat aacttttgc  actgtaggtc cgttaaggtt    4020
agaagaaggc tactttggtg tctattttct cttccataaa aaagcctga  ctccacttcc    4080 cgcgttact  gattactagc gaagctgcgg gtgcattttt tcaagataaa ggcatccccg    4140
attatattct ataccgatgt ggattgcgca ctttgtga   acagaaagtg atagcgttga    4200
tgattcttca ttggtcagaa aattatgaac ggtttcttct attttgtctc tatatactac    4260
gtataggaaa tgtttacatt ttcgtattgt tttcgattca ctctatgaat agttcttact    4320 acaattttt  tgtctaaaga gtaatactag agataaacat aaaaaatgta gaggtcgagt    4380
ttagatgcaa gttcaaggag cgaaaggtgg atgggtaggt tatatagga  tatagcacag    4440 agatatatag caaagagata cttttgagca atgtttgtgg aagcggtatt cgcaatggga    4500
agctccaccc cggttgataa tcagaaaagc cccaaaaaca ggaagattgt ataagcaaat    4560
atttaaattg taaacgttaa tattttgtta aaattcgcgt taaattttg  ttaaatcagc    4620 tcatttttta acgaatagcc cgaaatcggc aaaatccctt ataaatcaaa agaatagacc    4680
gagatagggt tgagtgttgt tccagttccc aacaagagtc cactattaaa gaacgtggac    4740
tccaacgtca aagggcgaaa aagggtctat cagggcgatg gcccactacg tgaaccatca    4800
ccctaatcaa gttttttggg gtcgaggtgc cgtaaagcag taaatcggaa gggtaaacgg    4860
atgcccccat ttagagcttg acggggaaag ccggcgaacg tggcgagaaa ggaagggaag    4920
aaagcgaaag gagcgggggc tagggcggtg ggaagtgtag gggtcacgct gggcgtaacc    4980
accacacccg ccgcgcttaa tggggcgcta cagggcagga atactctgaa taaaacaact    5040
tatataataa aaatgc                                                   5056
```

```
<210> SEQ ID NO 13
<211> LENGTH: 10584
<212> TYPE: DNA
<213> ORGANISM: Artificial Sequence
<220> FEATURE:
<223> OTHER INFORMATION: Cassette with Dictyostelium discoideum DiPKS
      coding sequence, regulatory sequences and integration sequences
<220> FEATURE:
<221> NAME/KEY: LV3
<222> LOCATION: (1)..(40)
<220> FEATURE:
<221> NAME/KEY: S. cerevisiae GAL1 promoter
<222> LOCATION: (41)..(482)
<220> FEATURE:
<221> NAME/KEY: L1
<222> LOCATION: (483)..(522)
<220> FEATURE:
<221> NAME/KEY: DiPKS
<222> LOCATION: (523)..(9966)
<220> FEATURE:
<221> NAME/KEY: Motif 1
<222> LOCATION: (5050)..(5076)
<220> FEATURE:
<221> NAME/KEY: C-methyltransferase domain
<222> LOCATION: (5050)..(5412)
<220> FEATURE:
<221> NAME/KEY: Motif 2
<222> LOCATION: (5309)..(5331)
<220> FEATURE:
<221> NAME/KEY: Motif 3
<222> LOCATION: (5389)..(5421)
<220> FEATURE:
<221> NAME/KEY: L2
<222> LOCATION: (9967)..(10006)
<220> FEATURE:
<221> NAME/KEY: PRM9t
<222> LOCATION: (10007)..(10544)
<220> FEATURE:
<221> NAME/KEY: LV5
<222> LOCATION: (10545)..(10584)

<400> SEQUENCE: 13
aggaatactc tgaataaaac aacttatata ataaaaatgc cggattagaa gccgccgagc      60
gggtgacagc cctccgaagg aagactctcc tccgtgcgtc ctcgtcttca ccggtcgcgt     120
tcctgaaacg cagatgtgcc tcgcgccgca ctgctccgaa caataaagat tctacaatac     180
tagcttttat ggttatgaag aggaaaaatt ggcagtaacc tggccccaca aaccttcaaa     240
tgaacgaatc aaattaacaa ccataggatg ataatgcgat tagttttttta gccttatttc     300 tggggtaatt aatcagcgaa gcgatgattt ttgatctatt aacagatata taaatgcaaa     360
aactgcataa ccactttaac taatactttc aacattttcg gtttgtatta cttcttattc     420
aaatgtaata aaagtatcaa caaaaaattg ttaatatacc tctatacttt aacgtcaagg     480
agctagaaaa tttattataa aaggaagaga ataattaaa caatgaacaa gaactccaaa     540
atccagtccc caaactcttc tgatgttgct gttattggtg ttggttttag attcccaggt     600
aactctaatg acccagaatc tttgtggaac aacttgttgg atggtttcga tgctattacc     660
caagtcccaa agaaagatg ggctacttct tttagagaga tggtttgat caagaacaag     720 ttcggtggtt tcttgaagga ttctgaatgg aagaatttcg accctttgtt ctttggtatc     780
ggtccaaaag aagctccatt cattgatcca caacaaggt tgttgttgtc catcgtttgg     840
gaatctttgg aagatgctta catcagacca gatgaattga gaggttctaa cactggtgtt     900
ttcatcggtg tttctaacaa cgattacacc aagttgggtt tccaagacaa ctactctatt     960
tctccataca ctatgaccgg ctctaactct tcattgaact ccaacagaat ttcctactgc    1020
ttcgatttta gaggtccatc cattactgtt gataccgctt gttcttcttc cttggttctt   1080
```

```
gttaatttgg gtgtccaatc catccaaatg ggtgaatgta agattgctat ttgcggtggt    1140
gttaacgctt tgtttgatcc atctacatct gttgccttt ccaagttggg tgttttgtct     1200
gaaaatggca gatgcaactc ttttagtgat caagcctctg gttacgttag atctgaaggt    1260
gctggtgttg ttgttttgaa gtctttggaa caagctaagt tggatggtga tagaatctac    1320
ggtgttatca agggtgtttc ctctaatgaa gatggtgctt ctaatggtga caagaactct    1380
ttgactactc catcttgtga agcccaatcc attaacattt ctaaggctat ggaaaaggcc    1440
tccttgtctc catctgatat ctattacatt gaagcccatg gtactggtac tccagttggt    1500
gatccaattg aagttaaggc cttgtccaag atcttctcca actctaacaa caaccagttg    1560
aacaacttct ctaccgatgg taatgataac gatgatgatg atgacgataa cacctctcca    1620
gaaccattat tgattggctc attcaagtcc aacatcggtc atttggaatc tgctgctggt    1680
attgcttctt tgattaagtg ttgcttgatg ttgaagaaca ggatgttggt tccatccatt    1740
aactgctcta atttgaaccc atccattcca ttcgatcagt acaacatctc cgttatcaga    1800
gaaatcagac aattcccaac cgataagttg gttaacatcg gtatcaattc tttcggtttc    1860
ggtggttcta actgccattt gattattcaa gagtacaaca caacttcaa gaacaactct     1920
accatctgca ataacaacaa caacaacaat aacaacatcg actacttgat cccaatctcc    1980
tctaagacta agaagtcctt ggataagtac ttgattttga tcaagaccaa ctccaactac    2040
cacaaggata tttctttcga tgacttcgtc aagttccaaa tcagtctaa gcagtacaac     2100
ttgtccaaca gaatgactac cattgctaac gattggaact ccttcattaa gggttctaac    2160
gaattccaca acttgatcga atctaaggat ggtgaaggtg ttcttcatc ttctaacaga     2220
ggtattgatt ccgccaatca aatcaacact actactacct ctaccatcaa cgatatcgaa    2280
cctttgttgg ttttcgtttt ctgtggtcaa ggtccacaat ggaatggtat gattaagacc    2340
ttgtacaact ccgagaacgt tttcaagaac accgttgatc atgttgacag catcttgtac    2400
aagtacttcg gttactccat tttgaacgtc ttgtctaaga tcgatgataa cgacgattcc    2460
atcaaccatc caatagttgc tcaaccatct ttgttcttgt tgcaaattgg tttggtcgag    2520
ttgtttaagt actgggtat ctacccatct atctctgttg gtcattcttt cggtgaagtc     2580
tcttcttatt acttgtccgg tatcatctct ttggaaaccg cttgtaaaat cgtctacgtc    2640
agatcctcta atcagaacaa aactatgggt tccggtaaga tgttggttgt ttctatgggt    2700
tttaagcaat ggaacgatca attctctgct gaatggtccg atattgaaat tgcttgttac    2760
aacgctccag attccatagt tgttactggt aacgaagaaa gattgaaaga attgtccatc    2820
aagttgtccg acgaatccaa tcaaattttc aacaccttct tgaggtcccc atgttctttt    2880
cattcttccc atcaagaagt catcaagggt tctatgttcg aagagttgtc taacttgcaa    2940
tctactggtg aaaccgaaat ccctttgttc tctactgtta ctggtagaca gttttgtct    3000
ggtcatgtta ctgctcaaca catctacgat aatgttagag aaccagtctt gttccaaaag    3060
acgattgaat ccattaccctc ctacatcaag tctcactacc catccaatca aaaggttatc    3120
tacgttgaaa ttgctccaca cccaaccttg ttttcattga tcaaaagtc catcccatcc    3180
tccaacaaga attcctcttc tgttttgtgt ccattgaaca gaaagaaaa ctccaacaac     3240
tcctacaaga agttcgtttc tcagttgtac ttcaacggtg ttaacgttga cttcaacttc    3300
cagttgaact ccatttgcga taacgttaac aacgatcacc atttgaacaa cgtcaagcaa    3360
aactccttca aagagactac caattccttg ccaagatacc aatgggaaca agatgaatat    3420
tggtccgaac cattgatctc cagaaagaat agattggaag gtccaactac ttccttgttg    3480
```

```
ggtcatagaa ttatctacag cttcccagtt ttccaatccg ttttggactt gcaatctgac    3540
aactacaaat acttgttgga ccacttggtt aacggtaagc cagtttttcc aggtgctggt    3600
tatttggata tcatcatcga attcttcgac taccaaaagc agcagttgaa ttcctctgat    3660
tcctctaact cctacatcat caacgttgac aagatccaat tcttgaaccc aattcacttg    3720
accgaaaaca agttgcaaac cttgcaatct tctttcgaac ctatcgttac taagaagtct    3780
gccttctctg ttaacttctt catcaaggat accgtcgagg atcaatctaa ggttaagtct    3840
atgtctgacg aaacttggac taacacttgt aaggctacca tttccttgga caacaacag    3900 ccatctccat cttctacttt gactttgtct aagaagcaag acttgcagat cttgagaaac    3960
agatgcgata ttagcaagct agacaagttt gagttgtacg acaagatctc taagaatttg    4020
ggcttgcagt acaactcctt gtttcaagtt gttgatacca tcgaaactgg taaggattgc    4080
tcttttgcta ctttgtcttt gccagaagat actttgttca ccaccatttt gaacccatgc    4140
ttgttggata actgtttcca tggtttgttg accttgatca acgaaaaggg ttctttcgtt    4200
gtcgagtcca tttcttctgt ttctatctac ttggagaaca tcggttcctt caatcaaact    4260
tctgttggta acgtccagtt ctacttgtac accactattt ctaaagccac ctcctttagt    4320
tctgaaggta cttgtaagtt gttcaccaag gatggttcct tgattttgtc tatcggtaag    4380
ttcatcatca agtccaccaa tccaaagtct actaagacca acgaaactat cgaatctcca    4440
ttggacgaaa ccttctctat tgaatggcaa tctaaggatt ctccaattcc aaccccacaa    4500
caaatccaac aacaatctcc attgaactct aacccatcct tcattagatc taccatcttg    4560
aaggacatcc agttcgaaca atactgctcc tccattatcc acaaagaatt gatcaaccac    4620
gaaaagtaca agaaccagca atccttcgat atcaactcct tggaaaaacca cttgaacgat    4680 gaccaattga tggaatcctt gtccatctcc aaagaatact tgagattctt caccaggatc    4740
atctccatca ttaagcaata cccaaagatc ttgaacgaaa aagagctaaa agaattgaaa    4800
gaaatcatcg aattgaagta cccatccgaa gttcagttgt tggaattcga agttatcgag    4860
aaggtgtcca tgattatccc aaagttgttg ttcgaaaacg acaagcaatc ttccatgacc    4920
ttgttccaag ataacttgtt gaccaggttc tactccaatt ctaactctac cagattctac    4980
ttggaaaggg tttccgaaat ggtcttggaa tctattagac caatcgtcag agaaaagagg    5040
gtgttcagaa ttttggaaat tggtgctggt acaggctctt tgtctaatgt tgttttgact    5100
aagttgaaca cctacttgtc caccttgaat tctaatggtg ttctggtta caacatcatc    5160 attgagtaca ccttcaccga tatttccgcc aacttcatta ttggtgaaat ccaagaaacc    5220
atgtgcaact tgtacccaaa cgttactttc aagttctccg tcttggactt ggagaaagag    5280
attattaact cctccgattt cttgatgggt gattacgata tagttttgat ggcctacgtt    5340
atccatgccg tttctaacat taagttctcc atcgaacagt tgtacaagtt gttgtctcca    5400
agaggttggt tgttgtgtat tgaacctaag tccaacgttg tgttctccga tttggttttc    5460
ggttgtttta atcagtggtg gaactactac gatgatatta gaactaccca ctgctccttg    5520
tctgaatctc aatggaatca gttgttgttg aaccagtcct tgaacaacga atcctcttct    5580
tcttctaact gttacggtgg tttctccaac gtttcttttta ttggtggtga aaaggatgtc    5640
gactcccatt ctttcatatt gcactgccaa aaagaatcca tctcccaaat gaagttagcc    5700
accactatta caacggtttt gtcatctggt tccatcgtta tcgttttgaa ctctcaacaa    5760
ttgaccaaca tgaagtccta cccaaaggtt attgagtata ttcaagaggc tacctctttg    5820
```

```
tgcaagacca ttgaaattat cgattccaag gacgtcttga actctaccaa ttcagttttg   5880
gaaaagatcc aaaagtcctt gttggtgttc tgtttgttgg gttatgactt gttggagaac   5940
aactaccaag aacagtcttt cgaatacgtt aagttgttga acttgatctc tactaccgcc   6000
tcttcatcta atgataagaa accaccaaag gtcttgttga tcaccaagca atctgaaaga   6060
atctccaggt ctttctactc cagatccttg attggtattt ccagaacctc tatgaacgag   6120
tacccaaatt tgtccattac ctctatcgat ttggatacca acgactactc attgcagtct   6180
ttgttgaagc caatcttcag caactctaag ttttccgaca acgagttcat cttcaaaaag   6240
ggcttgatgt tcgtgtccag gatctttaag aacaagcagt tgctagaatc ctccaacgct   6300
tttgaaactg actcttctaa cttgtactgt aaggcctctt ctgacttgtc ttacaagtac   6360
gctattaagc agtctatgtt gaccgaaaat cagatcgaaa tcaaggttga atgcgtcggt   6420
attaacttca aggacaacct attctacaag ggcttgttgc cacaagaaat tttcagaatg   6480
ggtgacatct acaatccacc atatggtttg aatgctctg gtgttattac cagaattggt    6540
tctaacgtca ccgaatactc agttggtcaa atgttttttg gtttcgccag acattctttg   6600
ggttctcatg ttgttaccaa caaggatttg gttatcttga agccagatac catctcattt   6660
tctgaagctg cttctatccc agttgtttac tgtactgctt ggtactcctt gttcaacatt   6720
ggtcagttgt ctaacgaaga atccatccta attcattctg ctactggtgg tgtaggtttg   6780
gcttctttga atttgttgaa aatgaagaat cagcaacagc aaccattgac caatgtttat   6840
gctactgttg gctctaacga agaagaagag ttcttgatcg ataacttcaa caacttgttc   6900
aaagaggacg gcgaaaacat tttctctacc agagacaaag aatactccaa ccagttggaa   6960
tccaagatcg atgttatttt gaacaccttg tccggtgaat tcgtcgaatc taatttcaag   7020
tccttgagat ccttcggtag attgattgat ttgtctgcta ctcacgttta cgccaatcaa   7080
caaattggtc taggtaactt caagttcgac cacttgtatt ctgctgttga cttggaaaga   7140
ttgatcgacg aaaaacctaa gttgttgcag tccatcttgc aaagaattac caactctatc   7200
gtcaacggtt ccttggaaaa aattccaatt accatcttcc catccaccga aactaaggat   7260
gctatcgaat tattgtccaa gagatccat atcggtaaag ttgttgtaga ttgcaccgat   7320
atctctaagt gtaatcctgt tggtgatgtg atcaccaact tctctatgag attgccaaag   7380
ccaaactacc agttgaattt gaactccacc ttgttgatta ctggtcagtc tggtttgtct   7440 atcccttgt tgaattggtt gttgtctaag tctggtggta acgttaagaa cgttgtcatc   7500
atttctaagt ccaccatgaa gtggaagttg cagactatga tttcccatt cgtttccggt   7560 ttcggtatcc attttaacta cgttcaagtc gacatctcca actacgatgc tttgtctgaa   7620
gctattaagc aattgccatc tgatttgcca ccaatcacct ctgttttca tttggctgct   7680 atctacaacg atgttccaat ggatcaagtt accatgtcta ccgttgaatc tgttcataac   7740
cctaaagttt tgggtgccgt taacttgcat agaatctctg tttcttttgg ttggaagttg   7800
aaccacttcg tcttgttctc ttctattact gctattaccg gttacccaga ccaatctatc   7860
tacaattctg ccaactctat tttggacgct ttgtccaact ttagaaggtt tatgggtttg   7920
ccatccttct ccattaactt gggtccaatg aaggatgaag gtaaggtttc taccaacaag   7980
agcatcaaga agctattcaa gtctagaggt ttgccaagcc tatccttgaa caagttattt   8040
ggtttgttgg aggtcgtcat caacaaccca tctaatcatg ttatcccatc ccaattgatt   8100
tgctccccaa tcgatttcaa gacctacatc gaatctttct caactatgag gccaaagttt   8160
ttacacttgc aacctaccat ttccaagcag caatcttcta tcattaacga ttctaccaag   8220
```

```
gcttcctcca acatttcatt gcaagataag atcacctcca aggtgtctga tttgttgtcc    8280
attccaatct ccaagatcaa cttcgatcat ccattgaaac actacggctt ggattctttg    8340
ttgaccgttc aattcaaatc ctggatcgac aaagaattcg aaaagaactt gttcacccat    8400
atccaattgg ccaccatctc tattaactca ttcttggaaa aggtgaacgg cttgtctaca    8460
aacaataaca acaacaacaa ttccaacgtc aagtcctctc catccattgt caagaagaa     8520
atcgttacct tggacaagga tcaacaacca ttgctattga agaacacca gcacattatc     8580
atctccccag atattagaat caacaagcca agagggaat ccttgattag aaccccaatc     8640
ttgaacaaat tcaaccagat caccgaatcc attatcactc catctacacc atctttgtcc    8700
caatccgatg ttttgaaaac tccaccaatc aagtctttga acaacactaa gaactccagc    8760
ttgattaaca ccccaccaat tcaatctgtc caacaacatc aaaagcaaca acaaaaggtc    8820
caagtcatcc aacaacagca acaaccatta tccagattgt cctacaagag caacaacaac    8880
tctttcgttt tgggtatcgg tatttctgtt ccaggtgaac ctatttccca acaatccttg    8940
aaagactcca tctccaatga cttttctgat aaggctgaaa ctaacgagaa ggtcaagaga    9000
atctttgagc aatctcaaat caagaccaga cacttggtta gagattacac taagccagag    9060
aactccatca agttcagaca tttggaaacc attaccgatg tgaacaacca gttcaagaaa    9120
gttgttccag atttggctca acaagcctgt ttgagagctt tgaaagattg gggtggtgat    9180
aagggtgata ttacccatat agtttctgtt acctccaccg gtattatcat cccagatgtt    9240
aatttcaagt tgatcgactt gttgggcttg aacaaggatg ttgaaagagt gtctttgaac    9300
ctaatgggtt gtttggctgg tttgagttct ttgagaactg ctgcttcttt ggctaaggct    9360
tctccaagaa atagaatttt ggttgtctgt accgaagtct gctccttgca tttttctaat    9420
actgatggtg gtgatcaaat ggtcgcctct tctatttttg ctgatggttc tgctgcttac    9480
attattggtt gtaacccaag aattgaagaa accccattat acgaagtcat gtgctccatt    9540
aacagatctt tcccaaatac cgaaaacgcc atggtttggg atttggaaaa agaaggttgg    9600
aactggggtt tggatgcttc tattccaatt gtcattggtt ctggtattga agccttcgtt    9660
gatactttgt tggataaggc taagttgcaa acttccactg ctatttctgc taaggattgc    9720
gaattcttga ttcatactgg tggcaagtcc atcttgatga catcgaaaa ttccttgggt     9780
atcgacccaa agcaaactaa gaatacttgg gatgtttacc atgcctacgg caatatgtca    9840
tctgcctctg ttattttcgt tatggatcat gccagaaagt ccaagtcttt gccaacttac    9900
tcaatttctt tggcttttgg tccaggtttg gcttttgaag gttgtttctt gaagaacgtc    9960
gtctaaagac ataaaactga aacaacacca attaataata gactttacag aagacgggag   10020
acactagcac acaactttac caggcaaggt atttgacgct agcatgtgtc caattcagtg   10080
tcatttatga tttttttgtag taggatataa atatatacag cgctccaaat agtgcggttg   10140
ccccaaaaac accacggaac ctcatctgtt ctcgtacttt gttgtgacaa agtagctcac   10200
tgccttatta tcacattttc attatgcaac gcttcggaaa atacgatgtt gaaaatgcct   10260
ctagagatga aaaacaatcg taaagggtc ctgcgtaatt gaaacatttg atcagtatgc    10320
agtggcacag aaacaaccag gaatactata gtcataggca atacaaggta tatattggct   10380
atgcagaccc ctccagaaag taccgacgtc aagttagata cacttaacga acctagtgca   10440
catttaattg agaaaaatgt ggctcttcct aaggacatat tccgttcgta cttgagttat   10500
tggatctatg aaatcgctcg ctatacacca gtcatgattt tgtccctctt tatattacat   10560
```
caaaataaga aaataattat aaca                                        10584

<210> SEQ ID NO 14
<211> LENGTH: 4909
<212> TYPE: DNA
<213> ORGANISM: Artificial Sequence
<220> FEATURE:
<223> OTHER INFORMATION: Cassette with Cas9 coding sequence, regulatory
      sequences and integration sequences
<220> FEATURE:
<221> NAME/KEY: LV3
<222> LOCATION: (1)..(40)
<220> FEATURE:
<221> NAME/KEY: TEF1p
<222> LOCATION: (41)..(446)
<220> FEATURE:
<221> NAME/KEY: Cas9
<222> LOCATION: (470)..(4609)
<220> FEATURE:
<221> NAME/KEY: LV5
<222> LOCATION: (4870)..(4909)

<400> SEQUENCE: 14
aggaatactc tgaataaaac aacttatata ataaaaatgc atagcttcaa aatgtttcta      60 ctccttttt actcttccag attttctcgg actccgcgca tcgccgtacc acttcaaaac     120
acccaagcac agcatactaa atttcccctc tttcttcctc tagggtgtcg ttaattaccc    180
gtactaaagg tttggaaaag aaaaaagaga ccgcctcgtt tcttttcttt cgtcgaaaaa    240
ggcaataaaa attttatca cgtttctttt tcttgaaaat ttttttttg atttttttct      300 ctttcgatga cctcccattg atatttaagt taataaacgg tcttcaattt ctcaagtttc    360
agtttcattt ttcttgttct attacaactt tttttacttc ttgctcatta gaaagaaagc    420
atagcaatct aatctaagtt ttctagaact agtggatccc ccgggaaaaa tggacaagaa    480
gtactccatt gggctcgata tcggcacaaa cagcgtcggc tgggccgtca ttacggacga    540
gtacaaggtg ccgagcaaaa aattcaaagt tctgggcaat accgatcgcc acagcataaa    600
gaagaacctc attggcgccc tcctgttcga ctccggggag acggccgaag ccacgcggct    660
caaaagaaca gcacggcgca gatatacccg cagaaagaat cggatctgct acctgcagga    720
gatctttagt aatgagatgg ctaaggtgga tgactctttc ttccataggc tggaggagtc    780 cttttttggtg gaggaggata aaaagcacga gcgccaccca atctttggca atatcgtgga    840
cgaggtggcg taccatgaaa agtacccaac catatatcat ctgaggaaga agcttgtaga    900
cagtactgat aaggctgact tgcggttgat ctatctcgcg ctggcgcata tgatcaaatt    960
tcggggacac ttcctcatcg aggggaccct gaacccagac aacagcgatg tcgacaaact   1020
ctttatccaa ctggttcaga cttacaatca gcttttcgaa gagaacccga tcaacgcatc   1080
cggagttgac gccaaagcaa tcctgagcgc taggctgtcc aaatcccggc ggctcgaaaa   1140
cctcatcgca cagctccctg gggagaagaa gaacggcctg tttggtaatc ttatcgccct   1200
gtcactcggg ctgaccccca actttaaatc taacttcgac ctggccgaag atgccaagct   1260
tcaactgagc aaagacacct acgatgatga tctcgacaat ctgctggccc agatcggcga   1320
ccagtacgca gacctttttt tggcggcaaa gaacctgtca gacgccattc tgctgagtga   1380
tattctcgga gtgaacacgg agatcaccaa agctccgctg agcgctagta tgatcaagcg   1440
ctatgatgag caccaccaag acttgacttt gctgaaggcc cttgtcagac agcaactgcc   1500
tgagaagtac aaggaaattt tcttcgatca gtctaaaaat ggctacgccg gatacattga   1560
cggcggagca agccaggagg aatttttacaa atttattaag cccatcttgg aaaaaatgga   1620

```
cggcaccgag gagctgctgg taaagcttaa cagagaagat ctgttgcgca acagcgcac      1680 tttcgacaat ggaagcatcc cccaccagat tcacctgggc gaactgcacg ctatcctcag     1740
gcggcaagag gatttctacc ccttttttgaa agataacagg gaaaagattg agaaaatcct    1800
cacatttcgg ataccctact atgtaggccc cctcgcccgg ggaaattcca gattcgcgtg    1860
gatgactcgc aaatcagaag agaccatcac tccctggaac ttcgaggaag tcgtggataa    1920
gggggcctct gcccagtcct tcatcgaaag gatgactaac tttgataaaa atctgcctaa    1980
cgaaaaggtg cttcctaaac actctctgct gtacgagtac ttcacagttt ataacgagct    2040
caccaaggtc aaatacgtca cagaagggat gagaaagcca gcattcctgt ctggagagca    2100
gaagaaagct atcgtggacc tcctcttcaa gacgaaccgg aaagttaccg tgaaacagct    2160
caaagaagac tatttcaaaa agattgaatg tttcgactct gttgaaatca gcggagtgga    2220
ggatcgcttc aacgcatccc tgggaacgta tcacgatctc ctgaaaatca ttaaagacaa    2280
ggacttcctg acaatgagg agaacgagga cattcttgag gacattgtcc tcacccttac     2340
gttgtttgaa gataggagaga tgattgaaga acgcttgaaa acttacgctc atctcttcga   2400
cgacaaagtc atgaaacagc tcaagaggcg ccgatataca ggatggggc ggctgtcaag     2460 aaaactgatc aatgggatcc gagacaagca gagtggaaag acaatcctgg attttcttaa    2520
gtccgatgga tttgccaacc ggaacttcat gcagttgatc catgatgact ctctcacctt    2580
taaggaggac atccagaaag cacaagtttc tggccagggg gacagtcttc acgagcacat    2640
cgctaatctt gcaggtagcc cagctatcaa aaagggaata ctgcagaccg ttaaggtcgt    2700
ggatgaactc gtcaaagtaa tgggaaggca taagcccgag aatatcgtta tcgagatggc    2760
ccgagagaac caaactaccc agaagggaca gaagaacagt agggaaagga tgaagaggat    2820
tgaagagggt ataaaagaac tggggtccca aatccttaag gaacacccag ttgaaaacac    2880
ccagcttcag aatgagaagc tctacctgta ctacctgcag aacggcaggg acatgtacgt    2940
ggatcaggaa ctggacatca atcggctctc cgactacgac gtggatcata tcgtgcccca    3000
gtcttttctc aaagatgatt ctattgataa taaagtgttg acaagatccg ataaaaatag    3060
agggaagagt gataacgtcc cctcagaaga agttgtcaag aaaatgaaaa attattggcg    3120
gcagctgctg aacgccaaac tgatcacaca acggaagttc gataatctga ctaaggctga    3180
acgaggtggc ctgtctgagt tggataaagc cggcttcatc aaaaggcagc ttgttgagac    3240
acgccagatc accaagcacg tggcccaaat tctcgattca cgcatgaaca ccaagtacga    3300
tgaaaatgac aaactgattc gagaggtgaa agtgattact ctgaagtcta agctggtctc    3360
agatttcaga aaggactttc agttttataa ggtgagagag atcaacaatt accaccatgc    3420
gcatgatgcc tacctgaatg cagtggtagg cactgcactt atcaaaaaat atcccaagct    3480
tgaatctgaa tttgtttacg gagactataa agtgtacgat gttaggaaaa tgatcgcaaa    3540
gtctgagcag gaaataggca aggccaccgc taagtacttc ttttacagca atattatgaa    3600 tttttttcaag accgagatta cactggccaa tggagagatt cggaagcgac cacttatcga    3660
aacaaacgga gaaacaggag aaatcgtgtg ggacaagggt agggatttcg cgacagtccg    3720
gaaggtcctg tccatgccgc aggtgaacat cgttaaaaag accgaagtac agaccggagg    3780
cttctccaag gaaagtatcc tcccgaaaag gaacagcgac aagctgatcg cacgcaaaaa    3840
agattgggac cccaagaaat acggcggatt cgattctcct acagtcgctt acagtgtact    3900
ggttgtggcc aaagtggaga aagggaagtc taaaaaactc aaaagcgtca aggaactgct    3960
gggcatcaca atcatggagc gatcaagctt cgaaaaaaac cccatcgact tctctgaggc    4020
```

```
gaaaggatat aaagaggtca aaaaagacct catcattaag cttcccaagt actctctctt    4080
tgagcttgaa aacggccgga aacgaatgct cgctagtgcg ggcgagctgc agaaaggtaa    4140
cgagctggca ctgccctcta aatacgttaa tttcttgtat ctggccagcc actatgaaaa    4200
gctcaaaggg tctcccgaag ataatgagca gaagcagctg ttcgtggaac aacacaaaca    4260
ctaccttgat gagatcatcg agcaaataag cgaattctcc aaaagagtga tcctcgccga    4320
cgctaacctc gataaggtgc tttctgctta caataagcac agggataagc ccatcaggga    4380
gcaggcagaa aacattatcc acttgtttac tctgaccaac ttgggcgcgc ctgcagcctt    4440
caagtacttc gacaccacca tagacagaaa gcggtacacc tctacaaagg aggtcctgga    4500
cgccacactg attcatcagt caattacggg gctctatgaa acaagaatcg acctctctca    4560
gctcggtgga gacagcaggg ctgaccccaa gaagaagagg aaggtgtgat ctcttctcga    4620
gtcatgtaat tagttatgtc acgcttacat tcacgccctc cccccacatc cgctctaacc    4680
gaaaaggaag gagttagaca acctgaagtc taggtcccta tttatttttt tatagttatg    4740
ttagtattaa gaacgttatt tatatttcaa attttctttt tttttctgta cagacgcgtg    4800
tacgcatgta acattatact gaaaaccttg cttgagaagg ttttgggacg ctcgaaggct    4860
ttaatttgcc ctctttatat tacatcaaaa taagaaaata attataaca               4909
```